(12) United States Patent (10) Patent No.: US 8,039,623 B2
Cottrell et al. (45) Date of Patent: *Oct. 18, 2011

(54) INHIBITORS OF SERINE PROTEASES, PARTICULARLY HCV NS3-NS4A PROTEASE

(75) Inventors: Kevin M. Cottrell, Cambridge, MA (US); Robert B. Perni, Marlborough, MA (US); Janos Pitlik, Westborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 82 days.

This patent is subject to a terminal disclaimer.

(21) Appl. No.: 11/716,248

(22) Filed: Mar. 9, 2007

(65) Prior Publication Data

US 2007/0161789 A1 Jul. 12, 2007

Related U.S. Application Data

(63) Continuation of application No. 10/964,214, filed on Oct. 12, 2004, now Pat. No. 7,208,600.

(60) Provisional application No. 60/510,156, filed on Oct. 10, 2003, provisional application No. 60/513,768, filed on Oct. 23, 2003.

(51) Int. Cl.
*C07D 241/02* (2006.01)
*A61K 31/495* (2006.01)

(52) U.S. Cl. .................... 544/406; 544/405; 514/255.06

(58) Field of Classification Search .................. 544/406, 544/405; 514/255.06
See application file for complete search history.

(56) References Cited

U.S. PATENT DOCUMENTS

| | | | |
|---|---|---|---|
| 5,484,801 A | 1/1996 | Al-Razzak et al. | |
| 5,807,876 A | 9/1998 | Armistead et al. | |
| 5,948,436 A | 9/1999 | Al-Razzak et al. | |
| 6,037,157 A | 3/2000 | Norbeck et al. | |
| 6,054,472 A | 4/2000 | Armistead et al. | |
| 6,265,380 B1 | 7/2001 | Tung et al. | |
| 6,344,465 B1 | 2/2002 | Armistead et al. | |
| 6,498,178 B2 | 12/2002 | Stamos et al. | |
| 6,541,496 B1 | 4/2003 | Armistead et al. | |
| 6,608,067 B1 | 8/2003 | Tung et al. | |
| 6,617,309 B2 | 9/2003 | Tung et al. | |
| 6,909,000 B2 | 6/2005 | Farmer et al. | |
| 7,109,172 B2 | 9/2006 | Britt et al. | |
| 7,208,600 B2 * | 4/2007 | Cottrell et al. ................ | 544/406 |
| 7,241,796 B2 | 7/2007 | Farmer et al. | |
| 7,273,885 B2 | 9/2007 | Pitlik et al. | |
| 2003/0236242 A1 | 12/2003 | Perni et al. | |
| 2004/0077600 A1 | 4/2004 | Tung et al. | |
| 2004/0266731 A1 | 12/2004 | Tung et al. | |
| 2005/0080017 A1 | 4/2005 | Cottrell et al. | |
| 2005/0090450 A1 | 4/2005 | Farmer et al. | |
| 2005/0119189 A1 | 6/2005 | Cottrell et al. | |
| 2005/0137139 A1 | 6/2005 | Perni et al. | |
| 2005/0197299 A1 | 9/2005 | Babine et al. | |
| 2005/0215486 A1 | 9/2005 | Cottrell et al. | |
| 2006/0211629 A1 | 9/2006 | Britt et al. | |
| 2007/0179167 A1 | 8/2007 | Cottrell et al. | |
| 2007/0292933 A1 | 12/2007 | Pitlik et al. | |
| 2008/0045480 A1 | 2/2008 | Farmer et al. | |

FOREIGN PATENT DOCUMENTS

| | | |
|---|---|---|
| EP | 0675112 | 10/1995 |
| WO | 94/14436 | 7/1994 |
| WO | 95/07696 | 3/1995 |
| WO | 95/09614 | 4/1995 |
| WO | 97/40028 | 10/1997 |
| WO | 98/17679 | 4/1998 |
| WO | 98/40381 | 9/1998 |
| WO | 0009543 | 2/2000 |
| WO | 00/56331 | 9/2000 |
| WO | 01/74768 | 10/2001 |
| WO | 02/08244 | 1/2002 |
| WO | 02/18369 | 3/2002 |
| WO | 02/060926 | 8/2002 |
| WO | 03/006490 | 1/2003 |
| WO | 03/035060 | 5/2003 |
| WO | 03/064416 | 8/2003 |
| WO | 2004/037855 | 5/2004 |
| WO | 2004/092161 | 10/2004 |
| WO | 2004/096162 | 10/2004 |
| WO | 2004/103996 | 12/2004 |

OTHER PUBLICATIONS

Alberti, A. et al., "Natural History of Hepatitis C," J. Hepatology, 31., (Suppl. 1) pp. 17-24 (1999).
Alter, M. J. "Hepatitis C Virus Infection in the United States," J. Hepatology, 31., (Supp. 1), pp. 88-91 (1999).
Alter, M.J. et al., The Epidemiology of Viral Hepatitis in the United States, Gastroenterol. Clin. North Am., 23, pp. 437-455 (1994).

(Continued)

*Primary Examiner* — Shailendra Kumar
(74) *Attorney, Agent, or Firm* — Susan C. Kelly

(57) ABSTRACT

The present invention relates to compounds of formula I:

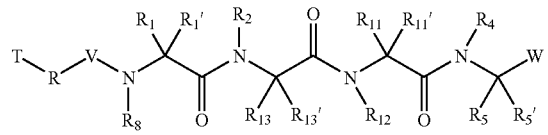

I or a pharmaceutically acceptable salt or mixtures thereof that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection and to processes for preparing the compounds. The invention also relates to methods of treating an HCV infection in a patient by administering a composition comprising a compound of this invention. The invention further relates to processes for preparing these compounds.

9 Claims, No Drawings

OTHER PUBLICATIONS

Bartenschlager, R. et al., "Nonstructual Protein 3 of the Hepatitis C Virus Encodes a Serine-Type Proteinase Required for Cleavage at the NS3/4 and NS4/5 Junctions," J. Virol., 67, pp. 3835-3844 (1993).

Chambers, T.J. et al., "Evidence that the N-terminal Domain of Nonstructual Protein NS3 From Yellow Fever Virus is a Serine Protease Responsible for Site-Specific Cleavages in the Viral Polyprotein," Proc. Natl. Acad. Sci. USA, 87, pp. 8898-8902 (1990).

Choo, Q.L. et al., "Genetic Organization and Diversity of the Hepatitis C Virus." Proc. Natl. Acad. Sci. USA, 88 pp. 2451-2455 (1991).

Clayette, P. et al. "IFN-tau, A New Interferon Type I with Antiretroviral activity" Pathol. Biol. (Paris) 47, pp. 553-559 (1999).

Davis et al., "Future Options for the Management of Hepatitis C." Seminars in Liver Disease 19, pp. 103-112 (1999).

Field, L. et al., "Organic Disulfides and Related Substances. 42. Synthesis and Properties of Some Tertiary Disulfides, Especially Involving Penicillamine," J. Org. Chem., pp. 2624-2629 (1979).

Grakoui, E. et al., "Characterization of the Hepatitis C Virus-Encoded Serine Proteinase: Determination of Proteinase-Dependent Polyprotein Cleavage Sites," J. Virol., 67, pp. 2832-2843 (1993).

Grakoui, A. et al., "Expression and Identification of Hepatitis C Virus Polyprotein Cleavage Products," J. Virol., 67, pp. 1385-1395 (1993).

Holladay, M.W. et al., "Dual Antagonists of Platelet Activating Factor and Histamine. Identification of the Structual Requirements for Dual Activity of N-Acyl-4-(5,6-dihydro-11H-benzo[5,6]cyclohepta-[1,2-b]pyridin-11-ylidene) piperdines," J. Med. Chem., 34, pp. 457-461 (1991).

Iwarson, S. "The Natural Course of Chronic Hepatitis C," FEMS Microbiology Reviews, 14, pp. 201-204 (1994).

Janssen, H. L. A. et al., "Suicide Associated with Alfa-Interferon Therapy for Chronic Viral Hepatitis," J. Hepatol., 21, pp. 241-243 (1994).

Johansson, Anja et al., "Acyl sulfonamides as potent protease inhibitors of the hepatitis C virus full-length NS3 (protease-helicase/NTPase): A comparative study of different c-terminals," Bioorganic & Medicinal Chemistry, Elsevier Science Ltd. GB, vol. 11, pp. 2551-2568 (2003).

Kanamasa, S. et al., "Highly Diastereoselective Michael Addition of Lithiated Camphor Imines of Glycine Esters to a, B-Unsaturated Esters. Synthesis of Optically Pure 5-Oxo-2,4-pyrrolidinedicaboxylates of Unnatural Setroechemistry," J. Org. Chem, 56, pp. 2875-2883 (1991).

Kao, J.H. et al., "Efficicacy of Consensus Interferon in the Treatment of Chronic Hepatitis C" J. Gastroenterol. Hepatol. 15, pp. 1418-1423 (2000).

Kato, N. et al., "Molecular Cloning of the Human Hepatitis C Virus Genome From Japanese Patients with Non-A, Non-B Hepatitis," Proc. Natl. Acad. Sci. USA, 87 pp. 9524-9528 (1990).

Kempf, D.J. et al., "Symmetry-Based Inhibitors of HIV Protease. Structure-Activity Studies of Acylated 2,4-Diamino-1,5-diphenyl-3-hydroxypentane and 2,5-Diamino-1, 6-diphenylhexane-3,4-diol," J. Med. Chem., pp. 320-330 (1993).

Kew, M.C. "Hepatitis C and Hepatocellular Carcinoma", FEMS Microbiology Reviews, 14, pp. 211-220 (1994).

Lavanchy, D. "Global Surveillance and Control of Hepatitis C," J. Viral Hepatitis, 6, pp. 35-47 (1999).

Lin, C. et al., "Hepatitis C Virus NS3 Serine Proteinase: Trans-Cleavage Requirements and Processing Kinetics", J. Virol., 68 pp. 8147-8157 (1994).

Markland, W. et al., "Board-Spectrum Antiviral Activity of the IMP Dehydrogenase Inhibitor VX-497: a Comparision with Ribavirin and Demonstration of Antiviral Additivity with Alpha Interferon," Antimicrobial & Antiviral Chemotherapy, 44, p. 859 (2000).

Moradpour, D. et al., "Current and Evolving Therapies for Hepatitis C," Eur. J. Gastroenterol. Hepatol., 11, pp. 1199-1202 (1999).

Perni, Robert B. et al., "Inhibitors of hepatitis C virus NS3.4A protease. Part 3: P2 Proline Variants," Bioorganic & Medicinal Chemistry Letters, Oxfrod GB, vol. 14, pp. 1939-1942 (2004).

Perni, Robert B. et al., "Inhibitors of hepatitis C virus NS3.4A protease 2. Warhad SAR and optimization," Bioorganic & Medicinal Chemistry Letters, vol. 14, pp. 1441-1446 (2004).

Perni, Robert B. et al.,Inhibitors of hepatitis C virus NS3cntdot4A protease 1. Non-charged tetrapeptide variants, Bioorganic & Medicinal Chemistry Letters, vol. 13, pp. 4059-4063 (2003).

Poliakov, A. et al., "Structure-activity relationship for the selectivity of hepatitis C virus NS3 protease inhibitors" BBA-General Subject, Elsevier Science Publishers, NL, vol. 1672, 51-59 (2004).

Reddy, K.R. et al. Efficiacy and Safety of Pegylated (40-kd) interferon alpha-2aa compared with interferon alpha-2a in noncirrhotic patients with chronic hepatitis C (Hepatology, 33, pp. 433-438 (2001).

Renault, P.F. et al., "Side Effects of Alpha Interferon," Seminars in Liver Disease, 9, pp. 273-277. (1989).

Saito, I. et al., "Hepatitis C Virus Infection is Associated with the Development of Hepatocellular Carcinoma," Proc. Natl. Acad. Sci. USA, 87, pp. 6547-6549 (1990).

Sauder, D. N. "Immunodulatory and Pharmacologic Properties of Imiquimod" J. Am. Acad. Dermatol., 43 pp. S6-S11 (2000).

Takamizawa, A. et al. "Structure and Organization of the Hepatitis C Virus Genome Isolated From Human Carriers," J. Virol., 65, pp. 1105-1113 (1991).

Tazulakhova, E.B. et al., "Russian Experience in Screening, analysis, and Clinical Application of Novel Interferon Inducers" J. Interferon Cytokine Res., 21 pp. 65-73 (2001).

Tomei, L. et al., "NS3 is a serine protease required for processing of hepatitis C virus polyprotein", J. Virol., 67, pp. 4017-4026 (1993).

Weiland, O., "Interferon Therapy in Chronic Hepatitis C Virus Infection", FEMS Microbiol. Rev., 14, pp. 279-288 (1994).

Walker, M.A. et al., "Hepatitis C Virus: An Overview of Current Approaches and Progress," DDT, 4, pp. 518-529 (1999).

Yee, Ying K. et al., "A Novel Series of Selective Leukotriene Antagonists: Exploration and Optimization of the Acidic Region in 1,6-Disubstituted Indoles and Indazoles," J. Med. Chem., 33(9), pp. 2437-2451 (1990).

Yun, Chul-Ho et al., "Role of Cytochrome P-450 3A(4) in N-Dealkylation and C-Hydroxylation," Drug Metabolism & Disposition, vol. 21 pp. 403-407 (1993).

\* cited by examiner

INHIBITORS OF SERINE PROTEASES, PARTICULARLY HCV NS3-NS4A PROTEASE

CROSS REFERENCE TO RELATED APPLICATIONS

This application is a continuation application of U.S. Ser. No. 10/964,214, filed Oct. 12, 2004, now U.S. Pat. No. 7,208,600, which claims the benefit, under 35 U.S.C. §119, of U.S. Provisional patent application Ser. No. 60/510,156, filed Oct. 10, 2003, entitled "Inhibitors of Serine Proteases, Particularly HCV NS3-NS4A Protease", and U.S. Provisional patent application Ser. No. 60/513,768, filed Oct. 23, 2003, entitled "Inhibitors of Serine Proteases, Particularly HCV NS3-NS4A Protease", and the entire contents of these applications are hereby incorporated by reference.

TECHNICAL FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," *J. Hepatology*, 31., (Suppl. 1), pp. 17-24 (1999)]. Nearly four million individuals may be infected in the United States alone [M. J. Alter et al., "The Epidemiology of Viral Hepatitis in the United States, *Gastroenterol. Clin. North Am.*, 23, pp. 437-455 (1994); M. J. Alter "Hepatitis C Virus Infection in the United States," *J. Hepatology*, 31., (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews*, 14, pp. 201-204 (1994); D. Lavanchy, "Global Surveillance and Control of Hepatitis C," *J. Viral Hepatitis*, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211-220 (1994); I. Saito et. al., "Hepatitis C Virus Infection is Associated with the Development of Hepatocellular Carcinoma," *Proc. Natl. Acad. Sci. USA*, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." *Proc. Natl. Acad. Sci. USA*, 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524-9528 (1990); A. Takamizawa et. al., "Structure and Organization of the Hepatitis C Virus Genome Isolated From Human Carriers," *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," *J. Virol.*, 67, pp. 3835-3844 (1993); A. Grakoui et. al., "Characterization of the Hepatitis C Virus-Encoded Serine Proteinase: Determination of Proteinase-Dependent Polyprotein Cleavage Sites," *J. Virol.*, 67, pp. 2832-2843 (1993); A. Grakoui et. al., "Expression and Identification of Hepatitis C Virus Polyprotein Cleavage Products," *J. Virol.*, 67, pp. 1385-1395 (1993); L. Tomei et. al., "NS3 is a serine protease required for processing of hepatitis C virus polyprotein", *J. Virol.*, 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man indicating that interrupting this stage of the viral life cycle results in therapeutically active agents. Consequently HCV NS3 serine protease is also an attractive target for drug discovery.

There are not currently any satisfactory anti-HCV agents or treatments. Until recently, the only established therapy for HCV disease was interferon treatment. Until recently, the only established therapy for HCV disease was interferon treatment. However, interferons have significant side effects [M. A. Wlaker et al., "Hepatitis C Virus: An Overview of Current Approaches and Progress,"*DDT*, 4, pp. 518-29 (1999); D. Moradpour et al., "Current and Evolving Therapies for Hepatitis C," *Eur. J. Gastroenterol. Hepatol.*, 11, pp. 1199-1202 (1999); H. L. A. Janssen et al. "Suicide Associated with Alfa-Interferon Therapy for Chronic Viral Hepatitis," *J. Hepatol.*, 21, pp. 241-243 (1994); P. F. Renault et al., "Side Effects of Alpha Interferon," *Seminars in Liver Disease*, 9, pp. 273-277. (1989)] and induce long term remission in only a fraction (~25%) of cases [O. Weiland, "Interferon Therapy in Chronic Hepatitis C Virus Infection", *FEMS Microbiol. Rev.*, 14, pp. 279-288 (1994)]. Recent introductions of the pegylated forms of interferon (PEG-INTRON® and PEGASYS®) and the combination therapy of ribavirin and pegylated interferon (REBETROL®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention addresses these needs by providing a compound of formula I:

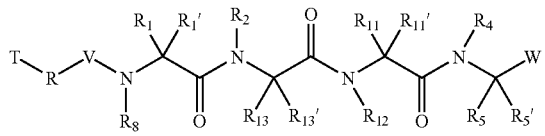

I or a pharmaceutically acceptable salt or mixtures thereof, wherein the variables are as defined herein.

The present invention also provides a compound of formula II:

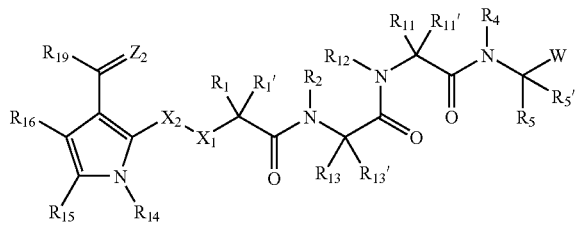

II or a pharmaceutically acceptable salt or mixtures thereof, wherein the variables are as defined herein.

The present invention also provides a compound of formula IV:

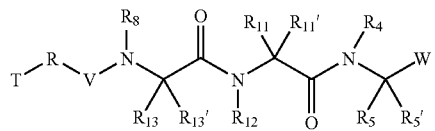

IV or a pharmaceutically acceptable salt or mixtures thereof wherein the variables are as defined herein.

The invention also relates to compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

The invention also relates to processes for preparing the compounds of formula I.

DETAILED DESCRIPTION OF THE INVENTION

The present invention provides a compound of formula I:

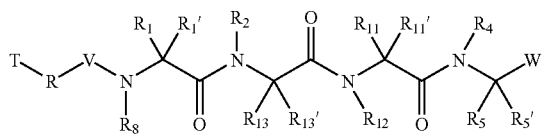

I or a pharmaceutically acceptable salt or mixtures thereof, wherein:

V is —C(O)—, —S(O)—, —C(R')$_2$— or —S(O)$_2$—;
R is —C(O)—, —S(O)—, —S(O)$_2$—, —N(R$_8$)—, —O—, or a bond;
T is:
  (C6-C10)-aryl,
  (C6-C10)-aryl-(C1-C12)aliphatic,
  (C3-C10)-cycloalkyl or -cycloalkenyl,
  [(C3-C10)-cycloalkyl or -cycloalkenyl]-(C1-C12)-aliphatic,
  (C3-C10)-heterocyclyl,
  (C3-C10)-heterocyclyl-(C1-C12)-aliphatic,
  (C5-C10)heteroaryl, or
  (C5-C10)heteroaryl-(C1-C12)-aliphatic;
    wherein up to 3 aliphatic carbon atoms in T may be optionally replaced with —S—, —S(O)—, —S(O)$_2$—, —O—, —N—, or —N(H)—, in a chemically stable arrangement;
    wherein each T may be optionally substituted with up to 3 J substituents;
J is halogen, —OR', —OC(O)N(R')2, —NO$_2$, —CN, —CF$_3$, —OCF$_3$, —R', oxo, thioxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'), wherein;
  two R' groups together with the atoms to which they are bound form a 3- to 10-membered aromatic or non-aromatic ring system having up to 3 heteroatoms independently selected from N, NH, O, S, SO, or SO$_2$, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from J$_2$;
  each R' is independently selected from:
    hydrogen-,
    (C1-C12)-aliphatic-,
    (C3-C10)-cycloalkyl or -cycloalkenyl-,
    [(C3-C10)-cycloalkyl or -cycloalkenyl]-(C1-C12)-aliphatic-,
    (C6-C10)-aryl-,
    (C6-C10)-aryl-(C1-C12)aliphatic-,
    (C3-C10)-heterocyclyl-,
    (C6-C10)-heterocyclyl-(C1-C12)aliphatic-,
    (C5-C10)-heteroaryl-, or
    (C5-C10)-heteroaryl-(C1-C12)-aliphatic-,
  wherein R' has up to 3 substituents selected independently from J$_2$;
J$_2$ is halogen, —OR', —OC(O)N(R')$_2$, —NO$_2$, —CN, —CF$_3$, —OCF$_3$, —R', oxo, thioxo, 1,2-methylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'); or T is:

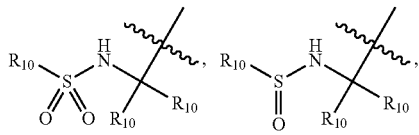

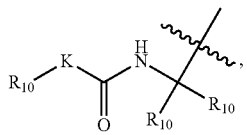

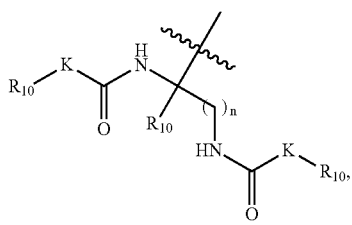

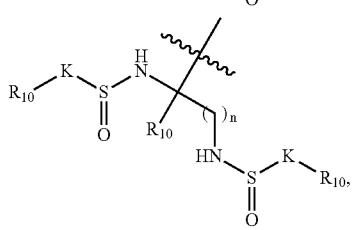

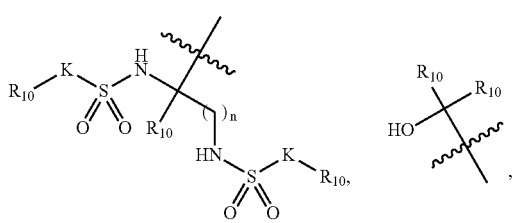

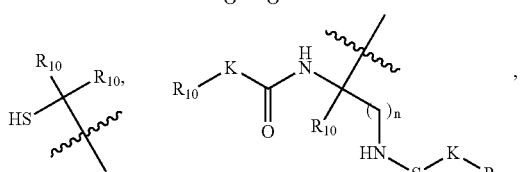

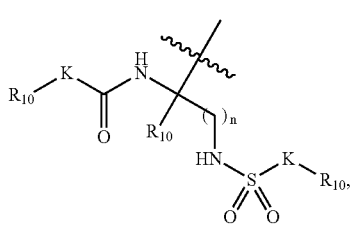

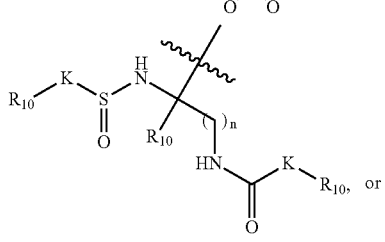

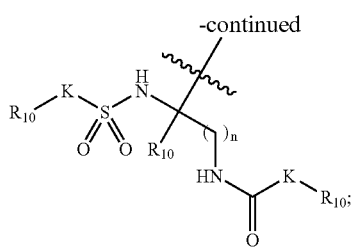

wherein:
R$_{10}$ is:
hydrogen,
(C1-C12)-aliphatic,
(C6-C10)-aryl,
(C6-C10)-aryl-(C1-C12)aliphatic,
(C3-C10)-cycloalkyl or -cycloalkenyl,
[(C3-C10)-cycloalkyl or -cycloalkenyl]-(C1-C12)-aliphatic,
(C3-C10)-heterocyclyl,
(C3-C10)-heterocyclyl-(C1-C12)-aliphatic,
(C5-C10)-heteroaryl, or
(C5-C10)-heteroaryl-(C1-C12)-aliphatic,
K is a bond, (C1-C12)-aliphatic, —O—, —S—, —NR$_9$—, —C(O)—, or —C(O)—NR$_9$—, wherein R$_9$ is hydrogen or (C1-C12)-aliphatic;
n is 1-3; or
T is selected from N(R$_{17}$)$_2$;
W is:

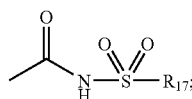
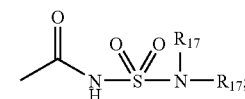
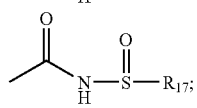
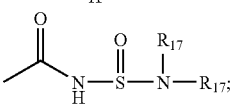

wherein each R$_{17}$ is independently:
hydrogen-,
(C1-C12)-aliphatic-,
(C3-C10)-cycloalkyl- or cycloalkenyl-,
[(C3-C10)-cycloalkyl- or cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)-aliphatic-,
(C5-C10)heteroaryl-, or
(C5-C10)heteroaryl-(C1-C12)-aliphatic-, or
wherein two R$_{17}$ groups, which are bound to the same nitrogen atom, together with that nitrogen atom, optionally form a (C3-C10)-membered saturated or partially unsaturated heterocyclic ring system having in addition to the nitrogen up to 2 additional heteroatoms selected from N, NH, O, S, SO, and SO$_2$ and wherein said ring is optionally substituted with up to 3 J substituents;
wherein R$_{17}$ is optionally substituted with up to 3 J substituents;
R$_5$ and R$_{5'}$ are independently hydrogen or (C1-C12)-aliphatic, wherein any hydrogen is optionally replaced with halogen, and wherein any terminal carbon atom is optionally substituted with sulfhydryl or hydroxy, and wherein up to two aliphatic carbon atoms may be replaced by a heteroatom selected from N, NH, O, S, SO, or $SO_2$; or $R_5$ and $R_{5'}$ together with the atom to which they are bound optionally form a 3- to 6-membered ring having up to 2 heteroatoms selected from N, NH, O, S, SO, or $SO_2$; wherein the ring has up to 2 substituents selected independently from J;

$R_1$, $R_{1'}$, $R_{11}$, $R_{11'}$, $R_{13}$, and $R_{13'}$ are independently:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic,
(C5-C10)-heteroaryl-, or
(C5-C10)-heteroaryl-(C1-C12)-aliphatic-,
wherein each of $R_1$, $R_{1'}$, $R_{11}$, $R_{11'}$, $R_{13}$, and $R_{13'}$ is independently and optionally substituted with up to 3 substituents independently selected from J;
wherein any ring is optionally fused to a (C6-C10)aryl, (C5-C10)heteroaryl, (C3-C10)cycloalkyl, or (C3-C10) heterocyclyl;
wherein up to 3 aliphatic carbon atoms in each of $R_1$, $R_{1'}$, $R_{11}$, $R_{11'}$, $R_{13}$, and $R_{13'}$ may be replaced by a heteroatom selected from O, N, NH, S, SO, or $SO_2$ in a chemically stable arrangement; or $R_1$ and $R_{1'}$ together with the atom to which they are bound optionally form a 3- to 6-membered ring having up to 2 heteroatoms selected from N, NH, O, S, SO, or $SO_2$; wherein the ring system has up to 2 substituents selected independently from J; or $R_{11}$ and $R_{11'}$ together with the atom to which they are bound optionally form a 3- to 6-membered ring having up to 2 heteroatoms selected from N, NH, O, S, SO, or $SO_2$; wherein the ring has up to 2 substituents selected independently from J; or $R_{13}$ and $R_{13'}$ together with the atom to which they are bound is a 3- to 6-membered ring having up to 2 heteroatoms selected from N, NH, O, S, SO, or $SO_2$; wherein the ring has up to 2 substituents selected independently from J;

$R_2$, $R_4$, $R_8$, and $R_{12}$ are independently
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic,
(C5-C10)-heteroaryl-, or
(C5-C10)-heteroaryl-(C1-C12)-aliphatic-,
wherein each $R_2$, $R_4$, $R_8$, and $R_{12}$ is independently and optionally substituted with up to 3 substituents independently selected from J;
wherein up to two aliphatic carbon atoms in $R_2$, $R_4$, $R_8$, and $R_{12}$ may be replaced by a heteroatom selected from O, N, NH, S, SO, or $SO_2$; or $R_{11}$ and $R_{12}$ together with the atoms to which they are bound form a 3- to 20-membered mono-, a 4- to 20-membered bi-, or a 5- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or $R_{12}$ and $R_{13}$ together with the atoms to which they are bound form a 4- to a 20-membered mono-, a 5- to 20-membered bi-, or a 6- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or $R_{11}$ and $R_{13}$ together with the atoms to which they are bound form a 5- to a 20-membered mono-, a 6- to 20-membered bi-, or a 7- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or $R_{11}$, $R_{12}$, and $R_{13}$ together with the atoms to which they are bound form a 5- to 20-membered bi-, or a 6- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or $R_{13'}$ and $R_2$ together with the atoms to which they are bound form a 3- to a 20-membered mono-, a 4- to 20-membered bi-, or a 5- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and wherein said ring has up to 3 substituents selected independently from J; or R$_5$ and R$_{13}$ together with the atoms to which they are bound form a 18- to a 23-membered mono-, a 19- to 24-membered bi-, or a 20- to 25-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and SO$_2$;
wherein each ring is optionally fused to a (C6-C10)aryl, (C5-C10)heteroaryl, (C3-C10)cycloalkyl, or (C3-C10)heterocyclyl; and
wherein said ring has up to 6 substituents selected independently from J; or R$_1$ and R$_{12}$ together with the atoms to which they are bound form a 18- to a 23-membered mono-, a 19- to 24-membered bi-, or a 20- to 25-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and SO$_2$;
wherein each ring is optionally fused to a (C6-C10)aryl, (C5-C10)heteroaryl, (C3-C10)cycloalkyl, or (C3-C10)heterocyclyl; and
wherein said ring has up to 6 substituents selected independently from J.

In another embodiment, the present invention provides a compound of formula II:

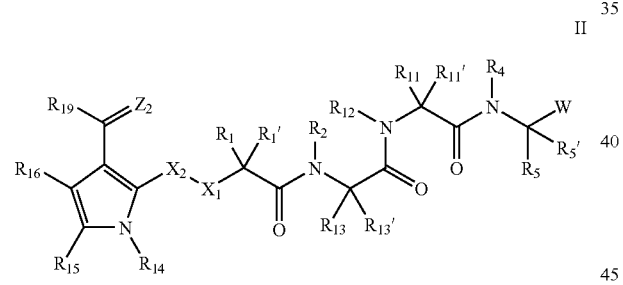

II or a pharmaceutically acceptable salt or mixtures thereof, wherein:
X$_1$ is —N(R$_{20}$)—, —O—, —S—, or —C(R')$_2$—;
X$_2$ is —C(O)—, —C(S)—, —S(O)—, or —S(O)$_2$—;
W is:

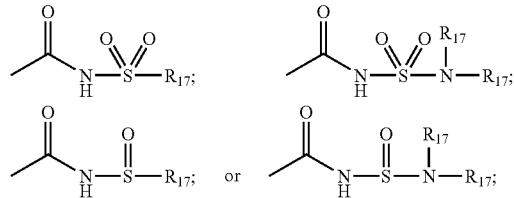

wherein each R$_{17}$ is independently:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)-aliphatic-,
(C5-C10)heteroaryl-, or
(C5-C10)heteroaryl-(C1-C12)-aliphatic-, or
two R$_{17}$ groups, which are bound to the same nitrogen atom, form together with that nitrogen atom, a (C3-C10)-membered heterocyclic ring having in addition to the nitrogen up to 2 additional heteroatoms selected from N, NH, O, S, SO, and SO$_2$;
wherein R$_{17}$ is optionally substituted with up to 3 J substituents;
each R$_{18}$ is independently —OR'; or both OR' groups together with the boron atom, is a (C5-C20)-membered heterocyclic ring having in addition to the boron up to 3 additional heteroatoms selected from N, NH, O, S, SO, and SO$_2$, wherein the ring is monocyclic or bicyclic, wherein the bicyclic ring, if present, is linearly fused, bridged, or spirocyclic.
R$_5$ is (C1-C12)-aliphatic, wherein any hydrogen is optionally replaced with halogen, and wherein any terminal carbon atom of R$_5$ is optionally substituted with sulfhydryl or hydroxy;
R$_5$ is hydrogen or (C1-C12)-aliphatic, wherein any hydrogen is optionally replaced with halogen, and wherein any terminal carbon atom of R$_5$ is optionally substituted with sulfhydryl or hydroxy; or
R$_5$ and R5' together with the atom to which they are bound is a 3- to 6-membered ring having up to 2 heteroatoms selected from N, NH, O, S, SO, or SO$_2$; wherein the ring has up to 2 substituents selected independently from J;
R$_1$, R$_1'$, R$_{11}$, R$_{11'}$, R$_{13}$, and R$_{13'}$ are independently:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic,
(C5-C10)-heteroaryl-, or
(C5-C10)-heteroaryl-(C1-C12)-aliphatic-; or
R$_1$ and R$_{1'}$ together with the atom to which they are bound is a 3- to 6-membered ring having up to 2 heteroatoms selected from N, NH, O, S, SO, or SO$_2$; wherein the ring has up to 2 substituents selected independently from J; or
R$_{11}$ and R$_{11'}$ together with the atom to which they are bound is a 3- to 6-membered ring having up to 2 heteroatoms selected from N, NH, O, S, SO, or SO$_2$; wherein the ring has up to 2 substituents selected independently from J; or
R$_{13}$ and R$_{13'}$ together with the atom to which they are bound is a 3- to 6-membered ring having up to 2 heteroatoms selected from N, NH, O, S, SO, or SO$_2$; wherein the ring has up to 2 substituents selected independently from J;
wherein each of R$_1$, R$_{1'}$, R$_{11}$, R$_{11'}$, R$_{13}$, and R$_{13'}$ is independently and optionally substituted with up to 3 substituents independently selected from J; and wherein any ring is optionally fused to a (C6-C10) aryl, (C5-C10)heteroaryl, (C3-C10)cycloalkyl, or (C3-C10)heterocyclyl; and wherein up to 3 aliphatic carbon atoms in each of R$_1$, R$_{1'}$, R$_{11}$, R$_{11'}$, R$_{13}$, and $R_{13'}$ may be replaced by a heteroatom selected from O, N, NH, S, SO, or $SO_2$ in a chemically stable arrangement;

$R_2$, $R_4$, $R_{12}$, and $R_{20}$ are independently
hydrogen-,
(C1-C12)-aliphatic-,
(C3-C10)-cycloalkyl-,
(C3-C10)-cycloalkyl-(C1-C12)-aliphatic-, or
(C6-C10)aryl-(C1-C12)-aliphatic-,
  wherein each $R_2$, $R_4$, $R_{12}$, and $R_{20}$ is independently and optionally substituted with up to 3 substituents independently selected from J;
  wherein up to two aliphatic carbon atoms in $R_2$, $R_4$, $R_{12}$, and $R_{20}$ may be replaced by a heteroatom selected from O, N, NH, S, SO, or $SO_2$; or $R_{11}$ and $R_{12}$ together with the atoms to which they are bound form a 3- to a 20-membered mono-, a 4- to 20-membered bi-, or a 5- to 20-membered tri-cyclic carbocyclic or heterocyclic ring system;
  wherein, in the bi- and tri-cyclic ring system, each ring is linearly fused, bridged, or spirocyclic;
  wherein each ring is either aromatic or nonaromatic;
  wherein each heteroatom in the heterocyclic ring system is selected from the group consisting of N, NH, O, SO, and $SO_2$;
  wherein each ring is optionally fused to a (C6-C10)aryl, (C5-C10)heteroaryl, (C3-C10)cycloalkyl, or (C3-C10)heterocyclyl; and
  wherein said ring has up to 3 substituents selected independently from J; or $R_{12}$ and $R_{13}$ together with the atoms to which they are bound form a 4- to a 20-membered mono-, a 5- to 20-membered bi-, or a 6- to 20-membered tri-cyclic carbocyclic or heterocyclic ring system;
  wherein, in the bi- and tri-cyclic ring system, each ring is linearly fused, bridged, or spirocyclic;
  wherein each ring is either aromatic or nonaromatic;
  wherein each heteroatom in the heterocyclic ring system is selected from the group consisting of N, NH, O, S, SO, and $SO_2$;
  wherein each ring is optionally fused to a (C6-C10)aryl, (C5-C10)heteroaryl, (C3-C10)cycloalkyl, or (C3-C10)heterocyclyl; and
  wherein said ring has up to 3 substituents selected independently from J; or $R_{11}$ and $R_{13}$ together with the atoms to which they are bound form a 5- to a 20-membered mono-, a 6- to 20-membered bi-, or a 7- to 20-membered tri-cyclic carbocyclic or heterocyclic ring system;
  wherein, in the bi- and tri-cyclic ring system, each ring is linearly fused, bridged, or spirocyclic;
  wherein each ring is either aromatic or nonaromatic;
  wherein each heteroatom in the heterocyclic ring system is selected from the group consisting of N, NH, O, S, SO, and $SO_2$;
  wherein each ring is optionally fused to a (C6-C10)aryl, (C5-C10)heteroaryl, (C3-C10)cycloalkyl, or (C3-C10)heterocyclyl; and
  wherein said ring has up to 3 substituents selected independently from J; or $R_{11}$, $R_{12}$, and $R_{13}$ together with the atoms to which they are bound form a 5- to 20-membered bi-, or a 6- to 20-membered tri-cyclic carbocyclic or heterocyclic ring system;
  wherein, in the bi- and tri-cyclic ring system, each ring is linearly fused, bridged, or spirocyclic;
  wherein each ring is either aromatic or nonaromatic;
  wherein each heteroatom in the heterocyclic ring system is selected from the group consisting of N, NH, O, S, SO, and $SO_2$;
  wherein each ring is optionally fused to a (C6-C10)aryl, (C5-C10)heteroaryl, (C3-C10)cycloalkyl, or (C3-C10)heterocyclyl; and
  wherein said ring has up to 3 substituents selected independently from J; or $R_{13'}$ and $R_2$ together with the atoms to which they are bound form a 3- to a 20-membered mono-, a 4- to 20-membered bi-, or a 5- to 20-membered tri-cyclic carbocyclic or heterocyclic ring system;
  wherein, in the bi- and tri-cyclic ring system, each ring is linearly fused, bridged, or spirocyclic;
  wherein each ring is either aromatic or nonaromatic;
  wherein each heteroatom in the heterocyclic ring system is selected from the group consisting of N, NH, O, S, SO, and $SO_2$;
  wherein each ring is optionally fused to a (C6-C10)aryl, (C5-C10)heteroaryl, (C3-C10)cycloalkyl, or (C3-C10)heterocyclyl; and
  wherein said ring has up to 3 substituents selected independently from J;

$R_{14}$ is —H, —S(O)R', —S(O)$_2$R', —C(O)R', —C(O)OR', —C(O)N(R')$_2$, —N(R')C(O)R', —N(COR')COR', —SO$_2$N(R')$_2$, —SO$_3$R', —C(O)C(O)R', —C(O)CH$_2$C(O)R', —C(S)R', —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');

$R_{15}$ and $R_{16}$ are independently halogen, —OR', —OC(O)N(R')$_2$, —NO$_2$, —CN, —CF$_3$, —OCF$_3$, —R', oxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');

$Z_2$ is =O, =NR', =NOR', or =C(R')$_2$;

$R_{19}$ is —OR', —CF$_3$, —OCF$_3$, —R', —N(R')$_2$, —SR', —C(O)R', —COOR'—CON(R')$_2$, —N(R')COR', or —N(COR')COR';

J is halogen, —OR', —OC(O)N(R')$_2$, —NO$_2$, —CN, —CF$_3$, —OCF$_3$, —R', oxo, thioxo, 1,2-methylenedioxy, 1,2-ethyenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');

wherein:
two R' groups together with the atoms to which they are bound form a 3- to 10-membered aromatic or non-aromatic ring having up to 3 heteroatoms independently selected from N, NH, O, S, SO, or SO₂, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from J₂; or each R' is independently selected from:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, or
(C5-C10)-heteroaryl-(C1-C12)-aliphatic-;
wherein R' has up to 3 substituents selected independently from J₂; and J₂ is halogen, —OR', —OC(O)N(R')₂, —NO₂, —CN, —CF₃, —OCF₃, —R', oxo, thioxo, 1,2-methylenedioxy, 1,2-ethylenedioxy, —N(R')₂, —SR', —SOR', —SO₂R', —SO₂N(R')₂, —SO₃R', —C(O)R', —C(O)C(O)R', —C(O)CH₂C(O)R', —C(S)R', —C(O)OR', —OC(O)R', —C(O)N(R')₂, —OC(O)N(R')₂, —C(S)N(R')₂, —(CH₂)₀₋₂NHC(O)R', —N(R')N(R')COR', —N(R')N(R')C(O)OR', —N(R')N(R')CON(R')₂, —N(R')SO₂R', —N(R')SO₂N(R')₂, —N(R')C(O)OR', —N(R')C(O)R', —N(R')C(S)R', —N(R')C(O)N(R')₂, —N(R')C(S)N(R')₂, —N(COR')COR', —N(OR')R', —CN, —C(=NH)N(R')₂, —C(O)N(OR')R', —C(=NOR')R', —OP(O)(OR')₂, —P(O)(R')₂, —P(O)(OR')₂, or —P(O)(H)(OR').

In another embodiment, the present invention provides a compound of formula IV:

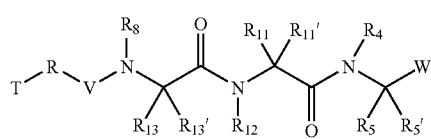

IV or a pharmaceutically acceptable salt or mixtures thereof, wherein:
V is —C(O)—, —S(O)—, —C(R')₂— or —S(O)₂—;
R is —C(O)—, —S(O)—, —S(O)₂—, —N(R₈)—, —O—, or a bond;
T is:
(C6-C10)-aryl,
(C6-C10)-aryl-(C1-C12)aliphatic,
(C1-C12)-aliphatic-,
(C3-C10)-cycloalkyl or -cycloalkenyl,
[(C3-C10)-cycloalkyl or -cycloalkenyl]-(C1-C12)-aliphatic,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic;
wherein up to 3 aliphatic carbon atoms in T may be optionally replaced with —S—, —S(O)—, —S(O)₂—, —O—, —N—, or —N(H)—, in a chemically stable arrangement;

wherein each T may be optionally substituted with up to 3 J substituents;

J is halogen, —OR', —OC(O)N(R')₂, —NO₂, —CN, —CF₃, —OCF₃, —R', oxo, thioxo, 1,2-methylenedioxy, 1,2-ethylenedioxy, —N(R')₂, —SR', —SOR', —SO₂R', —SO₂N(R')₂, —SO₃R', —C(O)R', —C(O)C(O)R', —C(O)CH₂C(O)R', —C(S)R', —C(O)OR', —OC(O)R', —C(O)N(R')₂, —OC(O)N(R')₂, —C(S)N(R')₂, —(CH₂)₀₋₂NHC(O)R', —N(R')N(R')COR', —N(R')N(R')C(O)OR', —N(R')N(R')CON(R')₂, —N(R')SO₂R', —N(R')SO₂N(R')₂, —N(R')C(O)OR', —N(R')C(O)R', —N(R')C(S)R', —N(R')C(O)N(R')₂, —N(R')C(S)N(R')₂, —N(COR')COR', —N(OR')R', —C(=NH)N(R')₂, —C(O)N(OR')R', —C(=NOR')R', —OP(O)(OR')₂, —P(O)(R')₂, —P(O)(OR')₂, or —P(O)(H)(OR'), wherein;

two R' groups together with the atoms to which they are bound form a 3- to 10-membered aromatic or non-aromatic ring system having up to 3 heteroatoms independently selected from N, NH, O, S, SO, or SO₂, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from J₂;

each R' is independently selected from:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, or
(C5-C10)-heteroaryl-(C1-C12)-aliphatic-,
wherein R' has up to 3 substituents selected independently from J₂;

J₂ is halogen, —OR', —OC(O)N(R')₂, —NO₂, —CN, —CF₃, —OCF₃, —R', oxo, thioxo, 1,2-methylenedioxy, —N(R')₂, —SR', —SOR', —SO₂R', —SO₂N(R')₂, —SO₃R', —C(O)R', —C(O)C(O)R', —C(O)CH₂C(O)R', —C(S)R', —C(O)OR', —OC(O)R', —C(O)N(R')₂, —OC(O)N(R')₂, —C(S)N(R')₂, —(CH₂)₀₋₂NHC(O)R', —N(R')N(R')COR', —N(R')N(R')C(O)OR', —N(R')N(R')CON(R')₂, —N(R')SO₂R', —N(R')SO₂N(R')₂, —N(R')C(O)OR', —N(R')C(O)R', —N(R')C(S)R', —N(R')C(O)N(R')₂, —N(R')C(S)N(R')₂, —N(COR')COR', —N(OR')R', —C(=NH)N(R')₂, —C(O)N(OR')R', —C(=NOR')R', —OP(O)(OR')₂, —P(O)(R')₂, —P(O)(OR')₂, or —P(O)(H)(OR'); or T is:

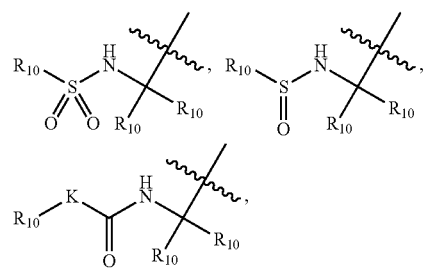

-continued

[chemical structures]

wherein:
R$_{10}$ is:
hydrogen,
(C1-C12)-aliphatic,
(C6-C10)-aryl,
(C6-C10)-aryl- (C1-C12)aliphatic,
(C3-C10)-cycloalkyl or -cycloalkenyl,
[(C3-C10)-cycloalkyl or -cycloalkenyl]-(C1-C12)-aliphatic,
(C3-C10)-heterocyclyl,
(C3-C10)-heterocyclyl-(C1-C12)-aliphatic,
(C5-C10)-heteroaryl, or
(C5-C10)-heteroaryl-(C1-C12)-aliphatic,
K is a bond, (C1-C12)-aliphatic, —O—, —S—, —NR$_9$—, —C(O)—, or —C(O)—NR$_9$—, wherein R$_9$ is hydrogen or (C1-C12)-aliphatic;
n is 1-3; or
T is selected from N(R$_{17}$)$_2$;
W is:

[chemical structures]

wherein each R$_{17}$ is independently:
hydrogen-,
(C1-C12)-aliphatic-,
(C3-C10)-cycloalkyl- or cycloalkenyl-,
[(C3-C10)-cycloalkyl- or cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)-aliphatic-,
(C5-C10)heteroaryl-, or
(C5-C10)heteroaryl-(C1-C12)-aliphatic-, or
wherein two R$_{17}$ groups, which are bound to the same nitrogen atom, together with that nitrogen atom, optionally form a (C3-C10)-membered saturated or partially unsaturated heterocyclic ring system having in addition to the nitrogen up to 2 additional heteroatoms selected from N, NH, O, S, SO, and SO$_2$ and wherein said ring is optionally substituted with up to 3 J substituents;
wherein R$_{17}$ is optionally substituted with up to 3 J substituents;
R$_5$ and R$_{5'}$ are independently hydrogen or (C1-C12)-aliphatic, wherein any hydrogen is optionally replaced with halogen, and wherein any terminal carbon atom is optionally substituted with sulfhydryl or hydroxy, and wherein up to two aliphatic carbon atoms may be replaced by a heteroatom selected from N, NH, O, S, SO, or SO$_2$; or
R$_5$ and R$_{5'}$ together with the atom to which they are bound optionally form a 3- to 6-membered ring having up to 2 heteroatoms selected from N, NH, O, S, SO, or SO$_2$; wherein the ring has up to 2 substituents selected independently from J;
R$_{11}$, R$_{11'}$, R$_{13}$, and R$_{13'}$ are independently:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic,
(C5-C10)-heteroaryl-, or
(C5-C10)-heteroaryl-(C1-C12)-aliphatic-,
wherein each of R$_{11}$, R$_{11'}$, R$_{13}$, and R$_{13'}$ is independently and optionally substituted with up to 3 substituents independently selected from J;

wherein any ring is optionally fused to a (C6-C10)aryl, (C5-C10)heteroaryl, (C3-C10)cycloalkyl, or (C3-C10) heterocyclyl;
wherein up to 3 aliphatic carbon atoms in each of $R_{11}$, $R_{11'}$, $R_{13}$, and $R_{13'}$ may be replaced by a heteroatom selected from O, N, NH, S, SO, or $SO_2$ in a chemically stable arrangement; or
$R_{11}$ and $R_{11'}$ together with the atom to which they are bound optionally form a 3- to 6-membered ring having up to 2 heteroatoms selected from N, NH, O, S, SO, or $SO_2$; wherein the ring has up to 2 substituents selected independently from J; or
$R_{13}$ and $R_{13'}$ together with the atom to which they are bound is a 3- to 6-membered ring having up to 2 heteroatoms selected from N, NH, O, S, SO, or $SO_2$; wherein the ring has up to 2 substituents selected independently from J;
$R_4$, $R_8$, and $R_{12}$ are independently
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic,
(C5-C10)-heteroaryl-, or
(C5-C10)-heteroaryl-(C1-C12)-aliphatic-,
wherein each $R_4$, $R_8$, and $R_{12}$ is independently and optionally substituted with up to 3 substituents independently selected from J;
wherein up to two aliphatic carbon atoms in $R_4$, $R_8$, and $R_{12}$ may be replaced by a heteroatom selected from O, N, NH, S, SO, or $SO_2$; or
$R_{11}$ and $R_{12}$ together with the atoms to which they are bound form a 3- to 20-membered mono-, a 4- to 20-membered bi-, or a 5- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or
$R_{12}$ and $R_{13}$ together with the atoms to which they are bound form a 4- to 20-membered mono-, a 5- to 20-membered bi-, or a 6- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or $R_{11}$ and $R_{13}$ together with the atoms to which they are bound form a 5- to a 20-membered mono-, a 6- to 20-membered bi-, or a 7- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or
$R_{11}$, $R_{12}$, and $R_{13}$ together with the atoms to which they are bound form a 5- to a 20-membered bi-, or a 6- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or
$R_{13'}$ and $R_8$ together with the atoms to which they are bound form a 3- to 20-membered mono-, a 4- to 20-membered bi-, or a 5- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 3 substituents selected independently from J; or
$R_5$ and $R_{13}$ together with the atoms to which they are bound form a 18- to a 23-membered mono-, a 19- to 24-membered bi-, or a 20- to 25-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 6 substituents selected independently from J; or
when $R_5$ and $R_{5'}$ together with the atom to which they are bound form an optionally substituted 3- to 6-membered ring having up to 2 heteroatoms selected from N, NH, O, S, SO, or $SO_2$, then one of the substitutable atoms in said ring is taken together with $R_{13}$ and the atom to which $R_{13}$ is bound to form a 14- to a 19-membered mono-, a 19- to 24-membered bi-, or a 20- to 25-membered tri-cyclic carbocyclic or heterocyclic ring system;

wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10) heterocyclyl; and
wherein said ring has up to 6 substituents selected independently from J.

In another embodiment, the present invention provides compounds of formula I other than compounds of formula II.

Definitions

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin. It is understood that as used herein, the term "(C6-C10)-aryl-" includes any one of a C6, C7, C8, C9, and C10 monocyclic or bicyclic carbocyclic aromatic ring system.

The term "heterocyclyl" as used herein means a monocyclic or bicyclic non-aromatic ring system having 1 to 3 heteroatom or heteroatom groups in each ring selected from O, N, NH, S, SO, or $SO_2$ in a chemically stable arrangement. In a bicyclic non-aromatic ring system embodiment of "heterocyclyl" one or both rings may contain said heteroatom or heteroatom groups. It is understood that as used herein, the term "(C5-C10)-heterocyclyl-" includes any one of a 5, 6, 7, 8, 9, and 10 atom monocyclic or bicyclic non-aromatic ring system having 1 to 3 heteroatoms or heteroatom groups in each ring selected from O, N, NH, and S in a chemically stable arrangement.

Heterocyclic rings include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroaryl" as used herein means a monocyclic or bicyclic aromatic ring system having 1 to 3 heteroatom or heteroatom groups in each ring selected from O, N, NH or S in a chemically stable arrangement. In such a bicyclic aromatic ring system embodiment of "heteroaryl":
one or both rings may be aromatic; and
one or both rings may contain said heteroatom or heteroatom groups. It is understood that as used herein, the term "(C5-C10)-heteroaryl-" includes any one of a 5, 6, 7, 8, 9, and 10 atom monocyclic or bicyclic aromatic ring system having 1 to 3 heteroatoms or heteroatom groups in each ring selected from O, N, NH, and S in a chemically stable arrangement.

Heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl). Each of the above aryl, heterocyclyl or heteroaryl above may contain up to 3 substituents independently selected from, for example, halogen, —OR', —$NO_2$, —$CF_3$, —$OCF_3$, —R', oxo, —OR', —O-benzyl, —O-phenyl, 1,2-methylenedioxy, 1,2-ethylenedioxy, —N(R')$_2$, —C(O)R', —COOR' or —CON(R')$_2$, wherein R' is independently selected from H, (C1-C6)-alkyl, (C2-C6)-alkenyl or alkynyl.

The term "aliphatic" as used herein means a straight chained or branched alkyl, alkenyl or alkynyl. It is understood that as used herein, the term "(C1-C12)-aliphatic-" includes any one of a C1, C2, C3, C4, C5, C6, C7, C8, C9, C10, C11, and C12 straight or branched alkyl chain of carbon atoms. It is understood that alkenyl or alkynyl embodiments need at least two carbon atoms in the aliphatic chain. The term "cycloalkyl or cycloalkenyl" refers to a monocyclic or fused or bridged bicyclic carbocyclic ring system that is not aromatic. Cycloalkenyl rings have one or more units of unsaturation. It is also understood that as used herein, the term "(C3-C10)-cycloalkyl- or -cycloalkenyl-" includes any one of a C3, C4, C5, C6, C7, C8, C9, and C10 monocyclic or fused or bridged bicyclic carbocyclic ring. Cycloalkyl groups include, but are not limited to, cyclopropyl, cyclobutyl, cyclopentyl, cyclohexyl, cyclohexenyl, cycloheptyl, cycloheptenyl, nornbornyl, adamantyl and decalin-yl.

As used herein, the carbon atom designations may have the indicated integer and any intervening integer. For example, the number of carbon atoms in a (C1-C4)-alkyl group is 1, 2, 3, or 4. It should be understood that these designation refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

The phrase "chemically stable arrangement" as used herein refers to a compound structure that renders the compound sufficiently stable to allow manufacture and administration to a mammal by methods known in the art. Typically, such compounds are stable at a temperature of 400° C. or less, in the absence of moisture or other chemically reactive condition, for at least a week.

In another embodiment, the present invention provides compounds of formula III, wherein $P_1$, $P_2$, $P_3$, $P_4$ designate the residues of a serine protease inhibitor as known to those skilled in the art, m is 1 or 2, U is a bond or $NR_{17}$, and V, R, T, and $R_{17}$, are as defined in any of the embodiments herein.

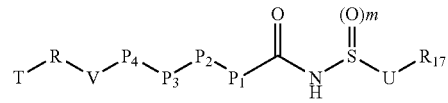

III

In another embodiment, the present invention provides compounds of formula IIIa, wherein $P_1$, $P_2$, and $P_3$ designate the residues of a serine protease inhibitor as known to those skilled in the art, m is 1 or 2, U is a bond or $NR_{17}$, and V, R, T, and $R_{17}$, are as defined in any of the embodiments herein.

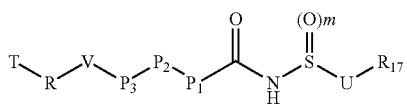

IIIa

All compounds, therefore, having: 1) structural elements of a serine protease inhibitor; and 2) the acyl sulfonamide-moiety are considered part of this invention. Compounds having the structural elements of a serine protease inhibitor include, but are not limited to, the compounds of the following publications: WO 97/43310, US 20020016294, WO 01/81325, WO 02/08198, WO 01/77113, WO 02/08187, WO 02/08256, WO 02/08244, WO 03/006490, WO 01/74768, WO 99/50230, WO 98/17679, WO 02/48157, US 20020177725, WO 02/060926, US 20030008828, WO 02/48116, WO 01/64678, WO 01/07407, WO 98/46630, WO 00/59929, WO 99/07733, WO 00/09588, US 20020016442, WO 00/09543, WO 99/07734, U.S. Pat. No. 6,018,020, WO 98/22496, U.S. Pat. No. 5,866,684, WO 02/079234, WO 00/31129, WO 99/38888, WO 99/64442, WO 2004072243, and WO 02/18369, which are incorporated herein by reference.

Thus, any compound of the above publications may be modified to have this acyl sulfonamide moiety, or derivatives thereof. Any such compound is part of this invention. For example, compound A in WO 02/18369 (p. 41):

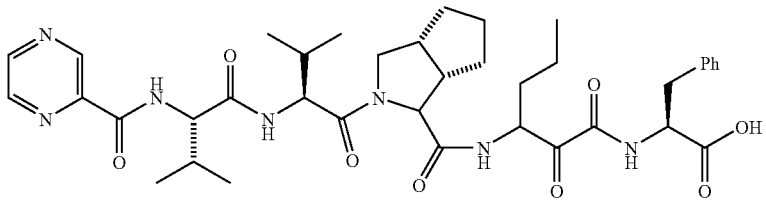

may be modified to provide the following compound of this invention:

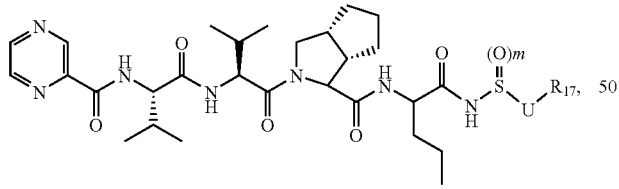

wherein m is 1 or 2, U is a bond or $NR_{17}$, and $R_{17}$ is as defined in any of the embodiments herein.

According to one embodiment of compounds of formula I, formula II, or formula IV;

$R_{11}$ is H; and $R_{12}$ is
  (C1-C6)-alkyl,
  (C3-C10)-cycloalkyl,
  [(C3-C10)-cycloalkyl]-(C1-C12)-alkyl,
  (C6-C10)-aryl,
  (C6-C10)-aryl-(C1-C6)alkyl,
  (C3-C10)-heterocyclyl,
  (C6-C10)-heterocyclyl-(C1-C6)alkyl,
  (C5-C10)-heteroaryl, or
  (C5-C10)-heteroaryl-(C1-C6)-alkyl.

According to another embodiment of compounds of formula I, formula II, or formula IV, $R_{12}$ is isobutyl, cyclohexyl, cyclohexylmethyl, benzyl, or phenylethyl.

According to another embodiment of compounds of formula I, formula II, or formula IV, $R_{11}$ is:
  (C1-C6)-alkyl,
  (C3-C10)-cycloalkyl,
  [(C3-C10)-cycloalkyl]-(C1-C12)-alkyl,
  (C6-C10)-aryl,
  (C6-C10)-aryl-(C1-C6)alkyl;
  (C3-C10)-heterocyclyl,
  (C6-C10)-heterocyclyl-(C1-C6)alkyl,
  (C5-C10)-heteroaryl, or
  (C5-C10)-heteroaryl-(C1-C6)-alkyl; and $R_{12}$ is H.

According to another embodiment of compounds of formula I, formula II, or formula IV, $R_{11}$, and $R_{12}$ are H.

According to another embodiment of compounds of formula I, formula II, or formula IV, the

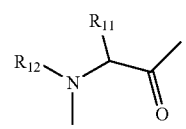

radical is:

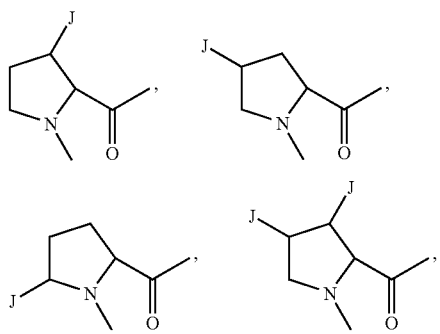

According to another embodiment of compounds of formula I, formula II, or formula IV, the
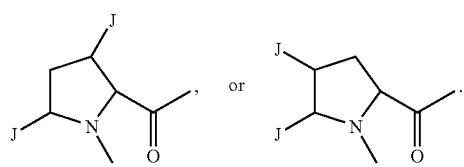
radical is:

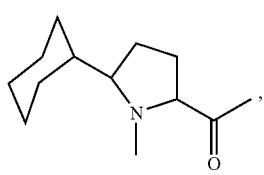
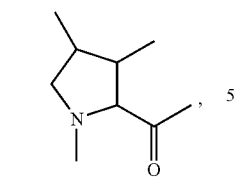
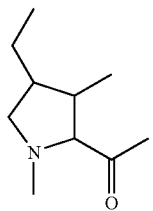
or
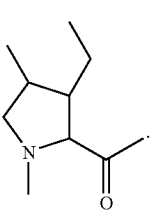
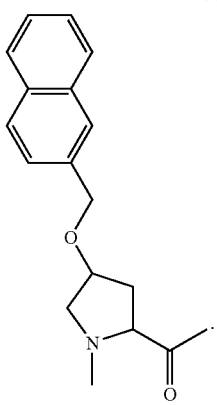
According to another embodiment of compounds of formula I, formula II, or formula IV, the
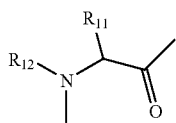
radical is:
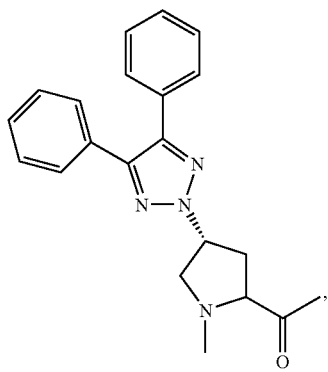
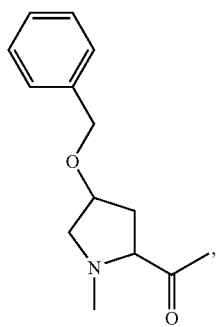
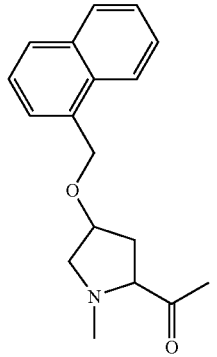
or
According to another embodiment of compounds of formula I, formula II, or formula IV, the
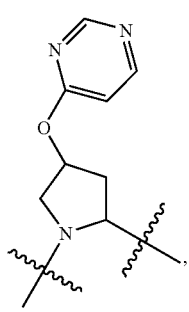
radical is:
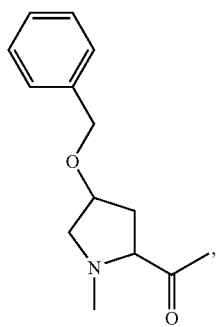
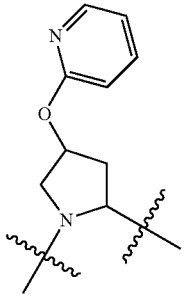
or
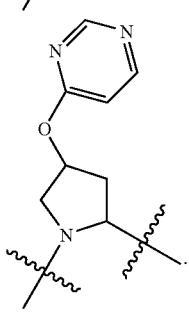

According to another embodiment of compounds of formula I, formula II, or formula IV, the
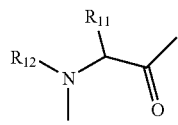
radical is:
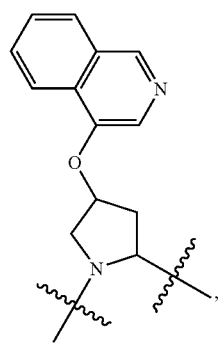
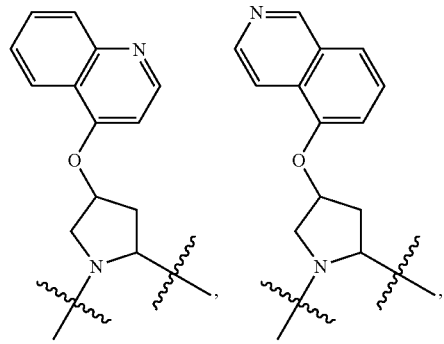
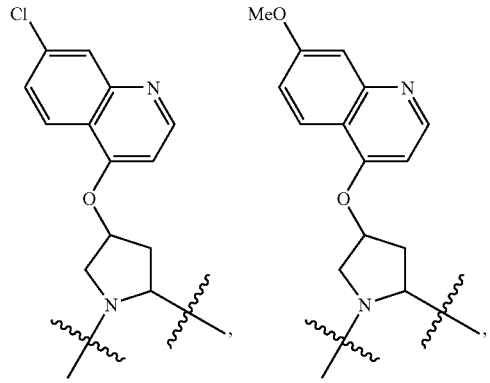
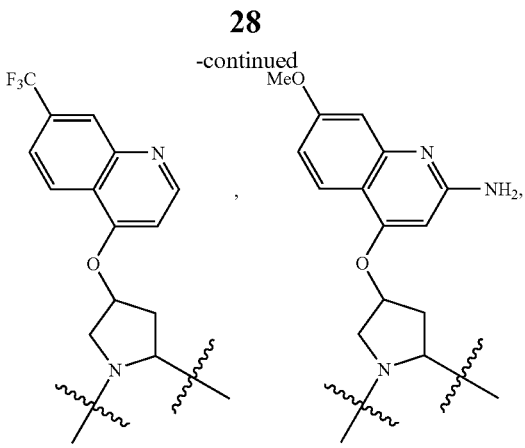
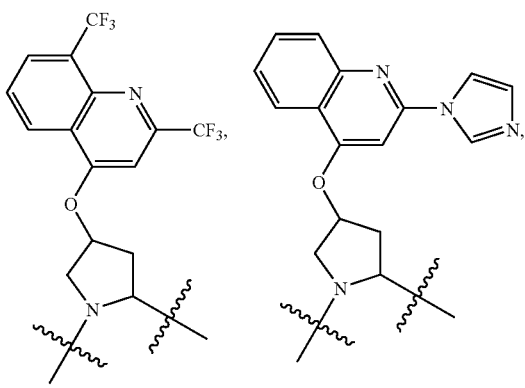
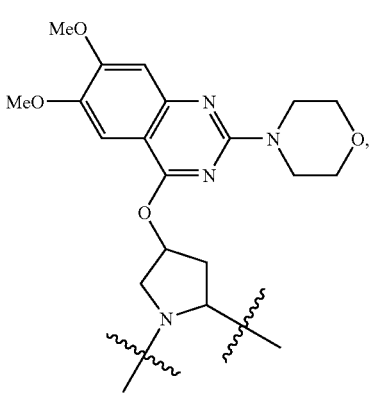
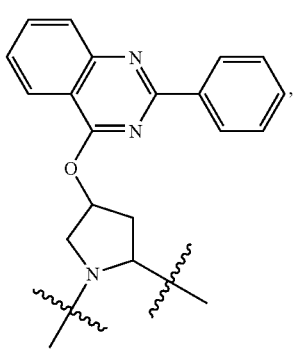

-continued
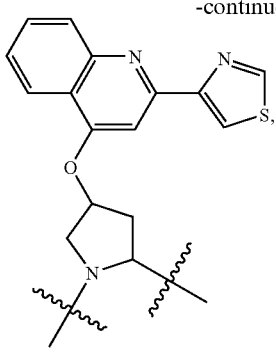
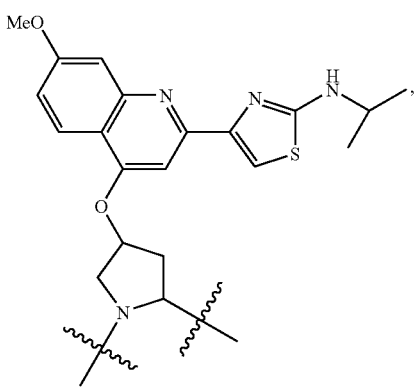
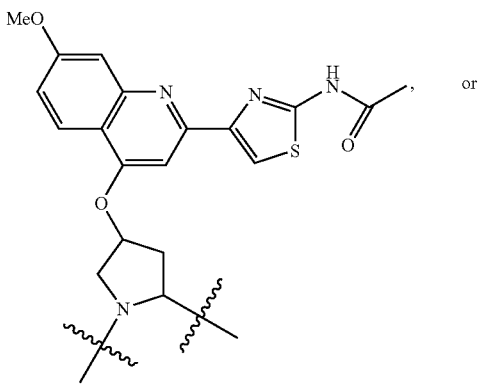
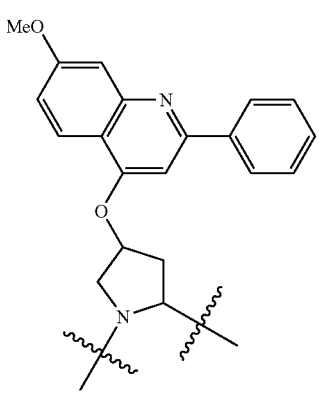
According to another embodiment of compounds of formula I, formula II, or formula IV, the
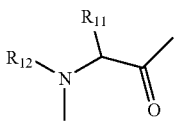
radical is:
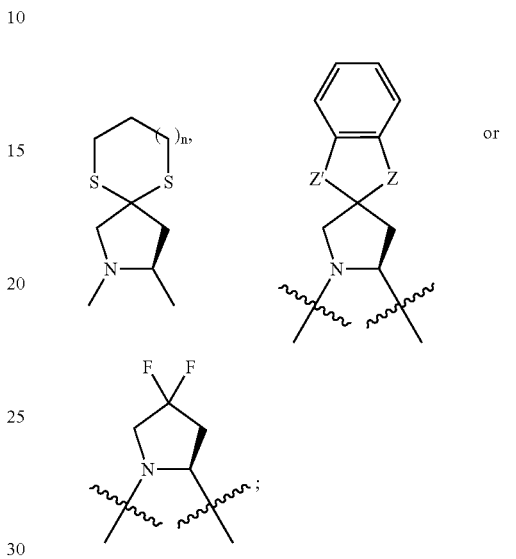
wherein n is 0 or 1 and Z and Z' are S or O.
According to another embodiment of compounds of formula I, formula II, or formula IV, the
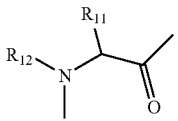
radical is:
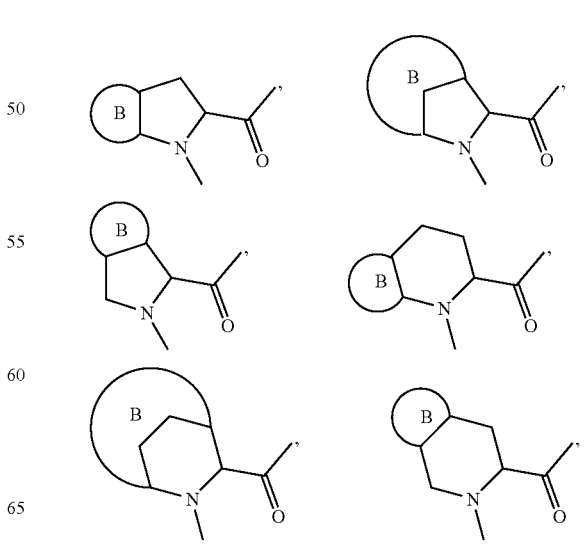

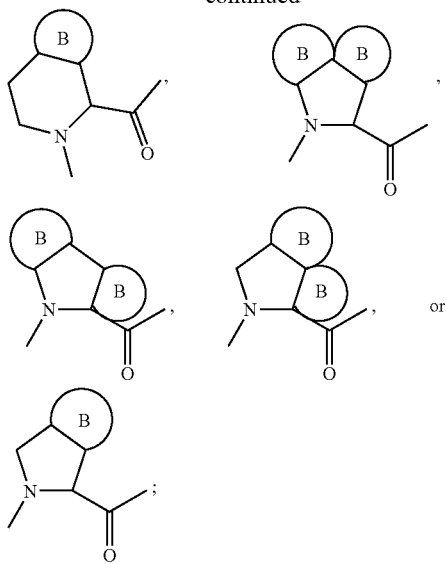

wherein each B independently forms a 3- to a 20-membered carbocyclic or heterocyclic ring system;
wherein each ring B is either aromatic or nonaromatic;
wherein each heteroatom in the heterocyclic ring system is N, NH, O, S, SO, or $SO_2$;
wherein, in the bi- and tri-cyclic ring system, each ring is linearly fused, bridged, or spirocyclic;
wherein each ring is optionally fused to a (C6-C10)aryl, (C5-C10)heteroaryl, (C3-C10)cycloalkyl, or (C3-C10)heterocyclyl; and
wherein each ring is optionally substituted with up to 3 substituents selected independently from J.

According to another embodiment of compounds of formula I, formula II, or formula IV, ring systems are:

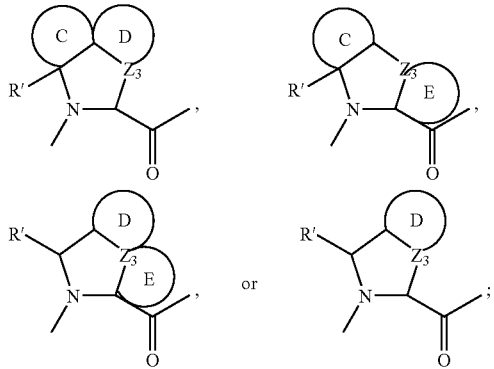

wherein each ring C, D, and E are as defined above for ring B and $Z_3$ is a carbon atom, —CHR'—N—, —HN—CR'— or —CHR'—CHR'—, —O—CHR'—, —S—CHR'—, —SO—CHR'—, —$SO_2$—CHR'—, or —N—. In another embodiment, R' is (C1-C12)-aliphatic, (C6-C10)-aryl, (C6-C10)aryl-(C1-C12)-aliphatic, or (C3-C10)-cycloalkyl. In another embodiment R' is (C1-C6)-alkyl or (C3-C7)-cycloalkyl.

According to another embodiment of compounds of formula I, formula II, or formula IV, ring C is selected from:

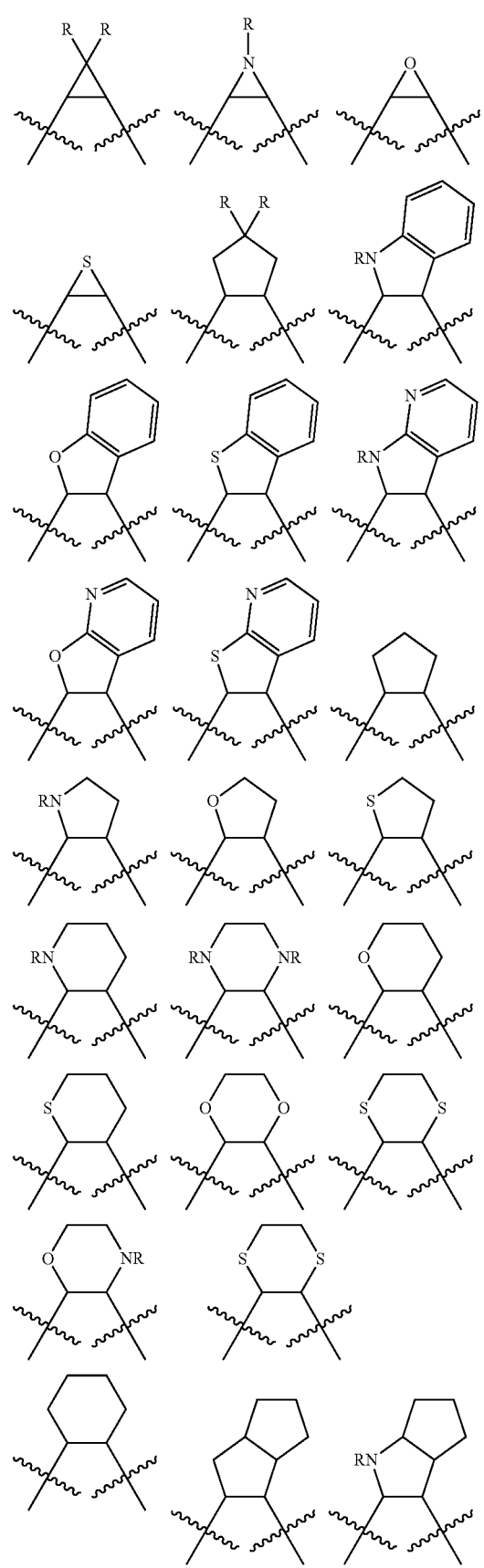

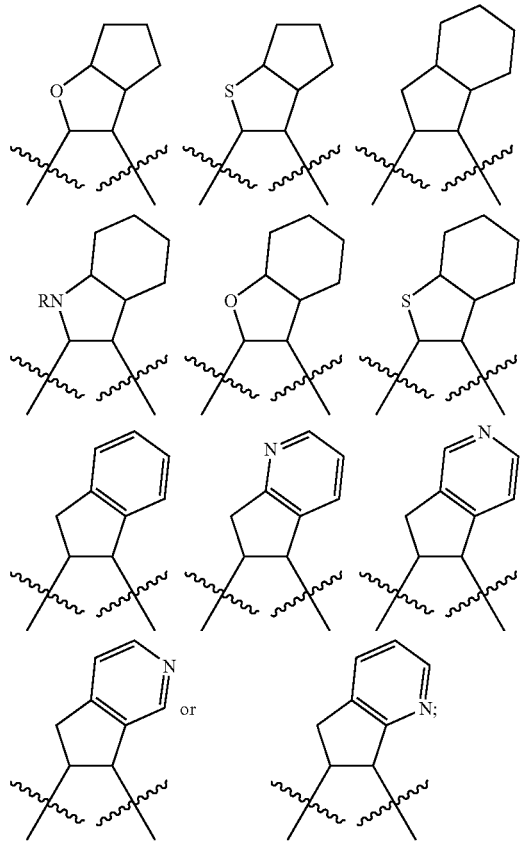

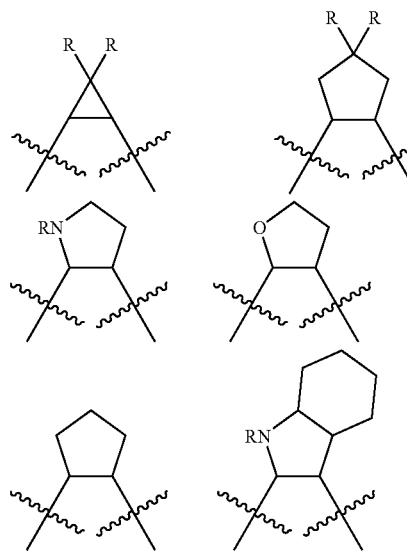

wherein R is:
(C1-C12)-aliphatic-,
(C3-C10)-cycloalkyl or -cycloalkenyl-,
(C6-C10)-aryl-, or
(C6-C10)-aryl-(C1-C12)aliphatic-.

According to another embodiment of compounds of formula I, formula II, or formula IV, ring C is selected from:

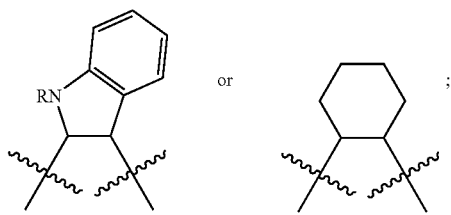

wherein R is:
(C1-C12)-aliphatic-,
(C3-C10)-cycloalkyl or -cycloalkenyl-,
(C6-C10)-aryl-, or
(C6-C10)-aryl-(C1-C12)aliphatic-.

According to another embodiment of compounds of formula I, formula II, or formula IV, ring D is selected from:

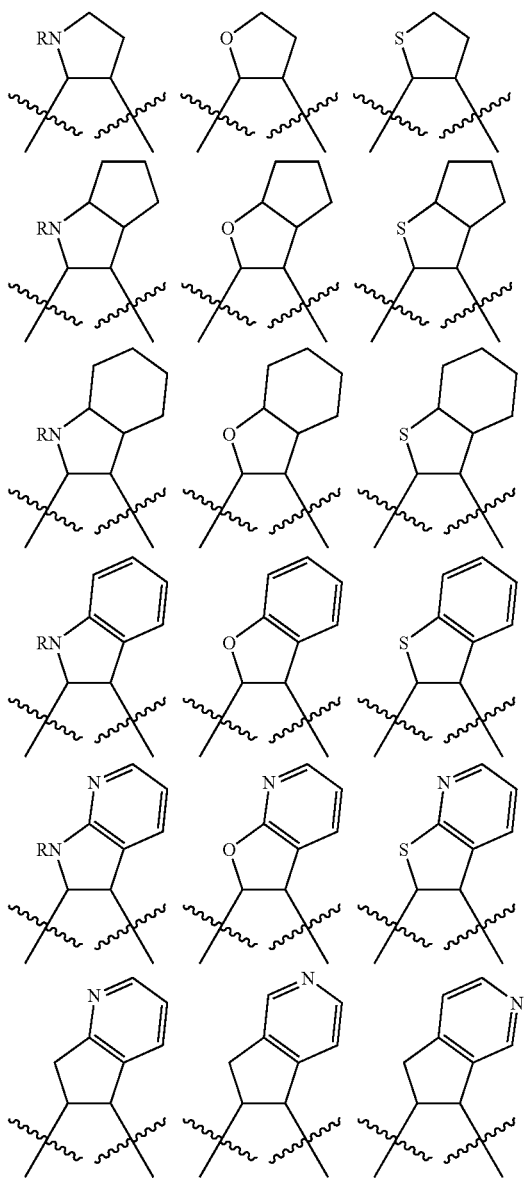

-continued
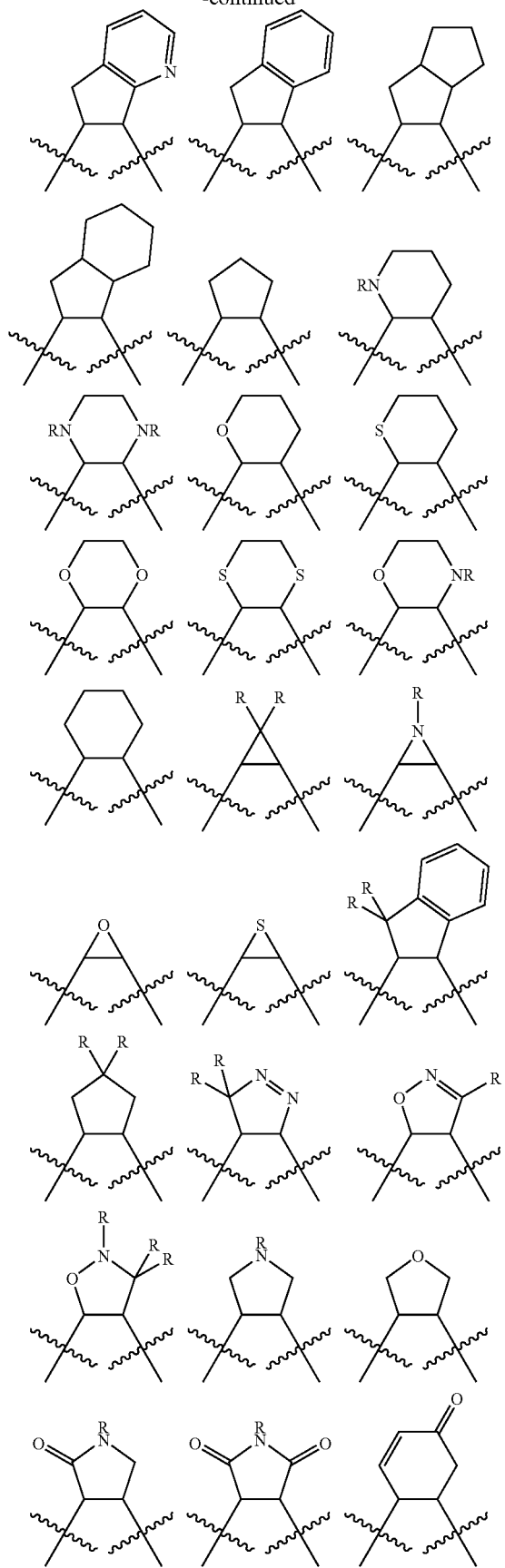
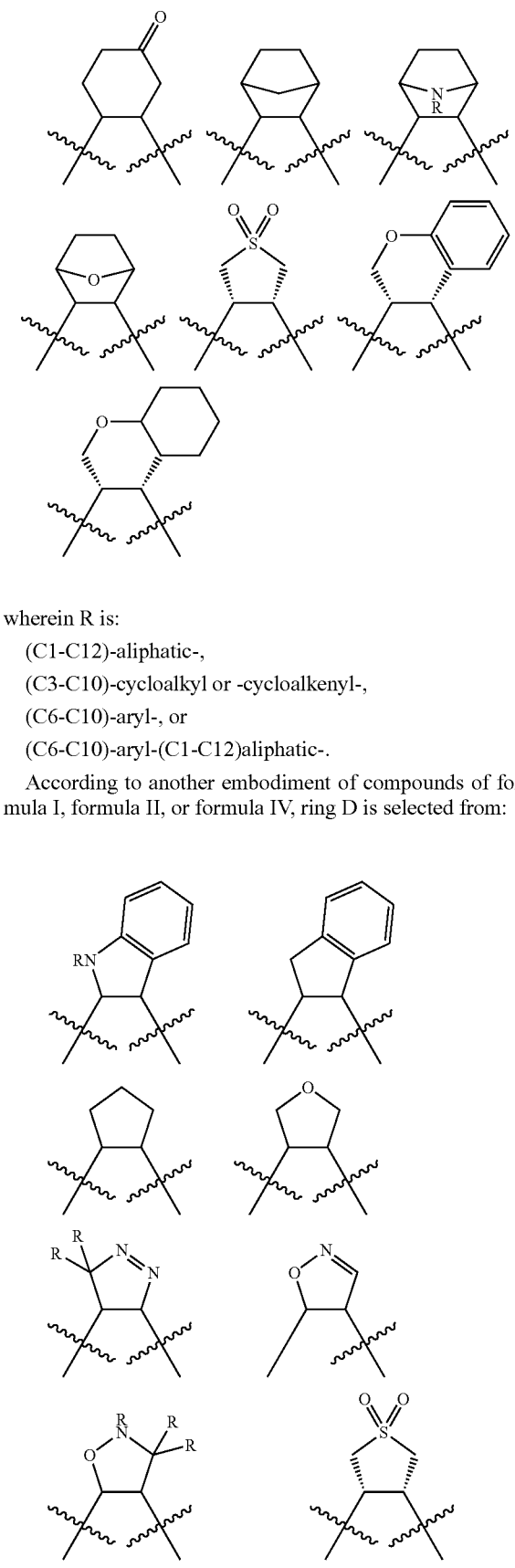
wherein R is:
(C1-C12)-aliphatic-,
(C3-C10)-cycloalkyl or -cycloalkenyl-,
(C6-C10)-aryl-, or
(C6-C10)-aryl-(C1-C12)aliphatic-.
According to another embodiment of compounds of formula I, formula II, or formula IV, ring D is selected from:

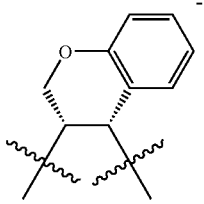 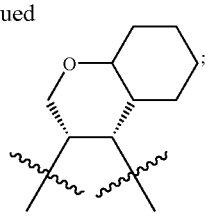
wherein R is:
 (C1-C12)-aliphatic-,
 (C3-C10)-cycloalkyl or -cycloalkenyl-,
 (C6-C10)-aryl-, or
 (C6-C10)-aryl-(C1-C12)aliphatic-.
According to another embodiment of compounds of formula I, formula II, or formula IV, rings A and B, together with the ring connected thereto include:
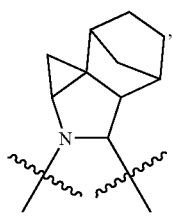 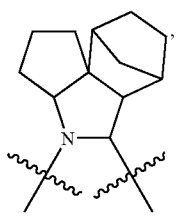
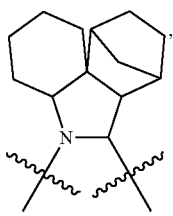 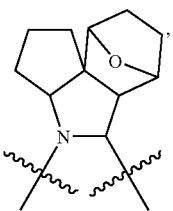
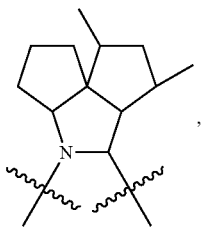 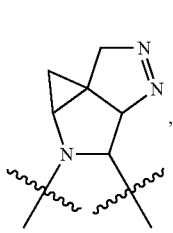
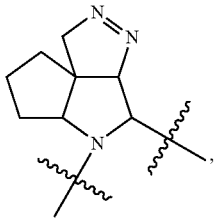 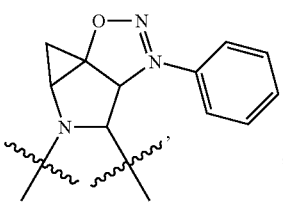
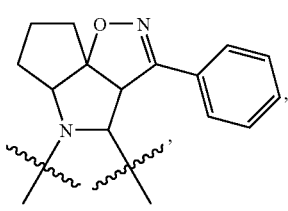
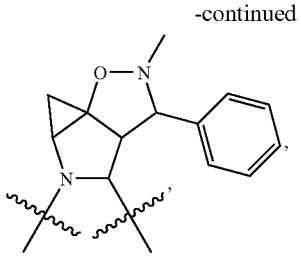
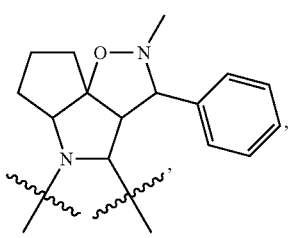
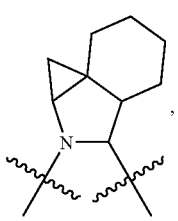 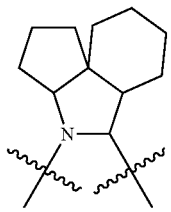
and
According to another embodiment of compounds of formula I, formula II, or formula IV, the
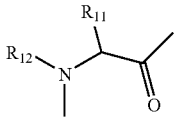
radical is:
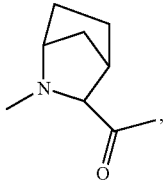 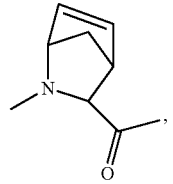
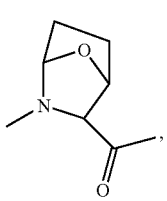 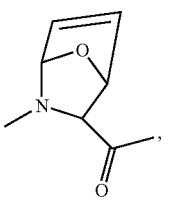
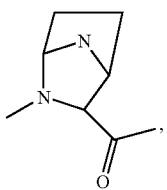 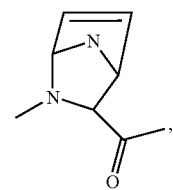

-continued
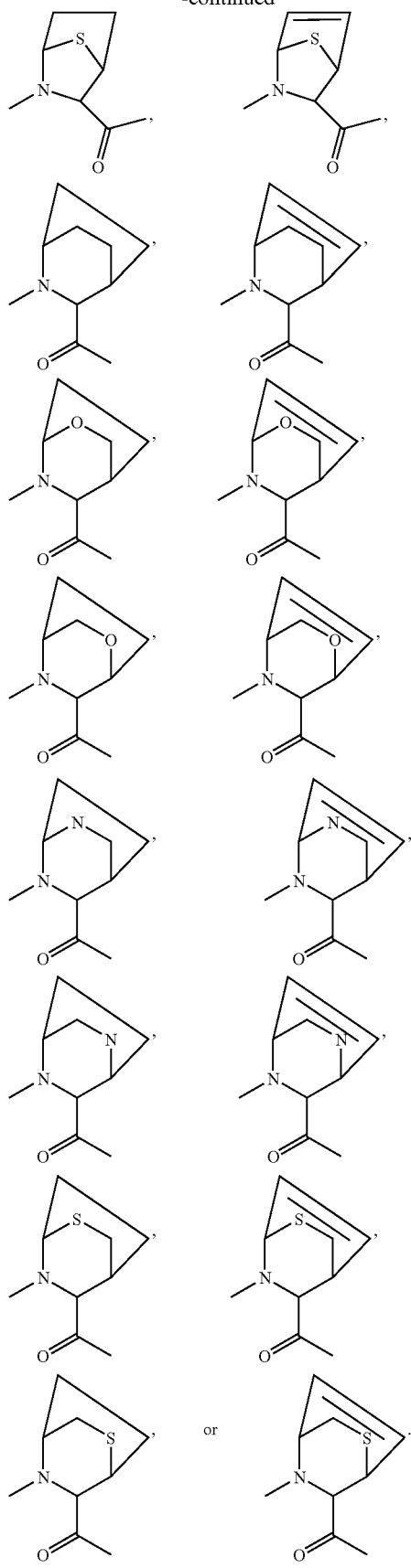
According to another embodiment of compounds of formula I, formula II, or formula IV, the
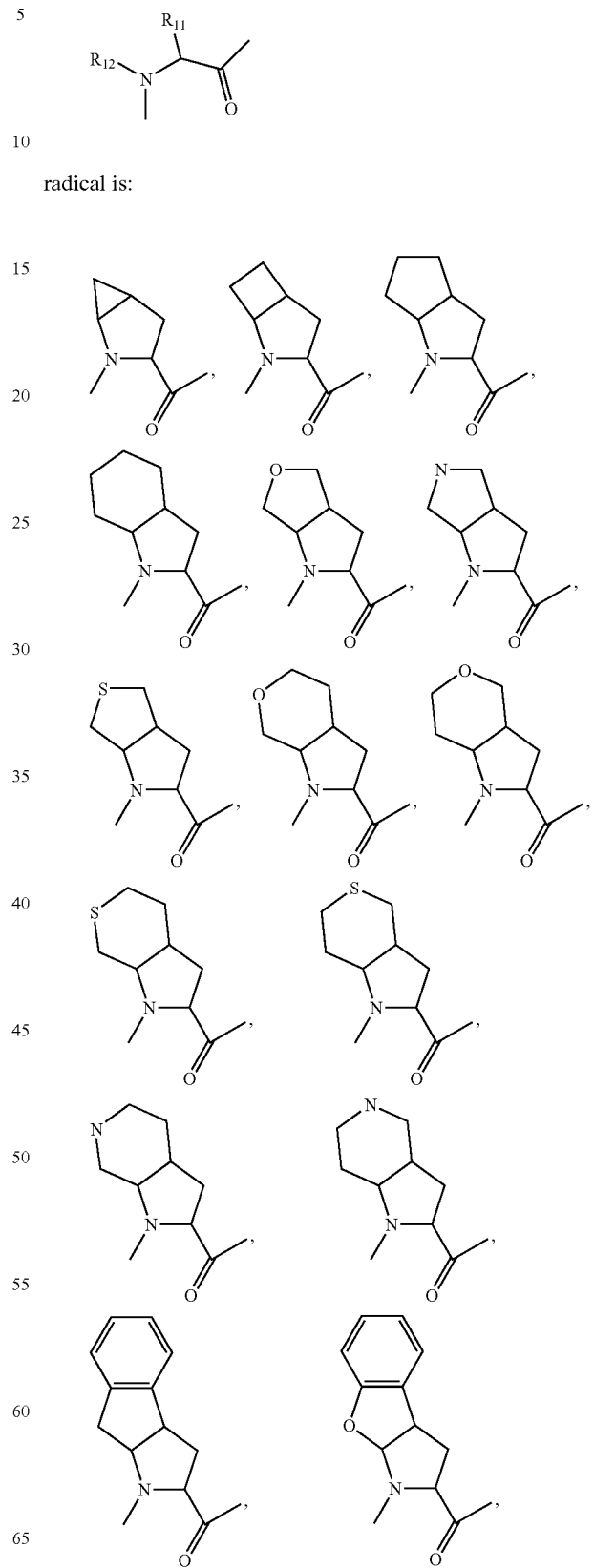
radical is:

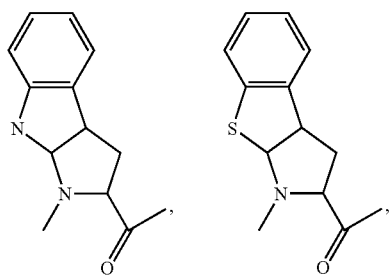
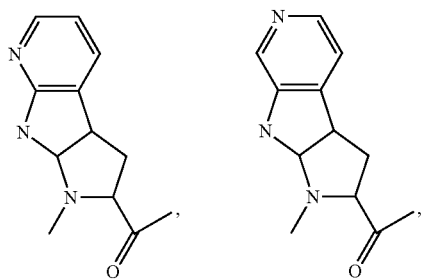
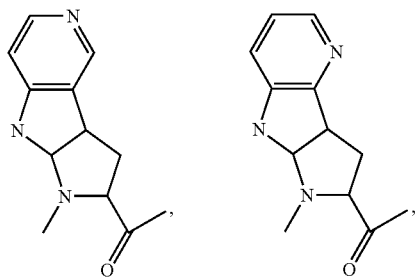
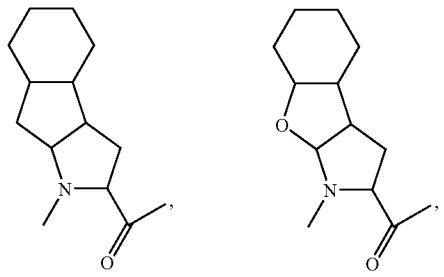
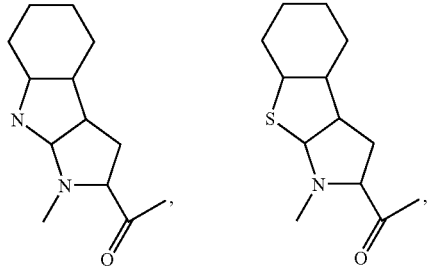
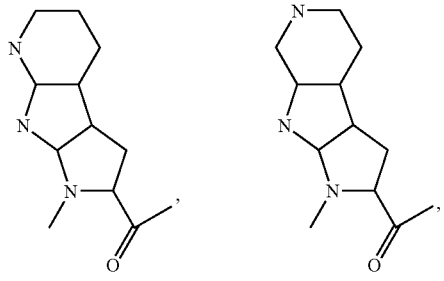
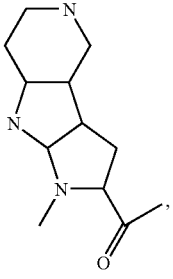
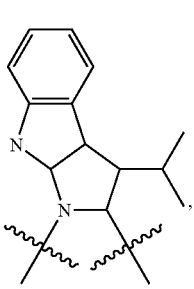
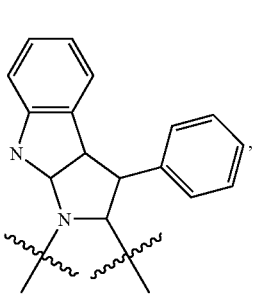
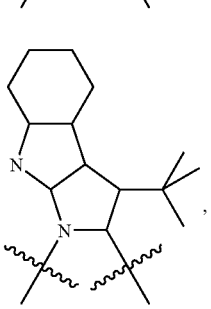
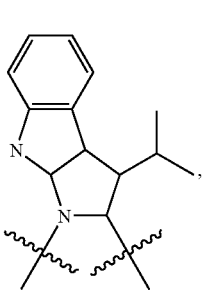
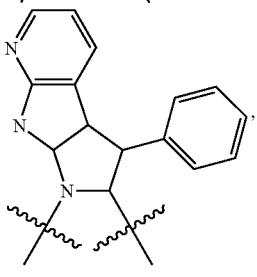

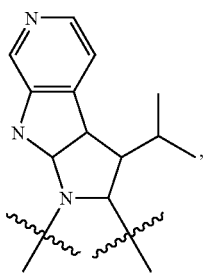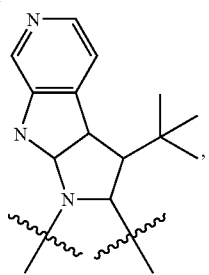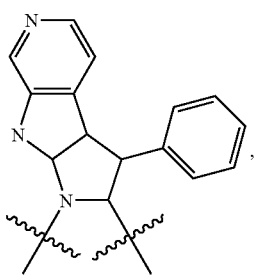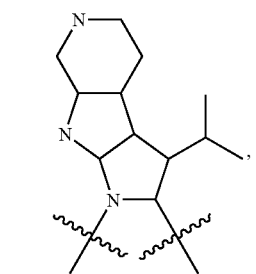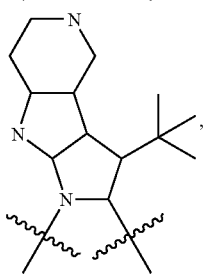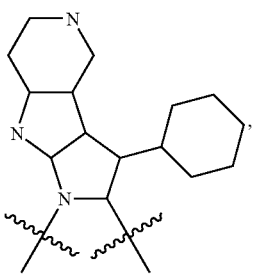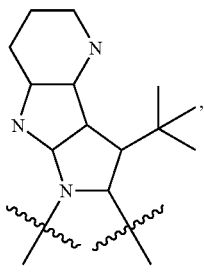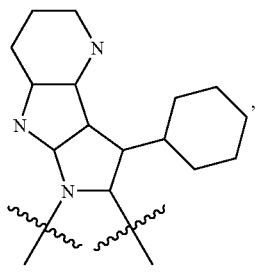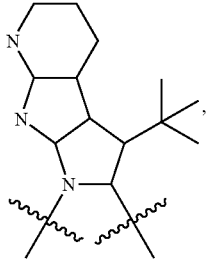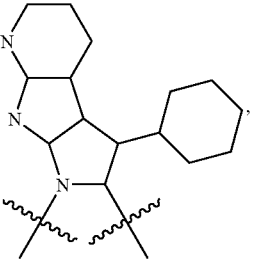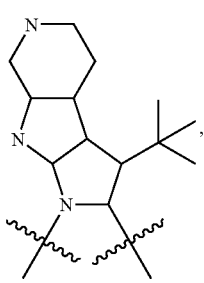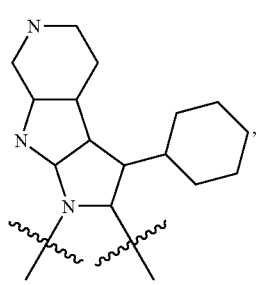
According to another embodiment of compounds of formula I, formula II, or formula IV, the
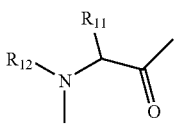
radical is:
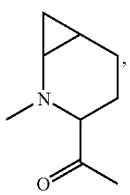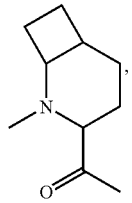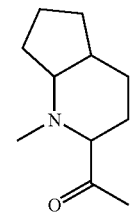

-continued
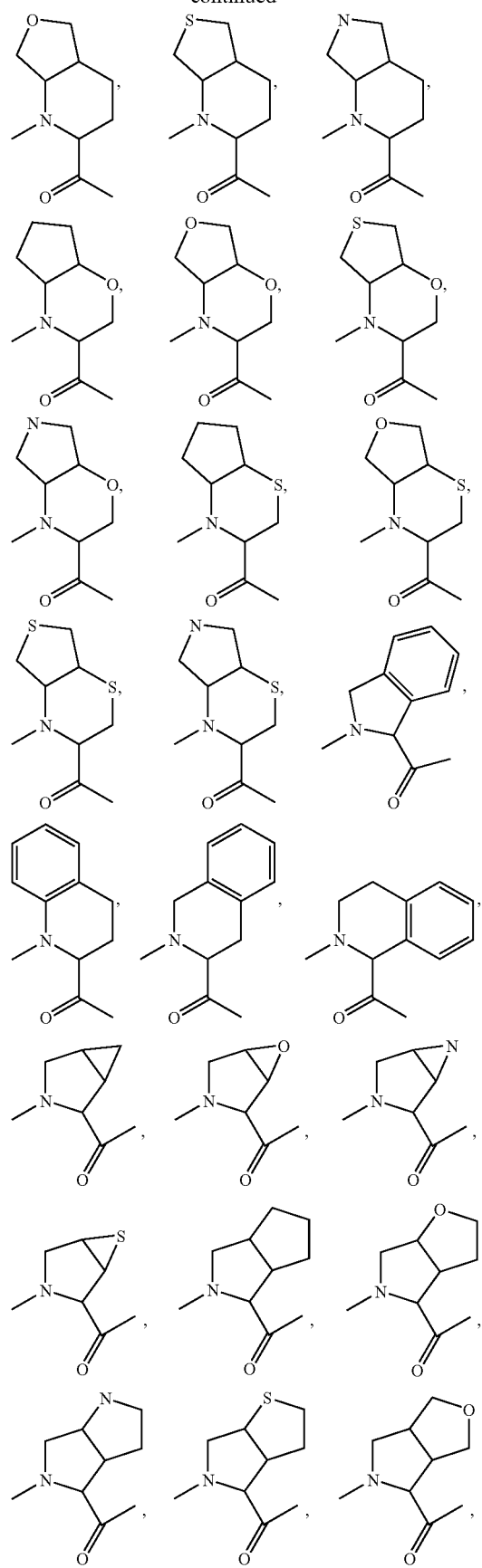
-continued
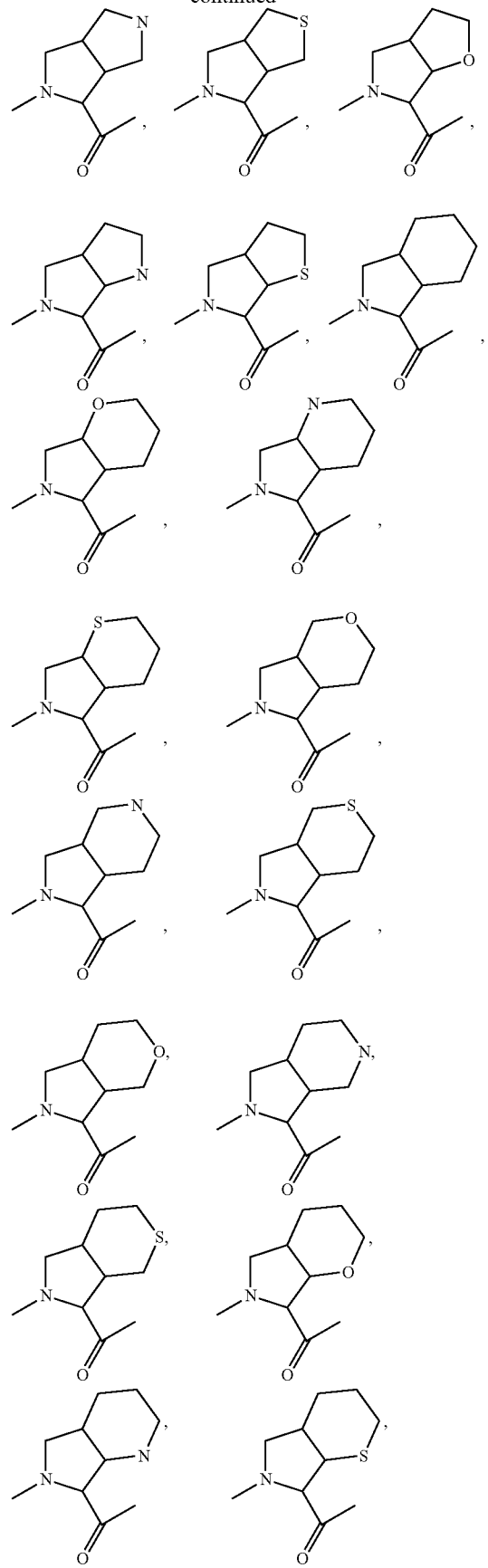

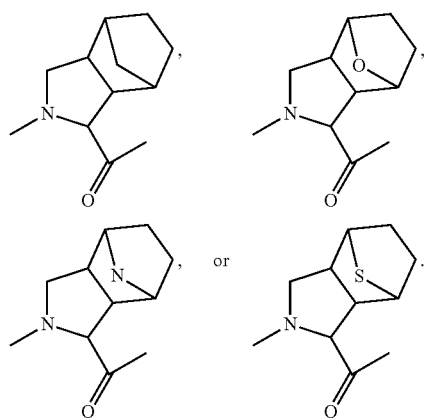
According to another embodiment of compounds of formula I, formula II, or formula IV, the
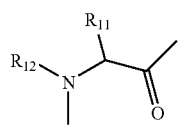
radical is:
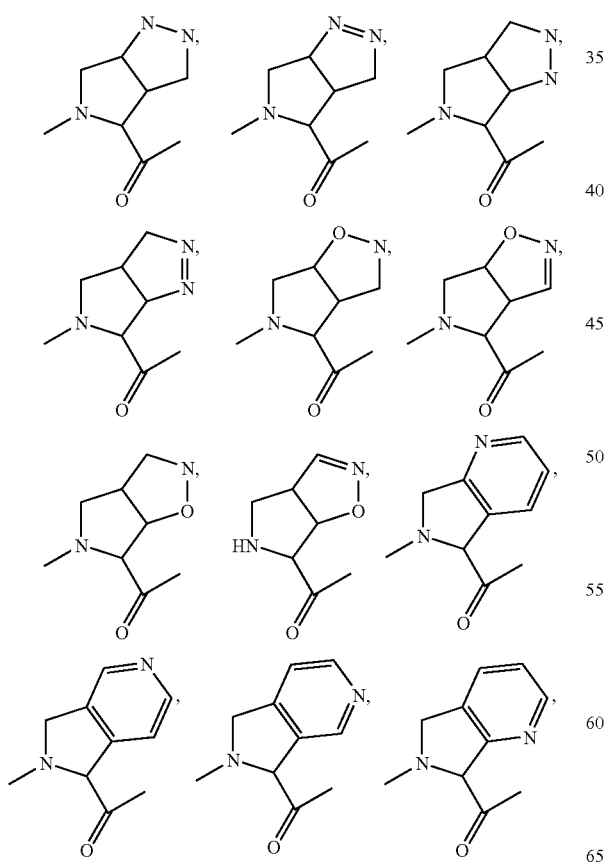
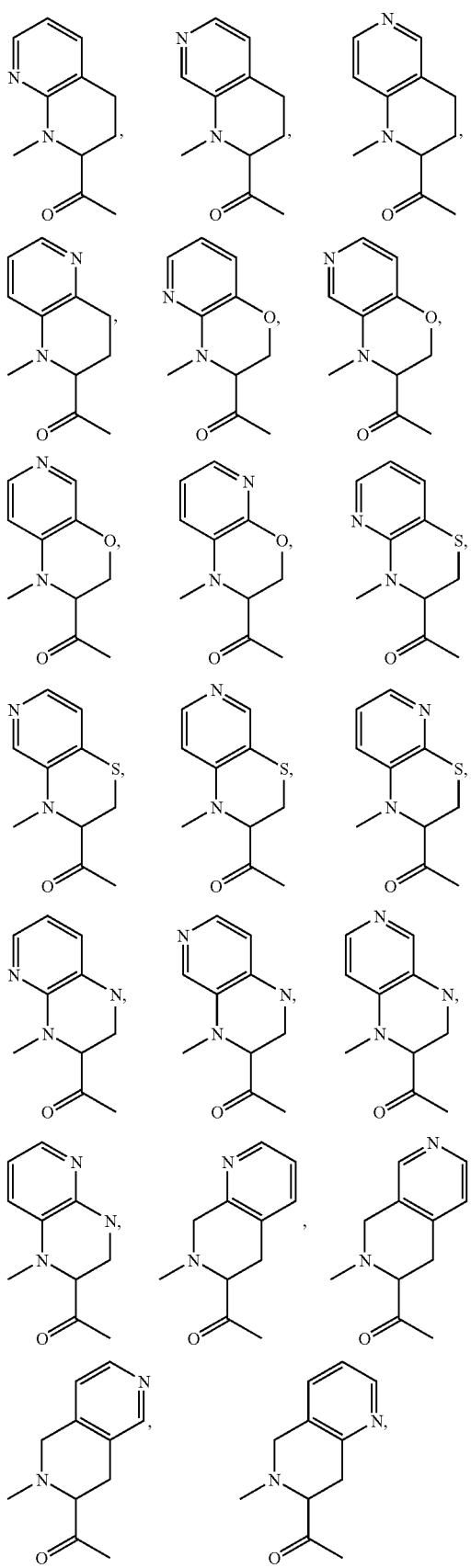

-continued
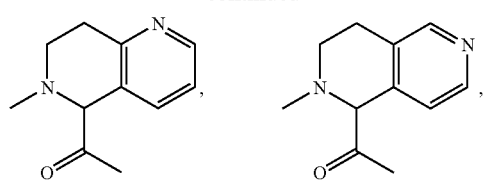
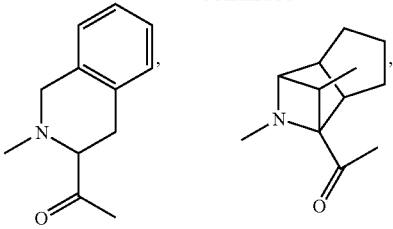
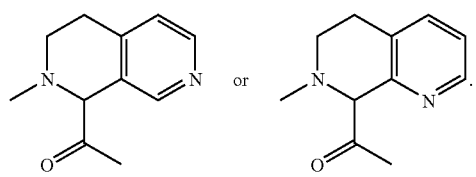
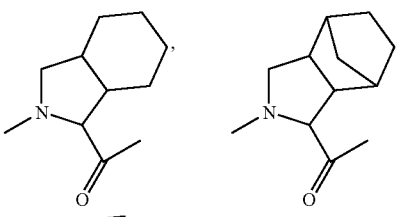
According to another embodiment of compounds of formula I, formula II, or formula IV, the
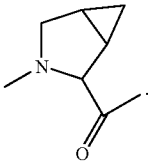
radical is:
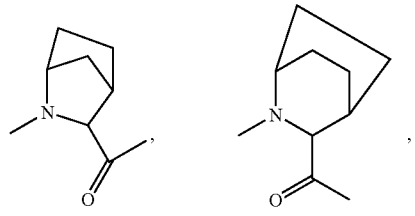
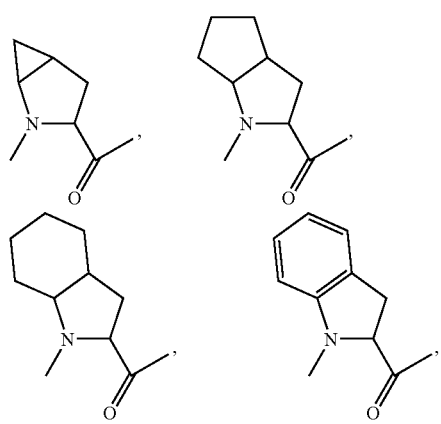
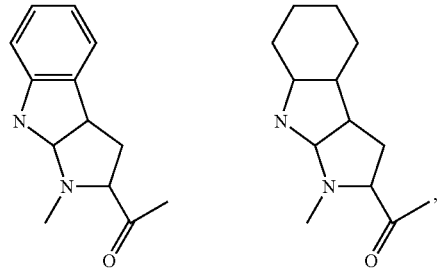
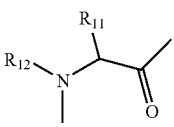
According to another embodiment of compounds of formula I, formula II, or formula IV, the
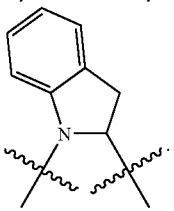
radical is:
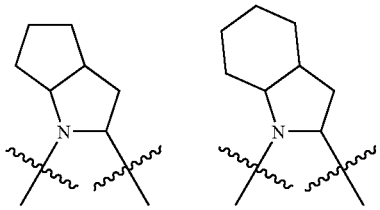
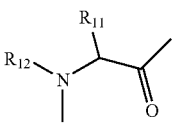
According to another embodiment of compounds of formula I, formula II, or formula IV, the
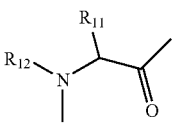

radical is:

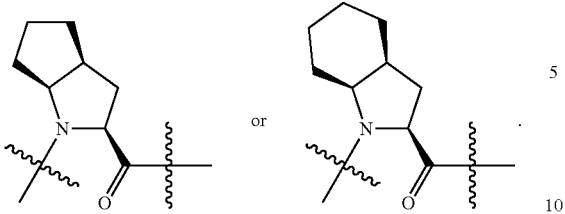

According to another embodiment of compounds of formula I or formula II, the

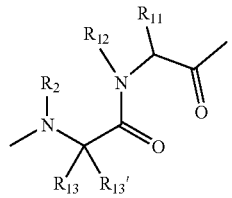

radical is:

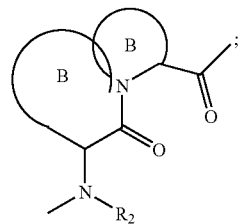

wherein each B independently forms a 3- to a 20-membered carbocyclic or heterocyclic ring system;
wherein each ring B is either aromatic or nonaromatic;
wherein each heteroatom in the heterocyclic ring system is N, NH, O, S, SO, or $SO_2$;
wherein, in the ring system, each ring is linearly fused, bridged, or spirocyclic;
wherein each ring is optionally fused to a (C6-C10)aryl, (C5-C10)heteroaryl, (C3-C10)cycloalkyl, or (C3-C10) heterocyclyl; and
wherein each ring is optionally substituted with up to 3 substituents selected independently from J.

According to another embodiment of compounds of formula I or formula II, the

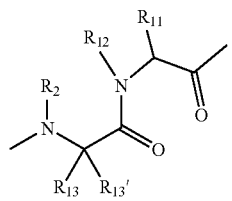

radical is:

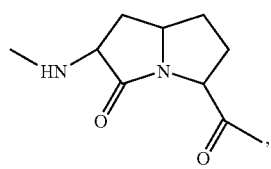

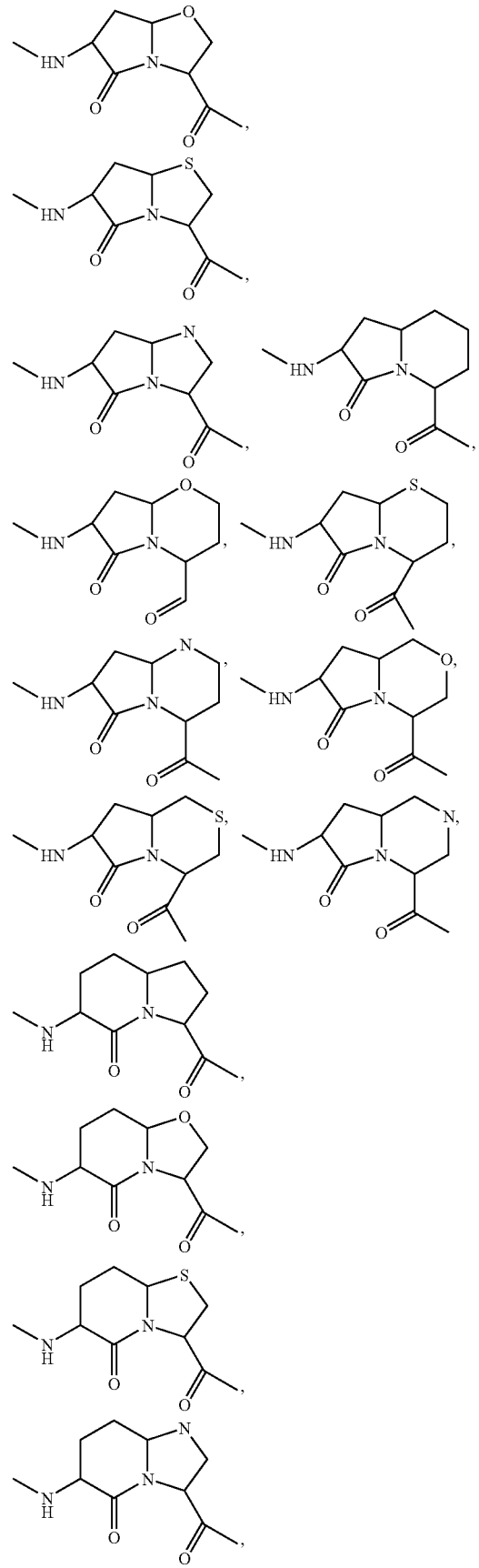

According to another embodiment of compounds of formula I or formula II, the

<img>structure with R_{11}, R_{12}, R_{2}, R_{13}, R_{13}'</img> radical is:

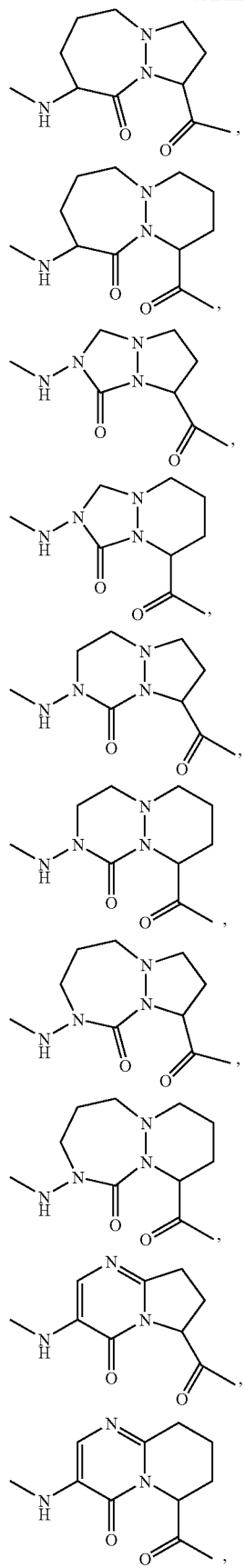
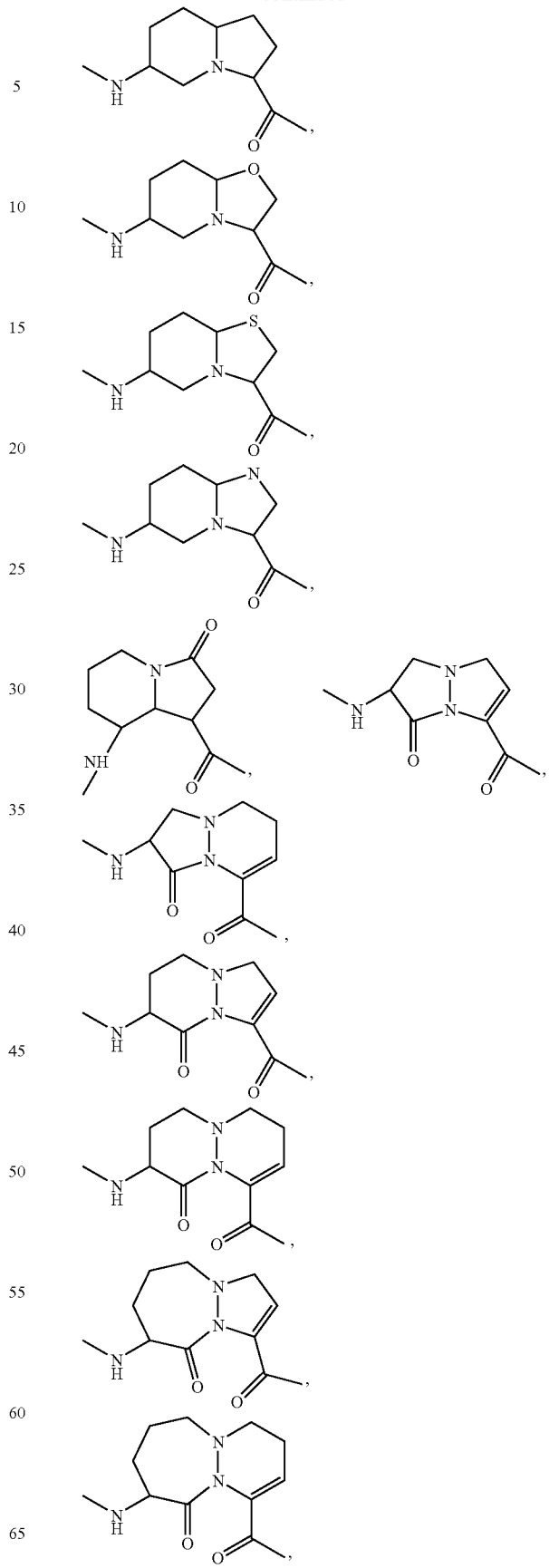

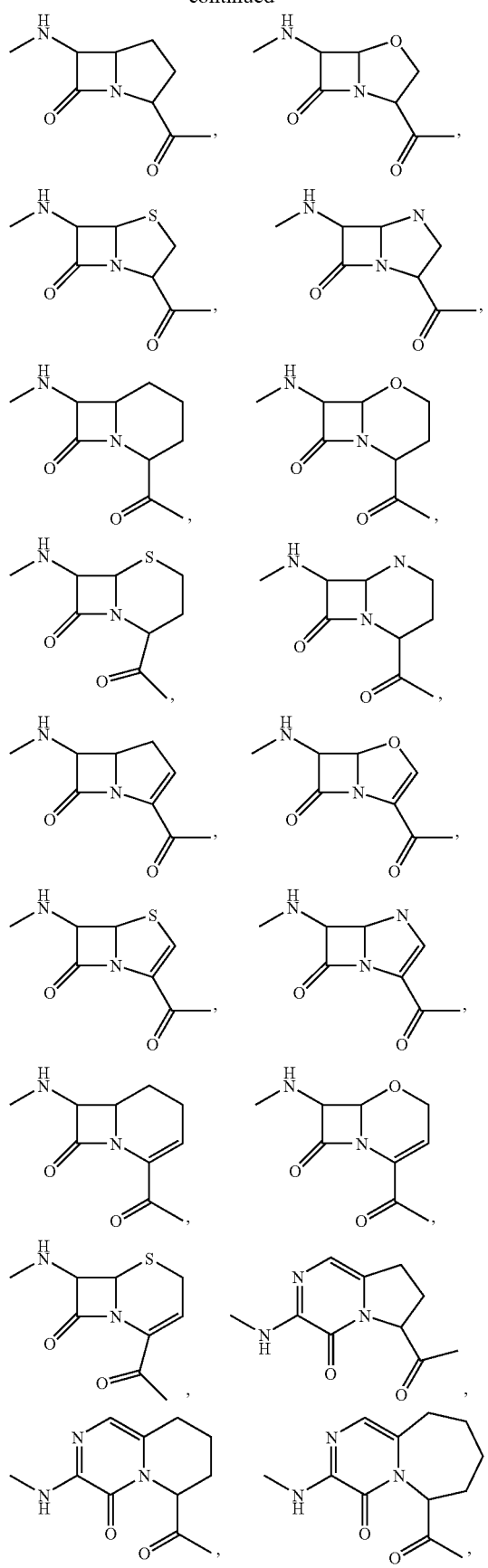
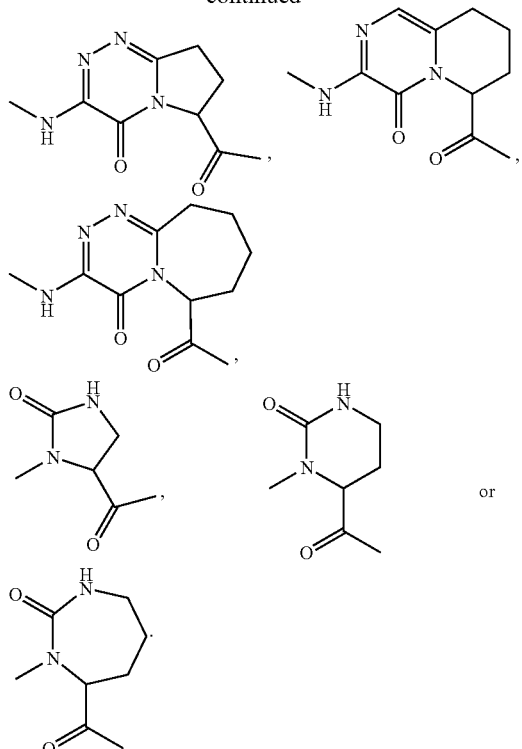
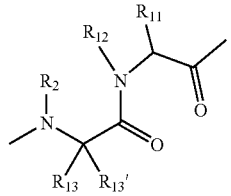
According to another embodiment of compounds of formula I or formula II, the
$$\begin{array}{c} R_{12}\phantom{-}\overset{R_{11}}{\underset{|}{N}}\\ R_2\phantom{-}\underset{|}{N}\phantom{-}\underset{\underset{R_{13}\phantom{.}R_{13}'}{|}}{\overset{|}{C}}\phantom{-}\underset{O}{\overset{\|}{C}}\phantom{-}N\end{array}$$
radical is:
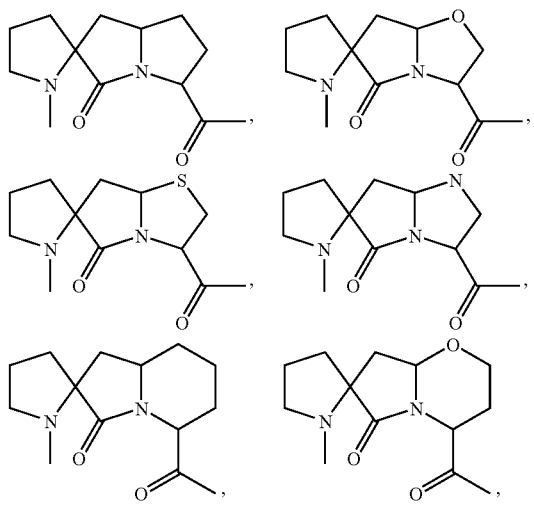

wherein B forms a 3- to a 20-membered carbocyclic or heterocyclic ring system;

wherein each ring B is either aromatic or nonaromatic;

wherein each heteroatom in the heterocyclic ring system is N, NH, O, S, SO, or $SO_2$;

wherein, in the ring system, each ring is linearly fused, bridged, or spirocyclic;

wherein each ring is optionally fused to a (C6-C10)aryl, (C5-C10)heteroaryl, (C3-C10)cycloalkyl, or (C3-C10)heterocyclyl;

wherein, in the carbocyclic or heterocyclic ring system, each ring is linearly fused, bridged, or spirocyclic; and wherein each ring is optionally substituted with up to 3 substituents selected independently from J.

According to another embodiment of compounds of formula I or formula II, the radical is:

According to another embodiment of compounds of formula I or formula II, the

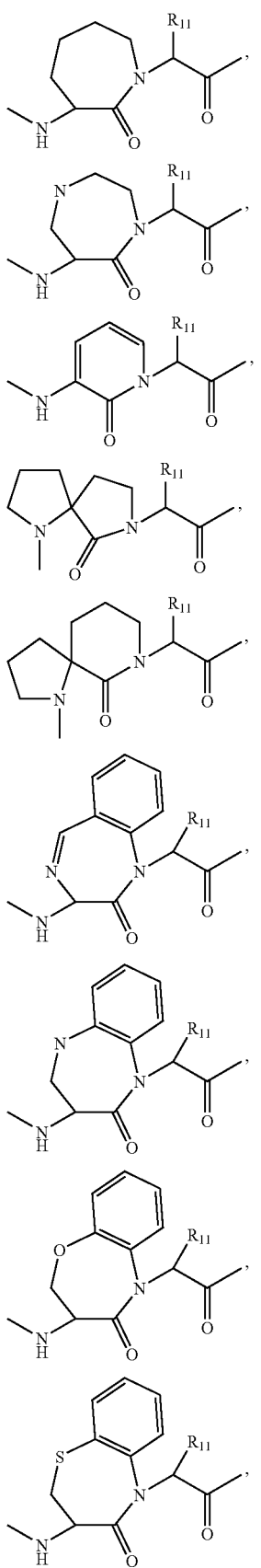
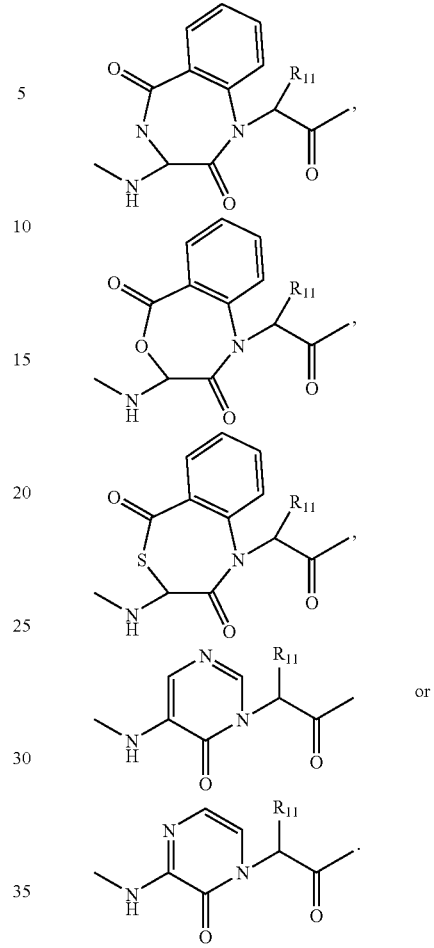

In the above radicals it is understood that the $R_{11}$ variable is H.

According to another embodiment of compounds of formula I, formula II, or formula IV, $R_{11}$ and $R_{12}$ together with the atoms to which they are bound form a 6- to 10-membered mono- or bicyclic carbocyclic or heterocyclic ring system;

wherein each heteroatom in the heterocyclic ring system is selected from the group consisting of N, NH, O, S, SO, and $SO_2$; and wherein said ring has up to 3 substituents selected independently from J.

Any of the ring systems may be substituted as set forth herein. In one embodiment of compounds of formula I, formula II, or formula IV, the ring substituents are oxo, fluoro, difluoro (particularly vicininal difluoro), and hydroxy. In another embodiment, the following ring systems:

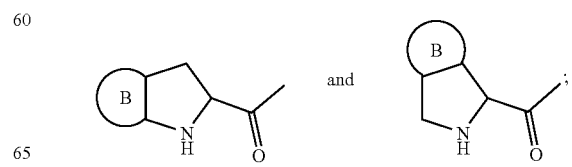

are optionally substituted with oxo, fluoro, difluoro (particularly vicininal difluoro), and hydroxy; wherein ring B is a 5-membered carbocyclic ring, optionally having one unsaturated bond.

In another embodiment of compounds of formula I, formula II, or formula IV, heteroatoms are selected from the group consisting of N, NH, O, SO, and $SO_2$.

According to another embodiment of compounds of formula I, formula II, or formula IV, $R_{5'}$ is H and $R_5$ is (C1-C6)-alkyl, wherein the alkyl group is optionally substituted with fluoro or —SH.

According to another embodiment of compounds of formula I, formula II, or formula IV, the (C1-C6)-alkyl group is substituted with 1 to 3 fluoro groups.

According to another embodiment of compounds of formula I, formula II, or formula IV, $R_5$ and $R_{5'}$ are independently:

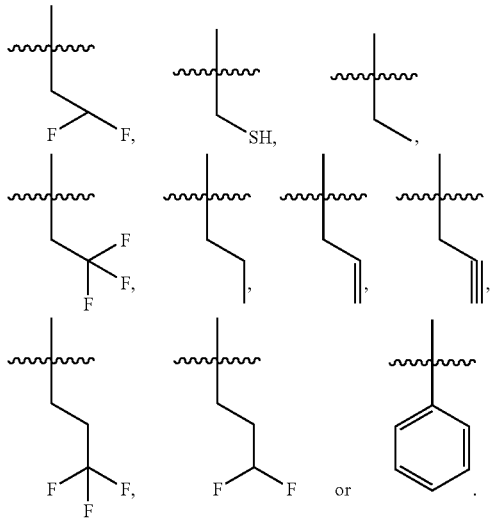

According to another embodiment of compounds of formula I, formula II, or formula IV, $R_{5'}$ is H and $R_5$ is:

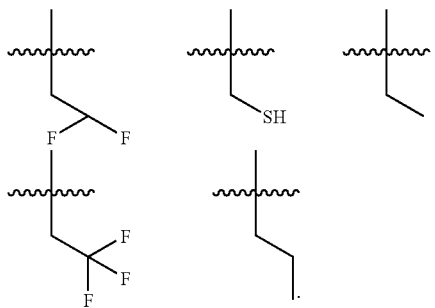

According to another embodiment of compounds of formula I, formula II, or formula IV, $R_5$ and $R_{5'}$ is:

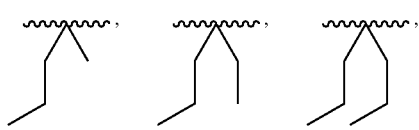

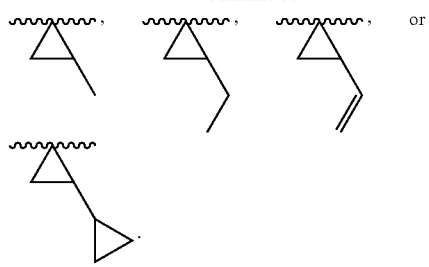

According to another embodiment of compounds of formula I, formula II, or formula IV, $R_{13}$ is:
(C1-C6)-alkyl,
(C3-C10)-cycloalkyl,
[(C3-C10)-cycloalkyl]-(C1-C12)-alkyl,
(C6-C10)-aryl,
(C6-C10)-aryl-(C1-C6)alkyl,
(C3-C10)-heterocyclyl,
(C6-C10)-heterocyclyl-(C1-C6)alkyl,
(C5-C10)-heteroaryl, or
(C5-C10)-heteroaryl-(C1-C6)-alkyl;

wherein $R_{13}$ is optionally substituted with up to 3 substituents independently selected from J; and wherein up to 3 aliphatic carbon atoms in $R_{13}$ may be replaced by a heteroatom selected from O, NH, S, SO, or $SO_2$ in a chemically stable arrangement.

According to another embodiment of compounds of formula I, formula II, or formula IV, $R_{13'}$ is hydrogen and $R_{13}$ is:

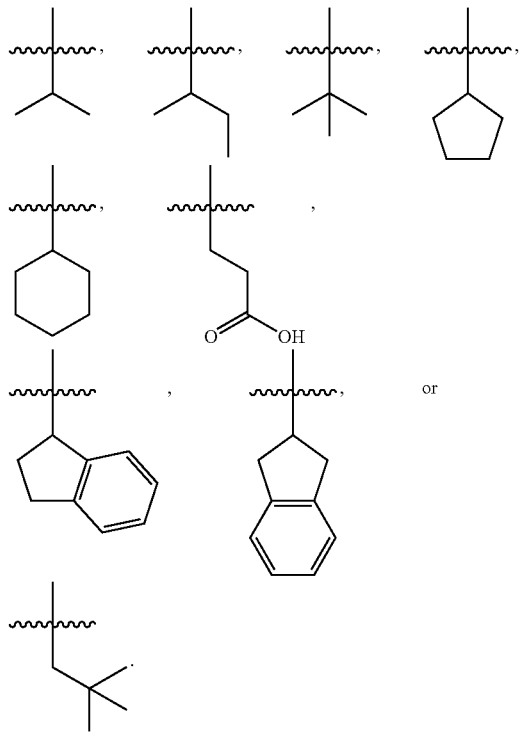

According to another embodiment of compounds of formula I, formula II, or formula IV, $R_{13}$ is:

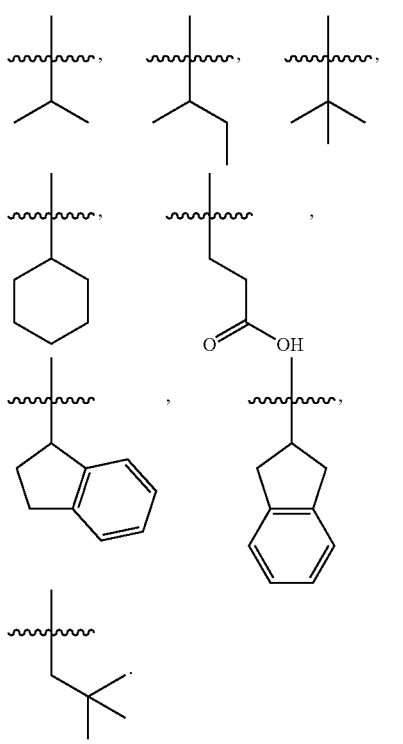

According to another embodiment of compounds of formula I or formula II,

R₁ is:
- (C1-C6)-alkyl,
- (C3-C10)-cycloalkyl,
- [(C3-C10)-cycloalkyl]-(C1-C12)-alkyl,
- (C6-C10)-aryl,
- (C6-C10)-aryl-(C1-C6)alkyl,
- (C3-C10)-heterocyclyl,
- (C6-C10)-heterocyclyl-(C1-C6)alkyl,
- (C5-C10)-heteroaryl, or
- (C5-C10)-heteroaryl-(C1-C6)-alkyl;

wherein R₁ is optionally substituted with up to 3 substituents independently selected from J; and wherein up to 3 aliphatic carbon atoms in R₁ may be replaced by a heteroatom selected from O, NH, S, SO, or SO₂ in a chemically stable arrangement.

According to another embodiment of compounds of formula I or formula II, R₁, is hydrogen and R₁ is:

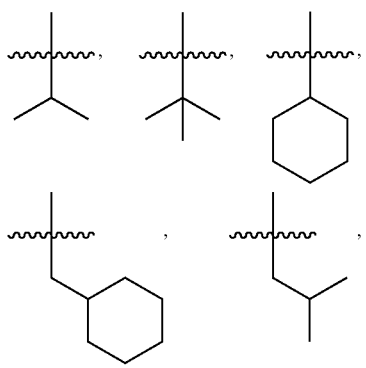

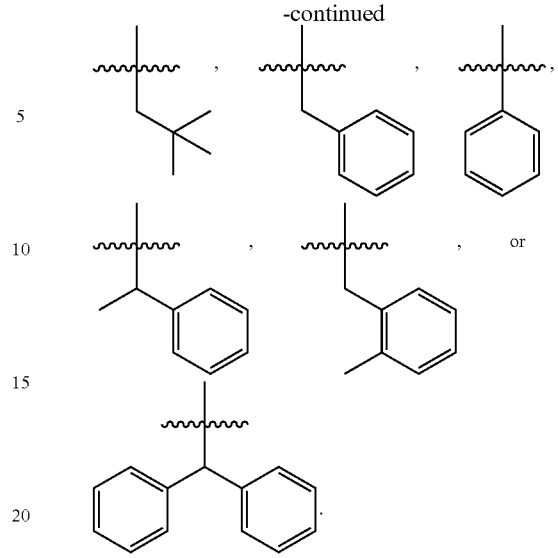

According to another embodiment of compounds of formula I or formula II, R₁ is:

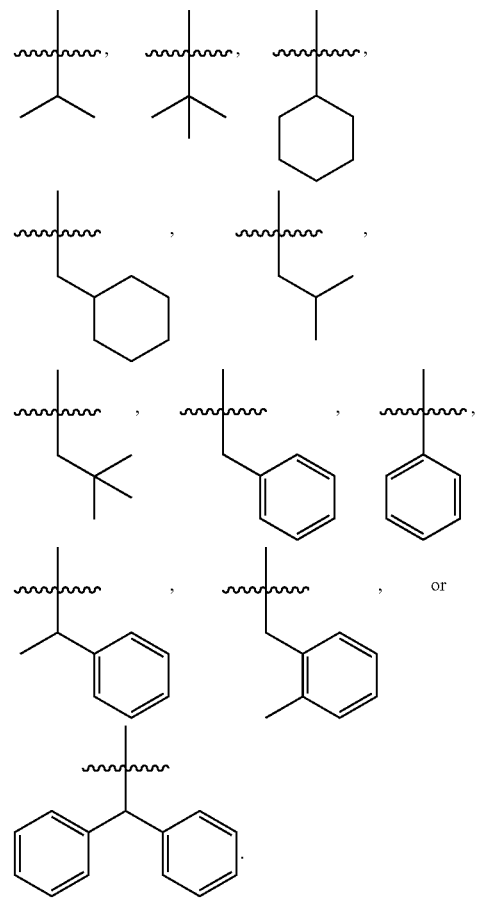

According to another embodiment of compounds of formula I or formula IV, T is selected from: (C6-C10)-aryl, (C6-C10)-aryl-(C1-C12)aliphatic, (C3-C10)-cycloalkyl or -cycloalkenyl, [(C3-C10)-cycloalkyl or -cycloalkenyl]-(C1-C12)-aliphatic, (C3-C10)-heterocyclyl, (C3-C10)-heterocyclyl-(C1-C12)-aliphatic, (C5-C10)heteroaryl, or (C5-C10)heteroaryl-(C1-C12)-aliphatic, wherein each T is optionally substituted with up to 3 J substituents.

According to another embodiment of compounds of formula I, formula II, or formula IV, T is (C5-C10)heteroaryl, wherein T is optionally substituted with up to 3 J substitutents.

According to another embodiment of compounds of formula I or formula IV, T is:

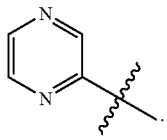

According to another embodiment of compounds of formula I, formula II, or formula IV, T is:

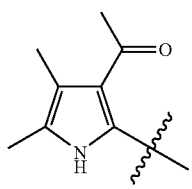

According to another embodiment of compounds of formula I or formula IV, T is:

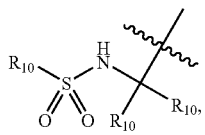 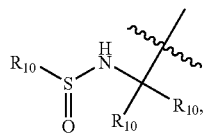

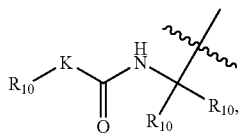

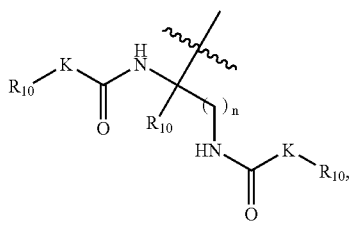

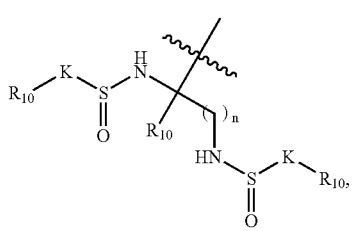

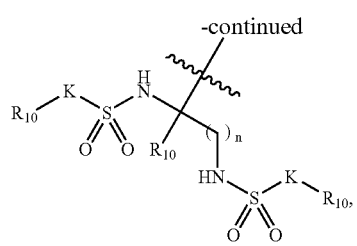

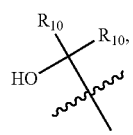 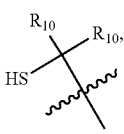

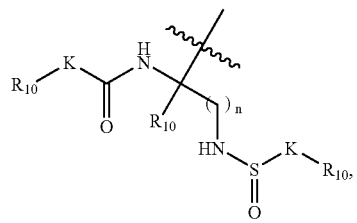

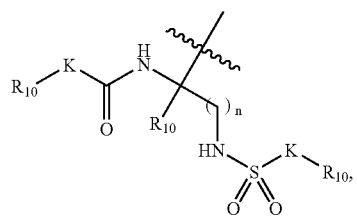

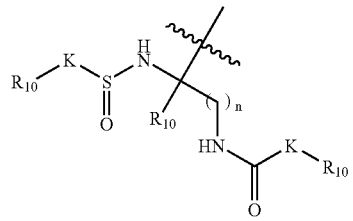

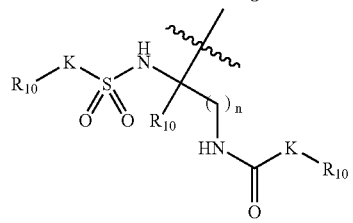 or

According to another embodiment of compounds of formula I or formula IV, T is:

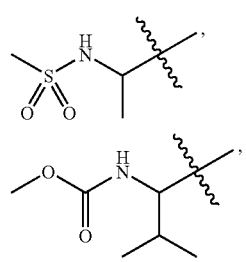 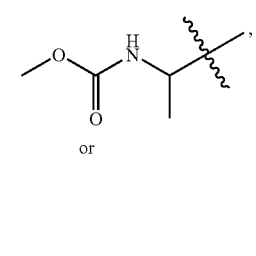 or

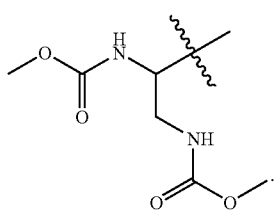

According to another embodiment of compounds of formula I or formula IV, T contains at least one hydrogen bond donor moiety selected from —NH$_2$, —NH—, —OH, and —SH.

According to another embodiment of compounds of formula I or formula IV, T is:

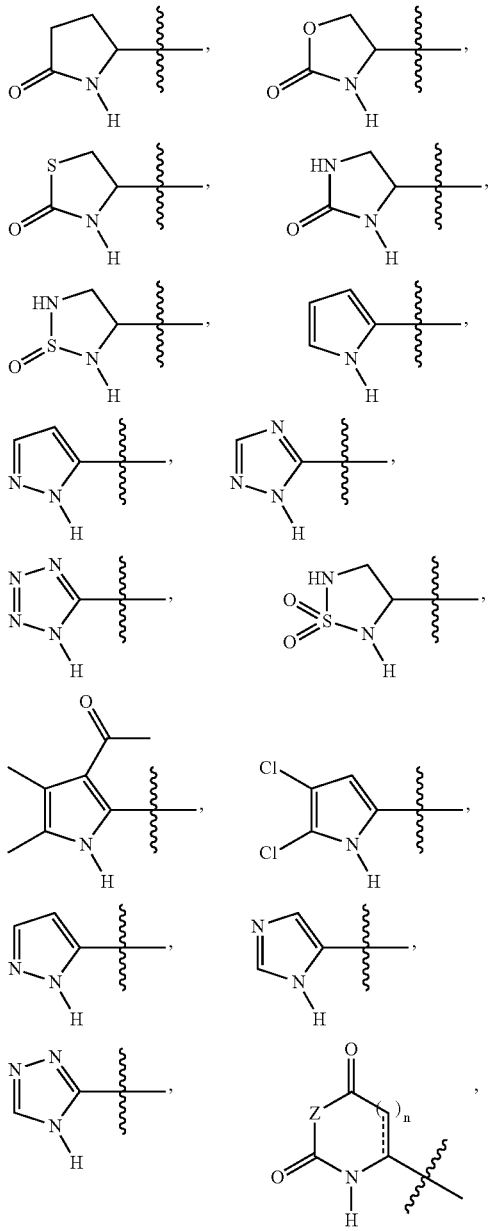

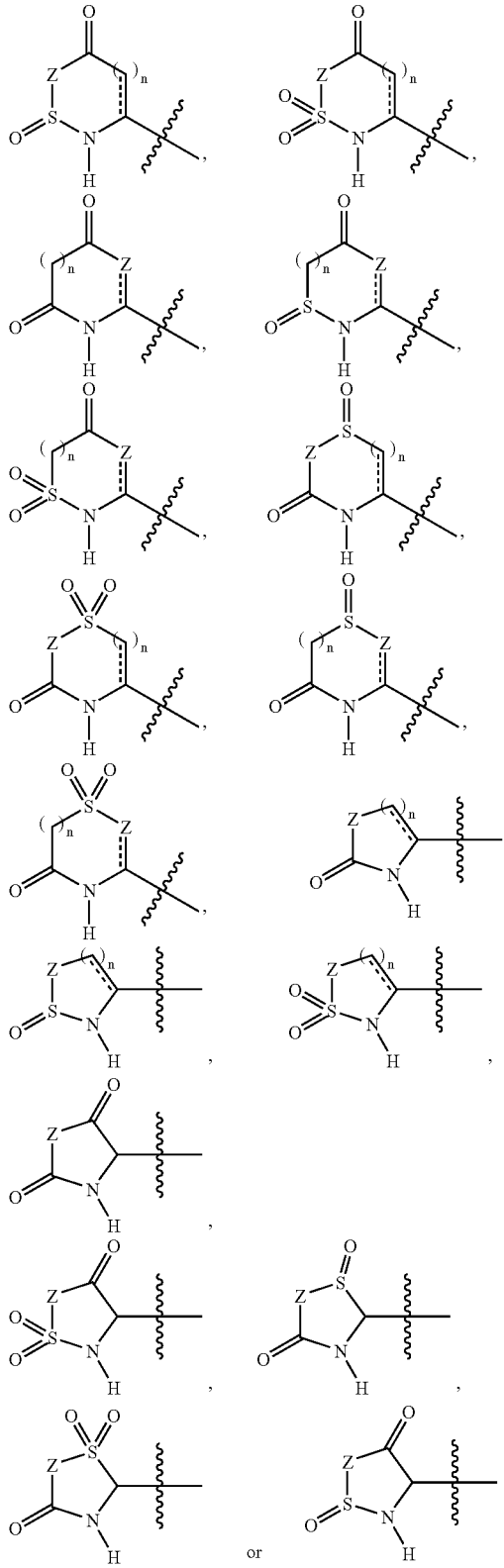

wherein:
T is optionally substituted with up to 3 J substituents, wherein J is as defined in claim 1;
Z is independently O, S, NR$_{10}$, C(R$_{10}$)$_2$ wherein R$_{10}$ is as defined in claim 1;

n is independently 1 or 2; and

===== independently a single bond or a double bond.

According to another embodiment of compounds of formula I or formula IV, T is:

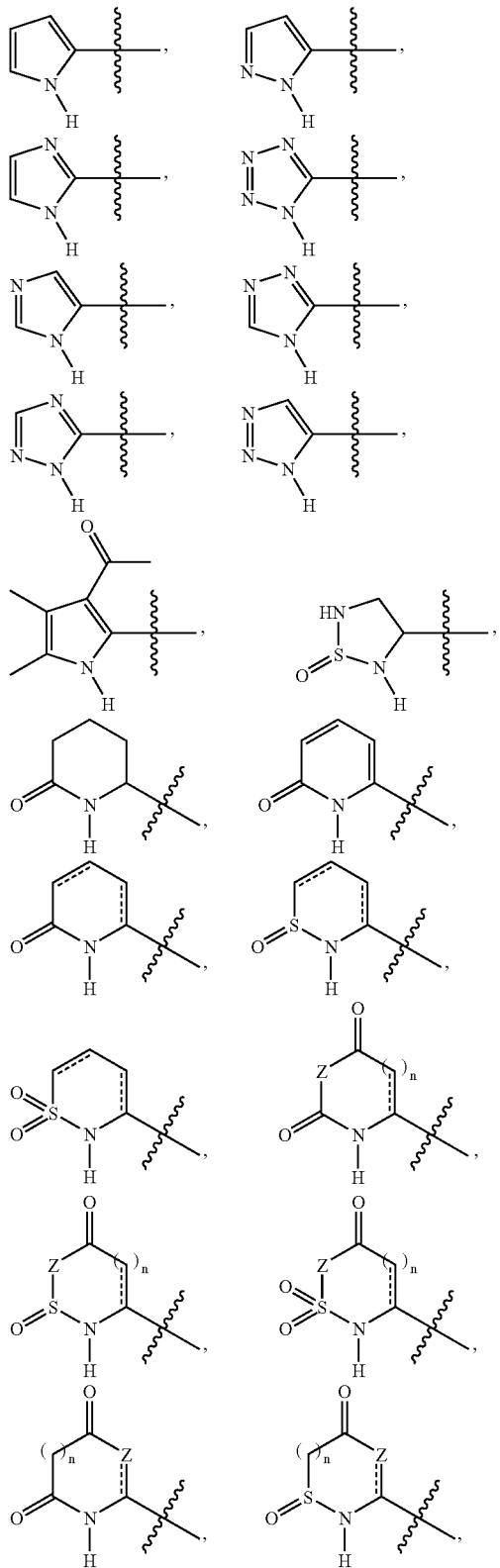

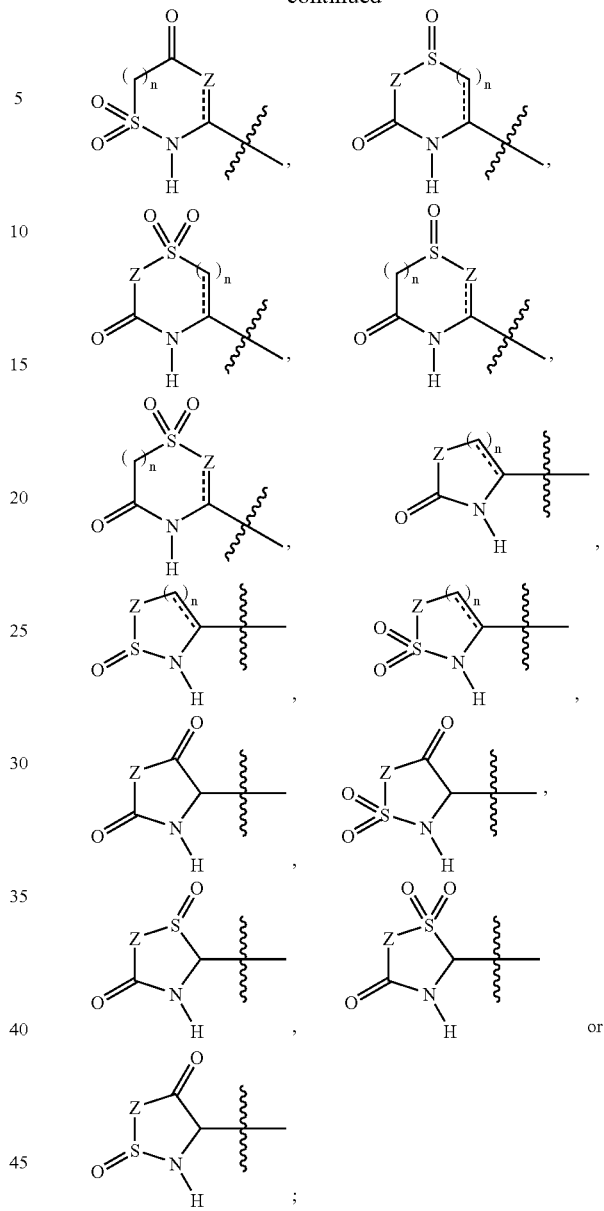

wherein:

T is optionally substituted with up to 4 J substituents, wherein J is as defined in claim 1;

Z is independently O, S, $NR_{10}$, $C(R_{10})_2$, SO, $SO_2$, wherein $R_{10}$ is as defined in claim 1;

n is independently 1 or 2; and

===== is independently a single bond or a double bond.

According to another embodiment of compounds of formula I or formula IV, T is:

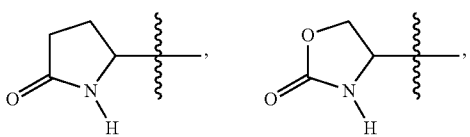

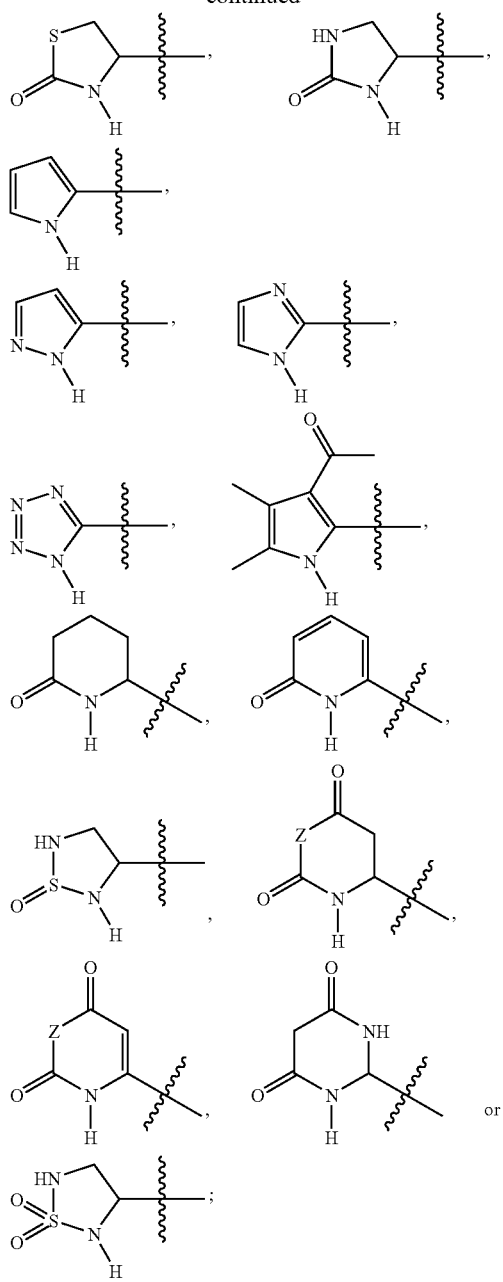

wherein:
T is optionally substituted with up to 4 J substituents, wherein J is as defined in claim 1; and Z is independently O, S, NR$_{10}$, C(R$_{10}$)$_2$, SO, SO$_2$, wherein R$_{10}$ is as defined in claim 1.

According to another embodiment of compounds of formula I or formula IV, T is:

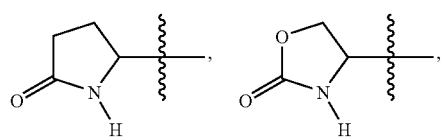

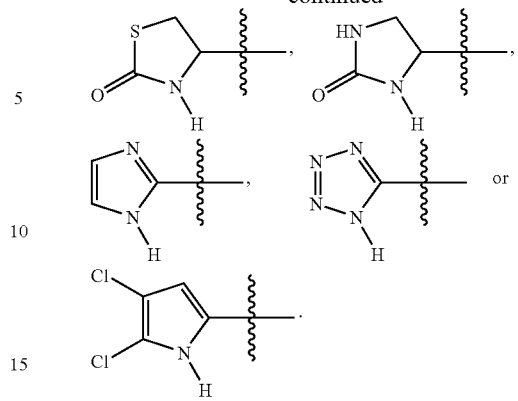

According to another embodiment of compounds of formula I or formula IV, V—R-T is selected from:

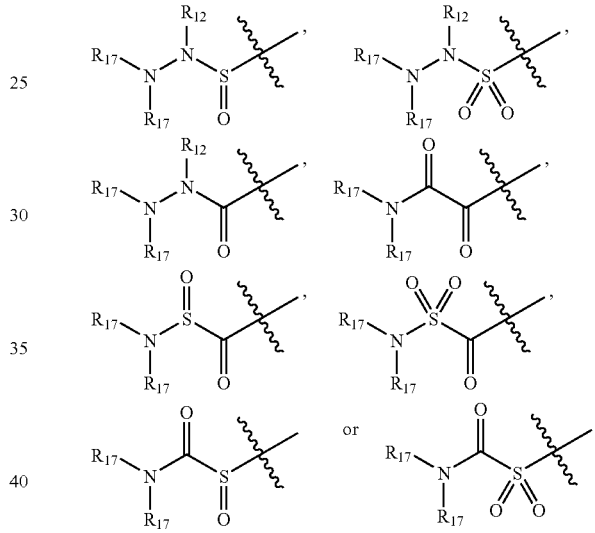

According to another embodiment for compounds of formula I or formula IV, V—R-T is:

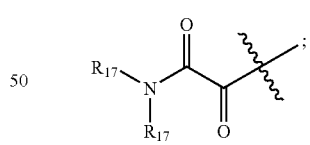

wherein:
one R$_{17}$ is hydrogen; and
one R$_{17}$ is:
(C1-C12)-aliphatic-;
(C6-C10)-aryl-(C1-C12)aliphatic-, or
(C3-C10)-cycloalkyl or -cycloalkenyl-;
  wherein up to 3 aliphatic carbon atoms in R$_{17}$ may be replaced by a heteroatom selected from O, N, NH, S, SO, or SO$_2$ in a chemically stable arrangement; and
  wherein R$_{17}$ is optionally substituted with up to 3 substituents independently selected from J.

According to another embodiment for compounds of formula I or formula IV, V—R-T is:

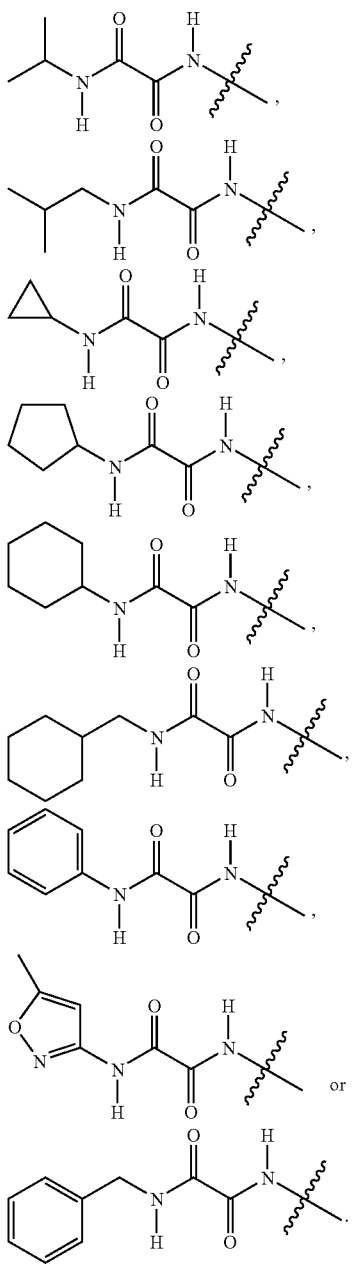

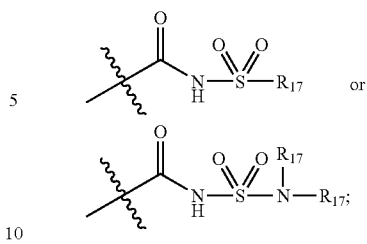

According to another embodiment of compounds of formula I, formula II, or formula IV, $R_2$ if present, and $R_4$, and $R_8$ are each independently H or (C1-C3)-alkyl.

According to another embodiment of compounds of formula I, formula II, or formula IV, $R_2$ if present, and $R_4$, and $R_8$ are each H.

According to another embodiment of compounds of formula I, formula II, or formula IV, $R_8$ is hydrogen, V is —C(O)—, R is a bond and T is as defined in any of the embodiments herein.

According to one embodiment of compounds of formula IV, $R_8$ is hydrogen, W is as defined in any of the embodiments herein, V is —C(O)—, R is oxygen, and T is selected from:
(C1-C12)-aliphatic,
(C3-C10)-cycloalkyl or -cycloalkenyl, or
[(C3-C10)-cycloalkyl or -cycloalkenyl]-(C1-C12)-aliphatic.

According to another embodiment of compounds of formula I or formula II, W is:

wherein $R_{17}$ is:
hydrogen-,
(C1-C12)-aliphatic-,
(C3-C10)-cycloalkyl- or cycloalkenyl-,
[(C3-C10)-cycloalkyl- or cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)-aliphatic-,
(C5-C10)heteroaryl-, or
(C5-C10)heteroaryl-(C1-C12)-aliphatic-, or
wherein two $R_{17}$ groups, which are bound to the same nitrogen atom, together with that nitrogen atom, optionally form a (C3-C10)-membered saturated or partially unsaturated heterocyclic ring system having in addition to the nitrogen up to 2 additional heteroatoms selected from N, NH, O, S, SO, and $SO_2$;
wherein $R_{17}$ is optionally substituted with up to 3 J substituents.

According to another embodiment of compounds of formula I or formula II, W is:

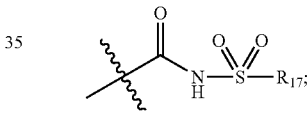

wherein $R_{17}$ is:
(C1-C12)-aliphatic-,
(C3-C10)-cycloalkyl- or cycloalkenyl-,
[(C3-C10)-cycloalkyl- or cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)-aliphatic-,
(C5-C10)heteroaryl-, or
(C5-C10)heteroaryl-(C1-C12)-aliphatic-, or
wherein two $R_{17}$ groups, which are bound to the same nitrogen atom, together with that nitrogen atom, optionally form a (C3-C10)-membered saturated or partially unsaturated heterocyclic ring system having in addition to the nitrogen up to 2 additional heteroatoms selected from N, NH, O, S, SO, and $SO_2$ and wherein said ring is optionally substituted with up to 3 J substituents; and
wherein $R_{17}$ is optionally substituted with up to 3 J substituents.

According to another embodiment of compounds of formula I or formula II, W is:

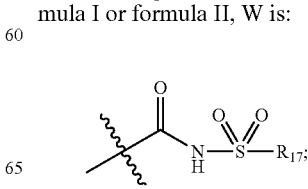

wherein $R_{17}$ is:
(C6-C10)-aryl-,
(C6-C10)-aryl-(C1-C12)aliphatic-,
(C5-C10)heteroaryl-, or
(C5-C10)heteroaryl-(C1-C12)-aliphatic-,
wherein $R_{17}$ is optionally substituted with up to 3 J substituents.

According to another embodiment of compounds of formula I or formula II, W is:

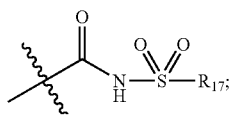

wherein $R_{17}$ is:
(C6-C10)-aryl-,
(C6-C10)-aryl-(C1-C12)aliphatic-,
(C5-C10)heteroaryl-, or
(C5-C10)heteroaryl-(C1-C12)-aliphatic-,
and $R_{17}$ is unsubstituted.

According to another embodiment of compounds of formula I or formula II, W is:

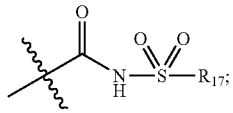

wherein $R_{17}$ is:
(C6-C10)-aryl-,
(C6-C10)-aryl-(C1-C12)aliphatic-,
wherein $R_{17}$ is optionally substituted with up to 3 J substituents.

According to another embodiment of compounds of formula I or formula II, W is:

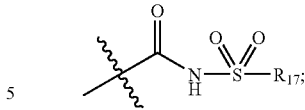

wherein $R_{17}$ is:
(C6-C10)-aryl-,
(C6-C10)-aryl-(C1-C12)aliphatic-,
and $R_{17}$ is unsubstituted.

According to another embodiment of compounds of formula I, formula II, or formula IV, J is halogen —OR', —NO$_2$, —CF$_3$, —OCF$_3$, —R', oxo, 1,2-methylenedioxy, —N(R')$_2$, —SR', —SOR', —SO$_2$R', —C(O)R', —COOR' —CON(R')$_2$, —N(R') COR', —N (COR') COR', —CN, or —SO$_2$N (R')$_2$.

According to another embodiment of compounds of formula I, formula II, or formula IV, $J_2$ is halogen, —OR', —NO$_2$, —CF$_3$, —OCF$_3$, —R', oxo, 1,2-methylenedioxy, —N(R')$_2$, —SR', —SOR', —SO$_2$R', —C(O)R', —COOR' —CON(R')$_2$, —N(R')COR', —N(COR')COR', —CN, or —SO$_2$N(R')$_2$.

According to another embodiment of compounds of formula I, formula II, or formula IV, in J and $J_2$ the halogen is chloro or fluoro. In another embodiment, the halogen is fluoro.

According to another embodiment of compounds of formula I or formula II, $R_{1'}$ is H.

According to another embodiment of compounds of formula I, formula II, or formula IV, $R_{13'}$ is H.

According to another embodiment of compounds of formula I, formula II, or formula IV, $R_{11'}$ is H.

According to another embodiment of compounds of formula I, formula II, or formula IV, $R_{12}$ is H.

Another embodiment of this invention provides a process for preparing a compound of this invention. These processes are described in the schemes and examples.

According to another embodiment in compounds of formula I, the compound is:

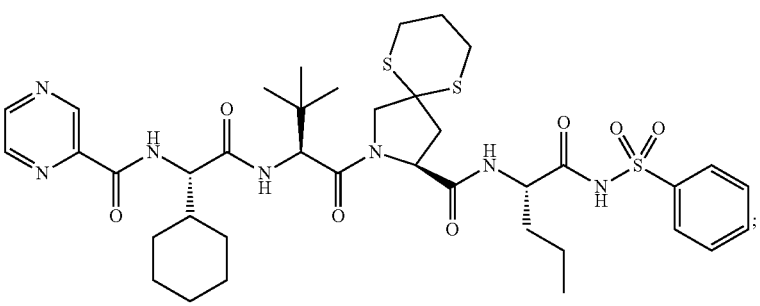

1

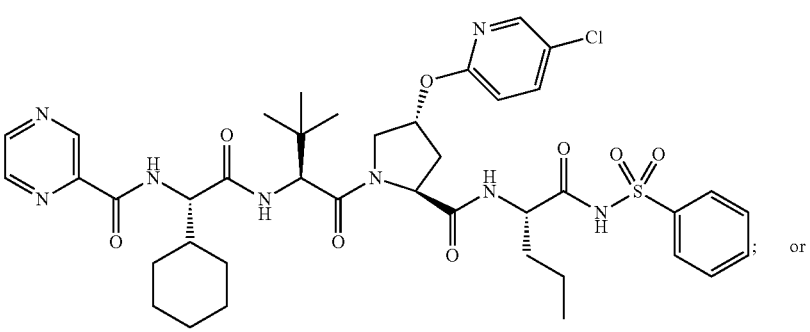

2 or

-continued

3

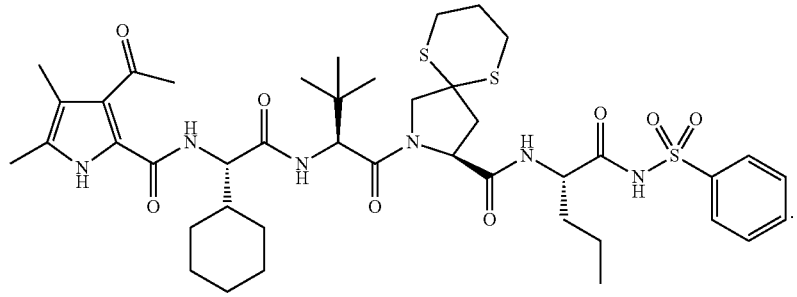

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

In another embodiment, the compounds of this invention have the structure and stereochemistry depicted in compounds 1-3.

Any of the embodiments recited above, including those embodiments in the above species, may be combined to produce another embodiment of this invention.

Abbreviations which are used in the schemes, preparations and the examples that follow are:
THF: tetrahydrofuran
DMF: N,N,-dimethylformamide
EtOAc: ethyl acetate
AcOH: acetic acid
NMM: N-methylmorpholine
NMP: N-methylpyyrolidinone
EtOH: ethanol
t-BuOH: tert-butanol
Et$_2$O: diethyl ether
DMSO: dimethyl sulfoxide
DCCA: dichloroacetic acid
DIEA: diisopropylethylamine
MeCN: acetonitrile
TFA: trifluoroacetic acid
DBU: 1,8-diazabicyclo[5.4.0]undec-7-ene
DEAD: diethyl azodicarboxylate
HOBt: 1-hydroxybenzotriazole hydrate
HOAt: 1-hydroxy-7-azabenzotriazole
EDC: 1-(3-dimethylaminopropyl)-3-ethylcarbodiimide hydrochloride
Boc: tert-butyloxycarbonyl
Boc$_2$O: di-tert-butyldicarbonate
Cbz: benzyloxycarbonyl
Cbz-Cl: benzyl chloroformate
Fmoc: 9-fluorenyl methyloxycarbonyl
Chg: cyclohexylglycine
t-BG: tert-butylglycine
mCBPA: 3-chloroperoxybenzoic acid
DAST: (diethylamino)sulfur trifluoride
TEMPO: 2,2,6,6-tetramethyl-1-piperidinyloxy, free radical
PyBOP: tris(pyrrolidino)bromophosphonium hexafluorophosphate
TBTU or HATU: 2-(1H-benzotriazole-1-yl)-1,1,3,3-tetramethyluronium tetrafluoroborate
DMAP: 4-dimethylaminopyridine
AIBN: 2,2'-azobisisobutyronitrile
DMEM: Dulbecco's minimal essential media
PBS: phosphate-buffered saline
rt or RT: room temperature
ON: overnight
ND: not determined
MS: mass spectrometry
LC: liquid chromatography General Synthetic Methodology:

The compounds of this invention may be prepared in general by methods known to those skilled in the art. Schemes 1-19 below illustrate synthetic routes to the compounds of the present invention. Other equivalent schemes, which will be readily apparent to the ordinary skilled organic chemist, may alternatively be used to synthesize various portions of the molecule as illustrated by the general scheme below, and the preparative examples that follow.

Scheme 1:

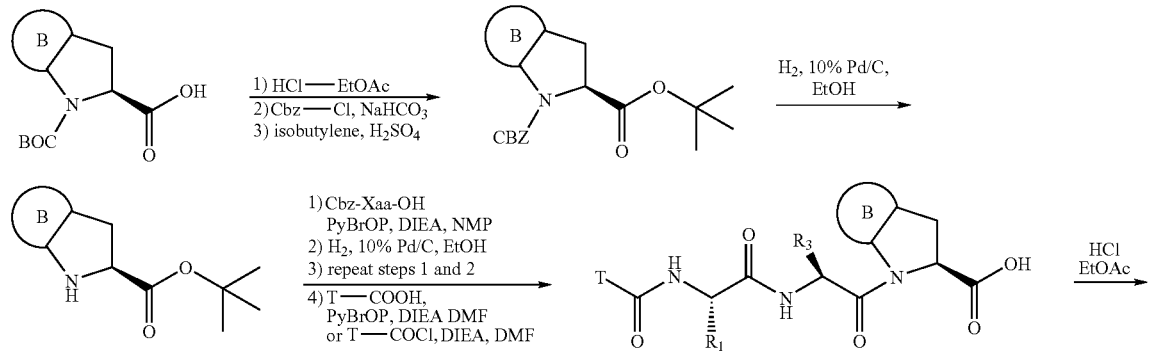

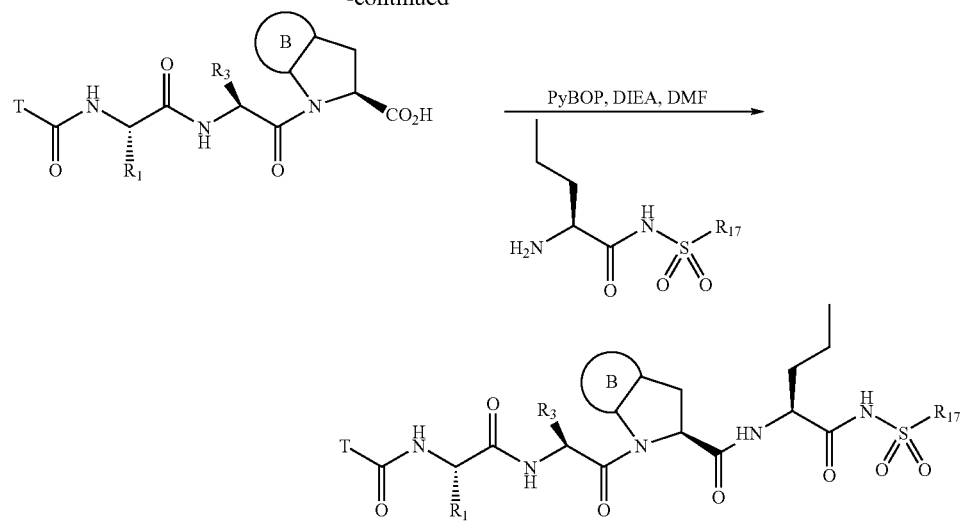

Scheme 1 above provides a general route for the preparation of compounds of formula I, formula II, or formula IV wherein T, $R_1$, $R_3$, $R_{17}$, and ring B are as defined in any of the embodiments herein. It will be appreciated by one of skill in the art that compounds of formula IV may be prepared according to scheme 1 wherein one less CBz-Xaa-OH group is coupled during the assembly of the compound.

Scheme 2:

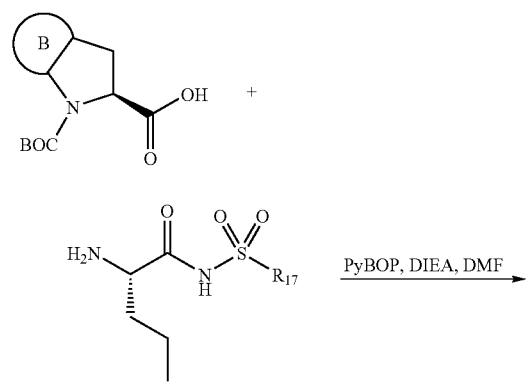

Scheme 2 above provides an alternate general route for the preparation of compounds of formula I, formula II, or formula IV wherein T, $R_1$, $R_3$, $R_{17}$, and ring B are as defined in any of the embodiments herein. It will be appreciated by one of skill in the art that compounds of formula IV may be prepared according to scheme 2 wherein one less CBz-Xaa-OH group is coupled during the assembly of the compound.

Scheme 3:

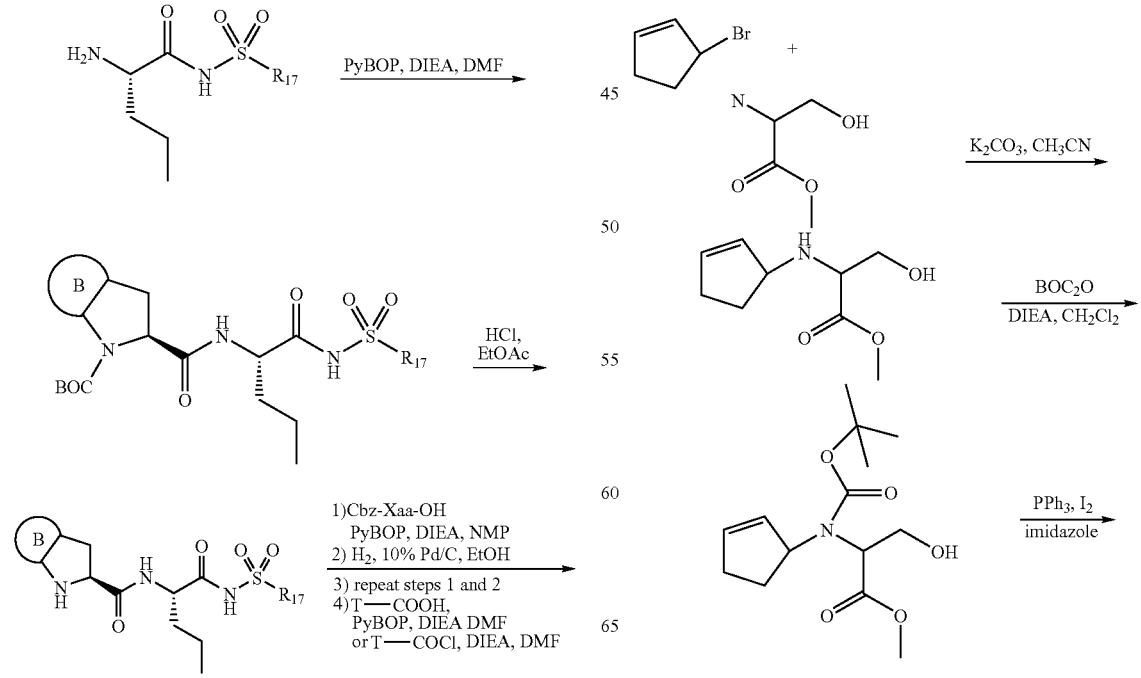

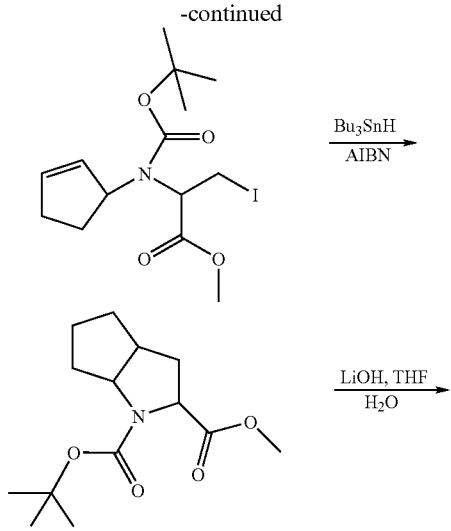
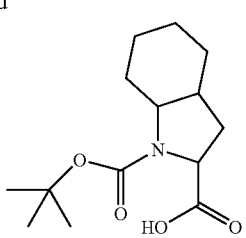
Scheme 1 or 2 in combination with scheme 4 above provides another general method for the preparation of compounds of formula I, formula II, or formula IV.
Scheme 5:
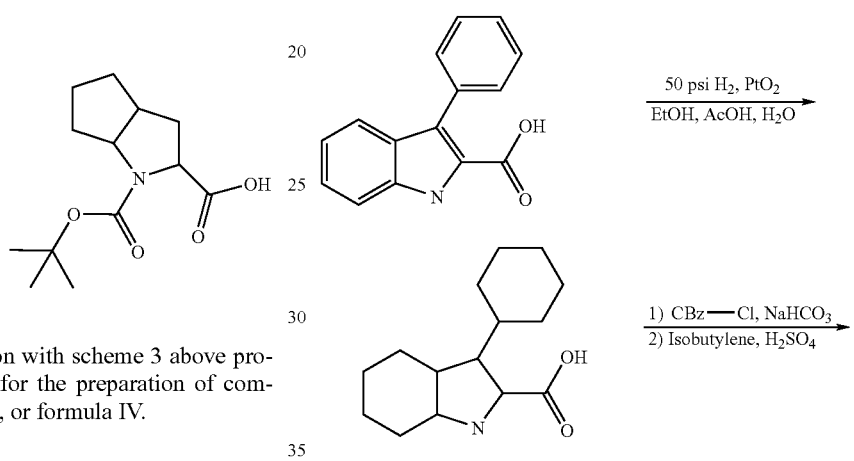
Scheme 1 or 2 in combination with scheme 3 above provides another general method for the preparation of compounds of formula I, formula II, or formula IV.
Scheme 4:
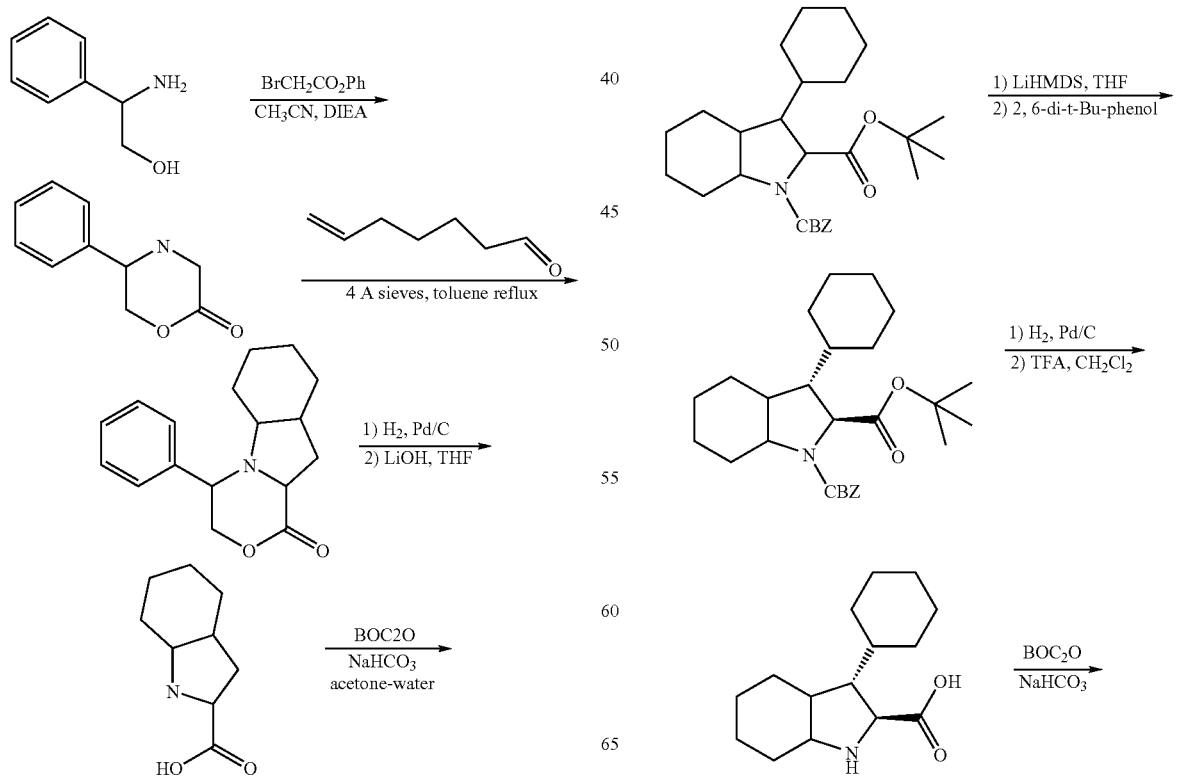

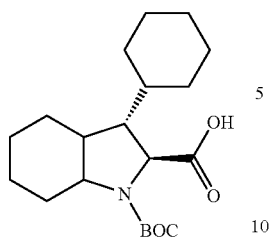

Scheme 1 or 2 in combination with scheme 5 above provides another general method for the preparation of certain compounds of formula I, formula II, or formula IV.

Scheme 6:

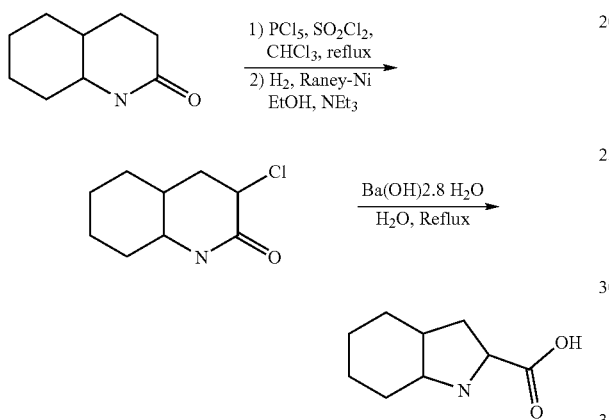

Scheme 1 or 2 in combination with scheme 6 above provides another general route for the preparation of compounds of formula I, formula II, or formula IV.

Scheme 7:

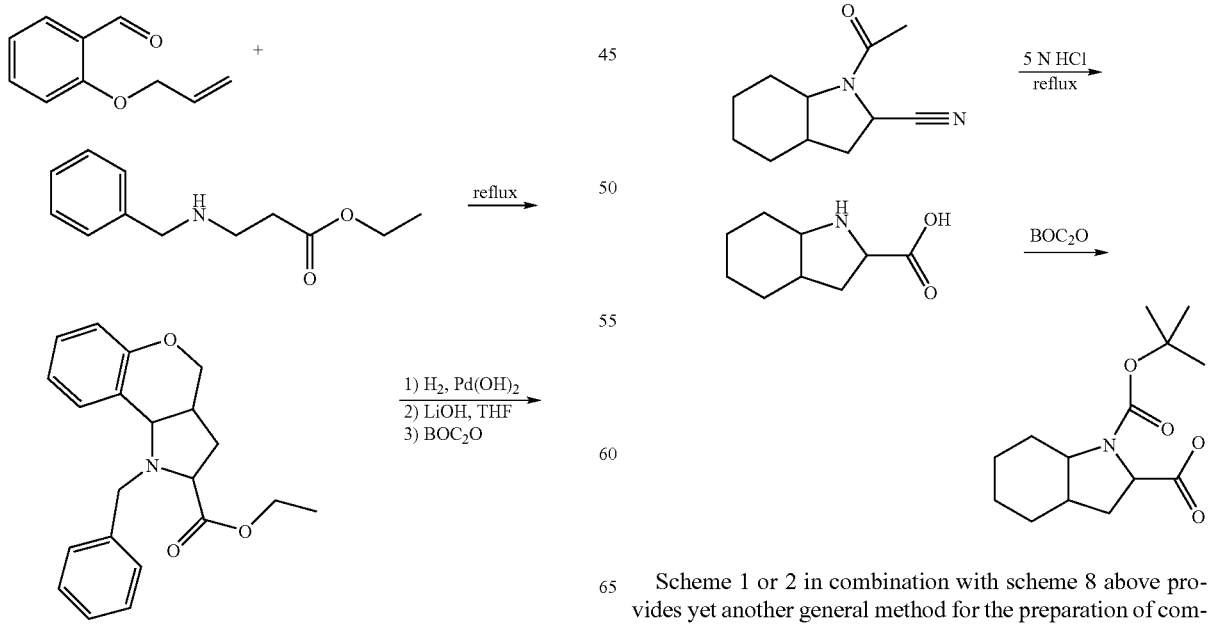

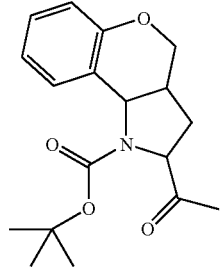

Scheme 1 or 2 in combination with scheme 7 above provides another general method for the preparation of certain compounds of formula I, formula II, or formula IV.

Scheme 8:

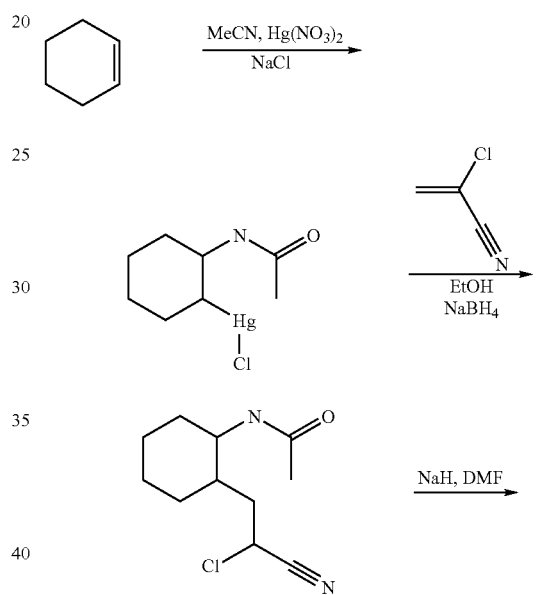

Scheme 1 or 2 in combination with scheme 8 above provides yet another general method for the preparation of compounds of formula I, formula II, or formula IV.

Scheme 9:

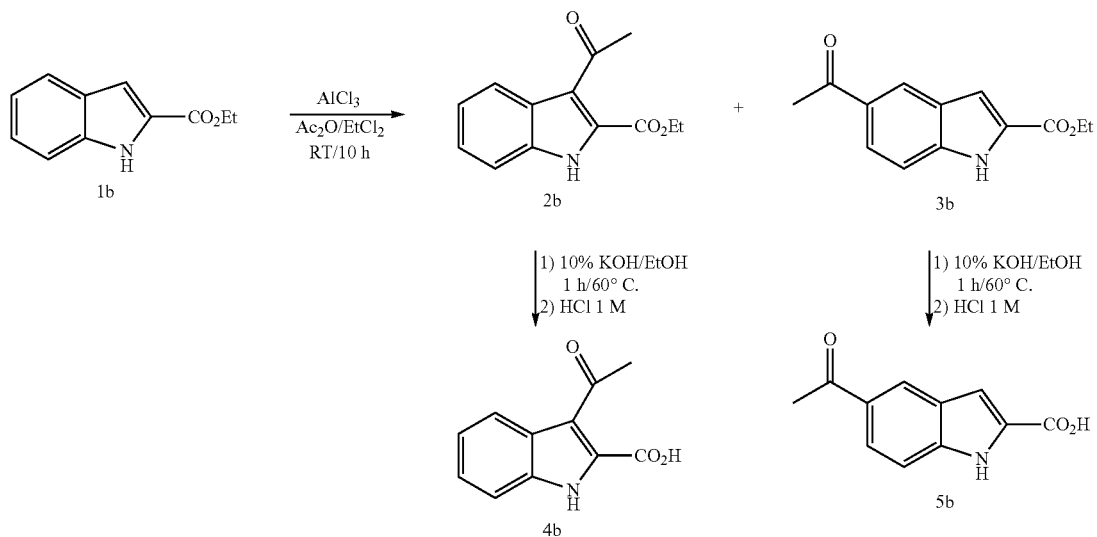

Scheme 1 or 2 in combination with scheme 9 above provides a general method for the preparation of compounds of formula I, formula II, or formula IV.

Scheme 10:

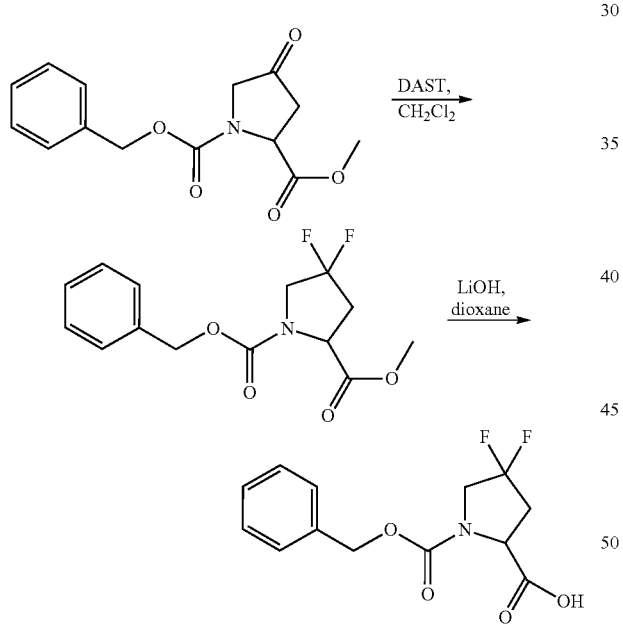

Scheme 1 or 2 in combination with scheme 10 above provides a general method for the preparation of compounds of formula I, formula II, or formula IV.

Scheme 11:

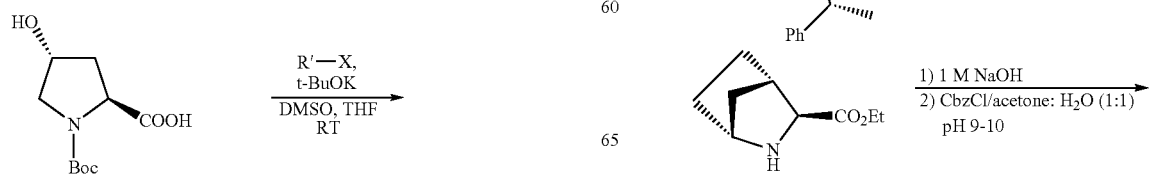

-continued

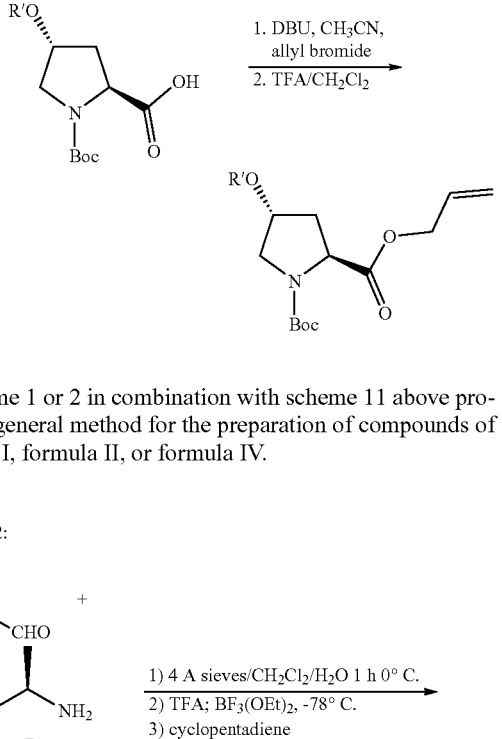

Scheme 1 or 2 in combination with scheme 11 above provides a general method for the preparation of compounds of formula I, formula II, or formula IV.

Scheme 12:

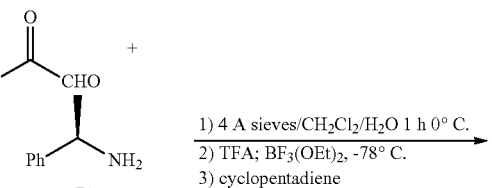

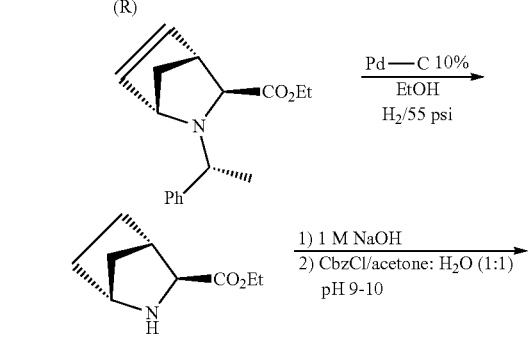

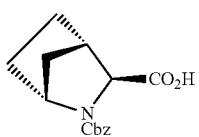

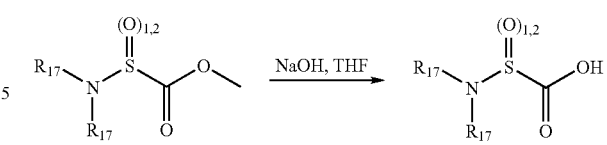

Scheme 12 depicts a synthetic route for another P2 of interest. Scheme 1 or 2 in combination with scheme 12 above provides a general method for the preparation of compounds of formula I, formula II, or formula IV.

Scheme 13:

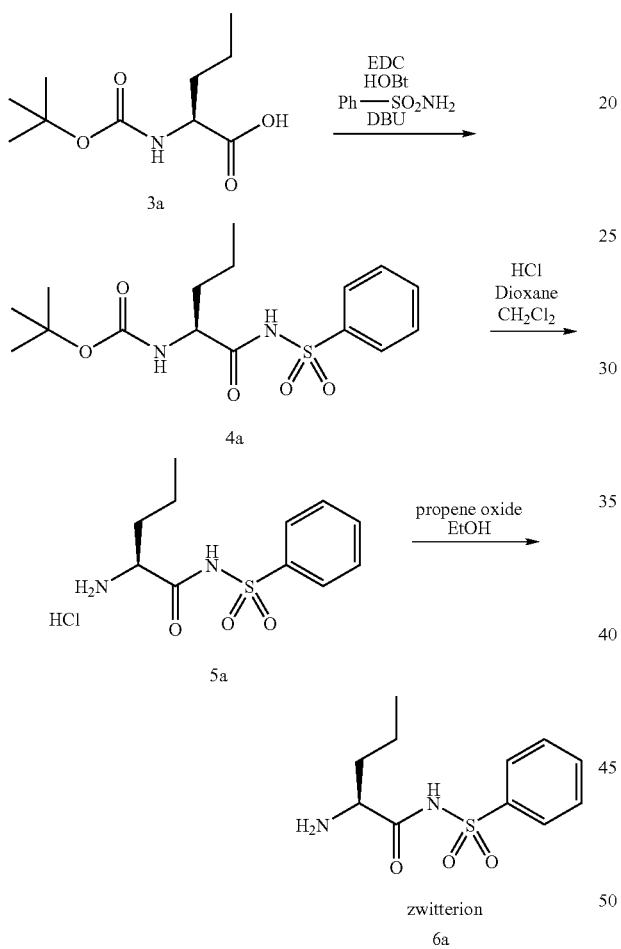

Scheme 14 above provides a general route for the preparation of compounds wherein V—R-T is as shown above and $R_{17}$ is as described in any of the embodiments herein. Therein, commercially available amine and sulfonyl chloride is condensed and then hydrolyzed under basic conditions to provide an intermediate acid. The acid may be further converted to compounds of formula I or formula IV using the methods outlined in scheme 1 or 2.

Scheme 15:

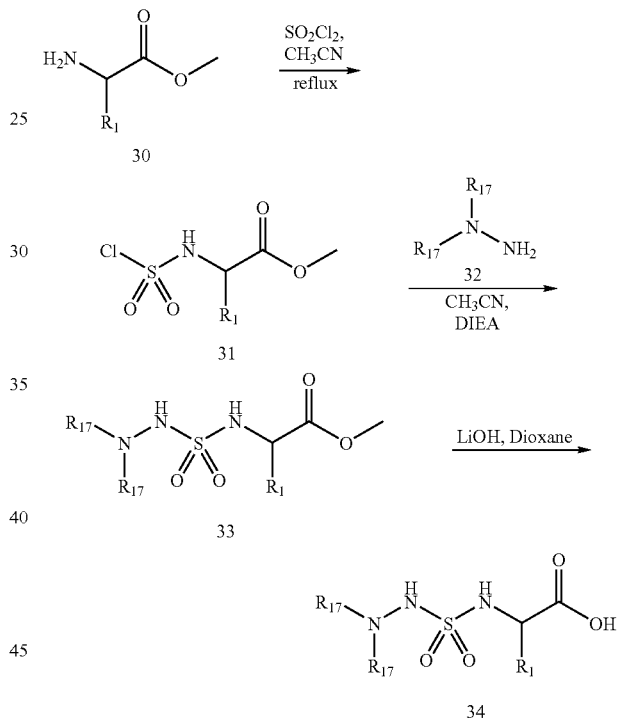

Scheme 13 above provides a synthetic scheme for the preparation of amino sulfonamide 6a using the procedures described in *Bioorg. & Med. Chem.*, 11, pp. 2551-2568 (2003).

Scheme 14:

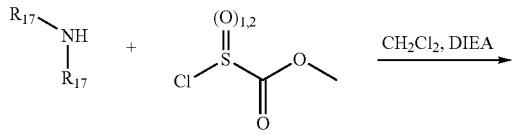

Scheme 15 above provides a general route for the preparation of compounds or formula I, wherein V—R-T is as depicted above, and $R_{17}$ and $R_1$ as described in any of the embodiments herein. Therein, commercially available amino acid ester 30 is converted to the corresponding N-chlorosulfonyl ester 31 according to the procedure described by Kempf, D. J. et al., *J. Med. Chem.*, pp. 320-330 (1993). Coupling of 31 with commercially available hydrazine 32 followed by hydrolysis yields acid 34. Acid 34 may be converted to compounds of formula I using the methods outlined in schemes 1 and 2 above. It will be appreciated by one of skill in the art that compounds of formula IV may be prepared according to this procedure and those depicted in schemes 1 and 2 by using the appropriate starting material. For instance, in the scheme detailed above, $R_1$ in compound 30 would replaced by $R_{13}$ wherein $R_{13}$ is as described in any of the embodiments herein.

Scheme 16:

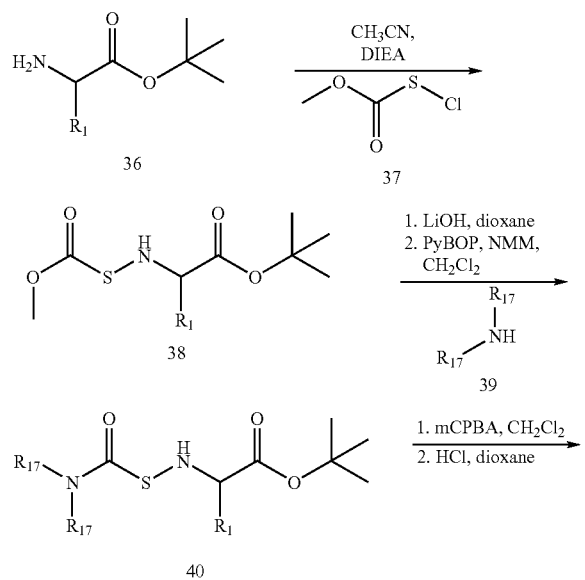

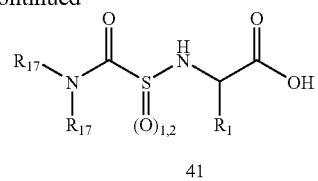

Scheme 16 above provides a general route for the preparation of compounds wherein V—R-T is as depicted above, and $R_{17}$ and $R_1$ as described in any of the embodiments herein. Chloroester 37 is prepared according to the methods described in *J. Org. Chem.*, pp. 2624-2629 (1979). Coupling of commercially available amino t-butyl ester 36 with chloride 37 gives sulfonamide 38. Basic hydrolysis of mixed ester 38 followed by coupling with commercially available amine 39 affords intermediate ester 40. Oxidation with one equivalent of mCBPA affords sulfoxide 41, wherein V is $—S(O)_1—$. Alternatively, oxidation with two equivalents of mCBPA affords sulfone 41, wherein V is $—S(O)_2—$. Acidic hydrolysis of t-butyl ester 40 yields acid 41, which can be further elaborated to compounds of formula I or formula II according to the procedures outlined above in schemes 1 and 2. It will be appreciated by one of skill in the art that compounds of formula IV may be prepared according to this procedure and those depicted in schemes 1 and 2 by using the appropriate starting material. For instance, in the scheme detailed above, $R_1$ in compound 36 would replaced by $R_{13}$ wherein $R_{13}$ is as described in any of the embodiments herein.

Scheme 17:

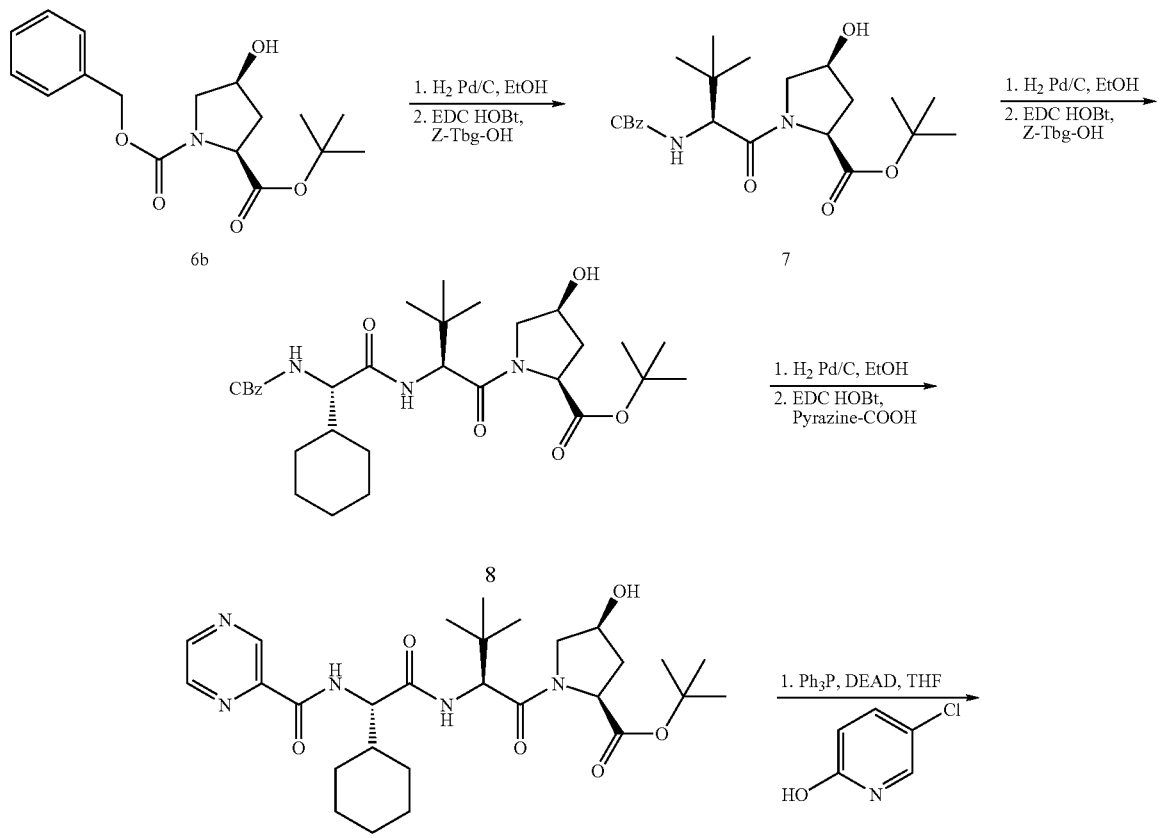

-continued
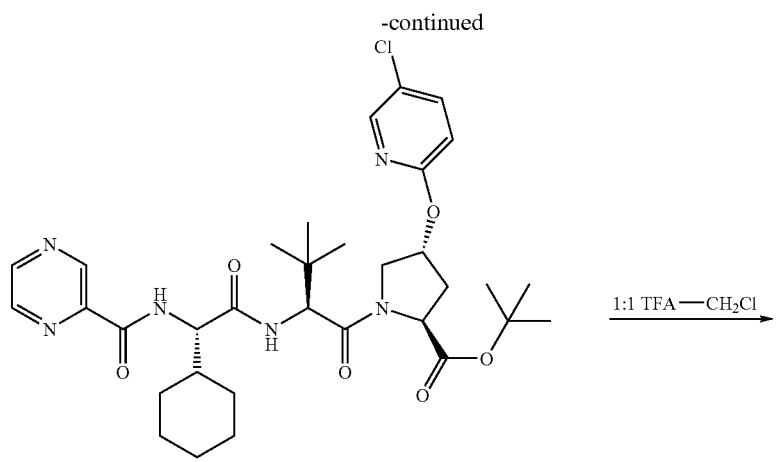
10
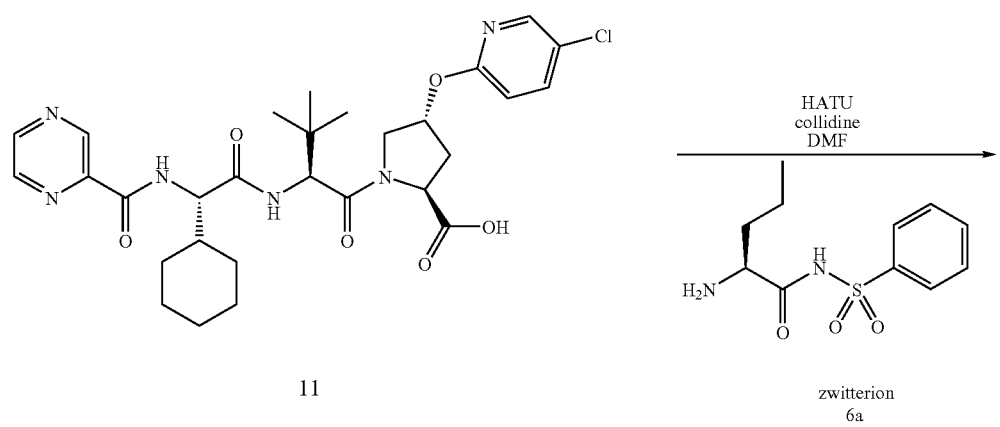
11
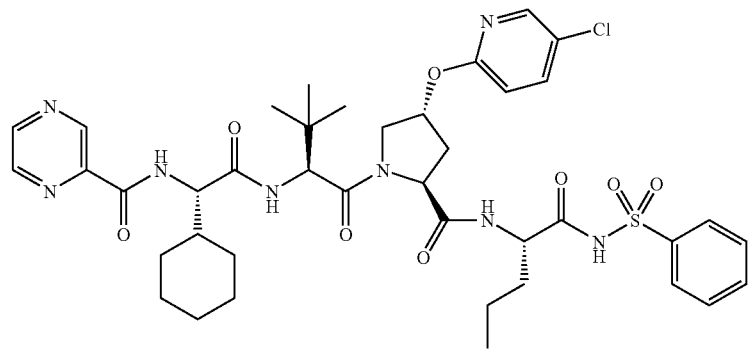
2

Scheme 17 above provides a route for the preparation of compound 2 from commercially available starting materials (6b).
Scheme 18:
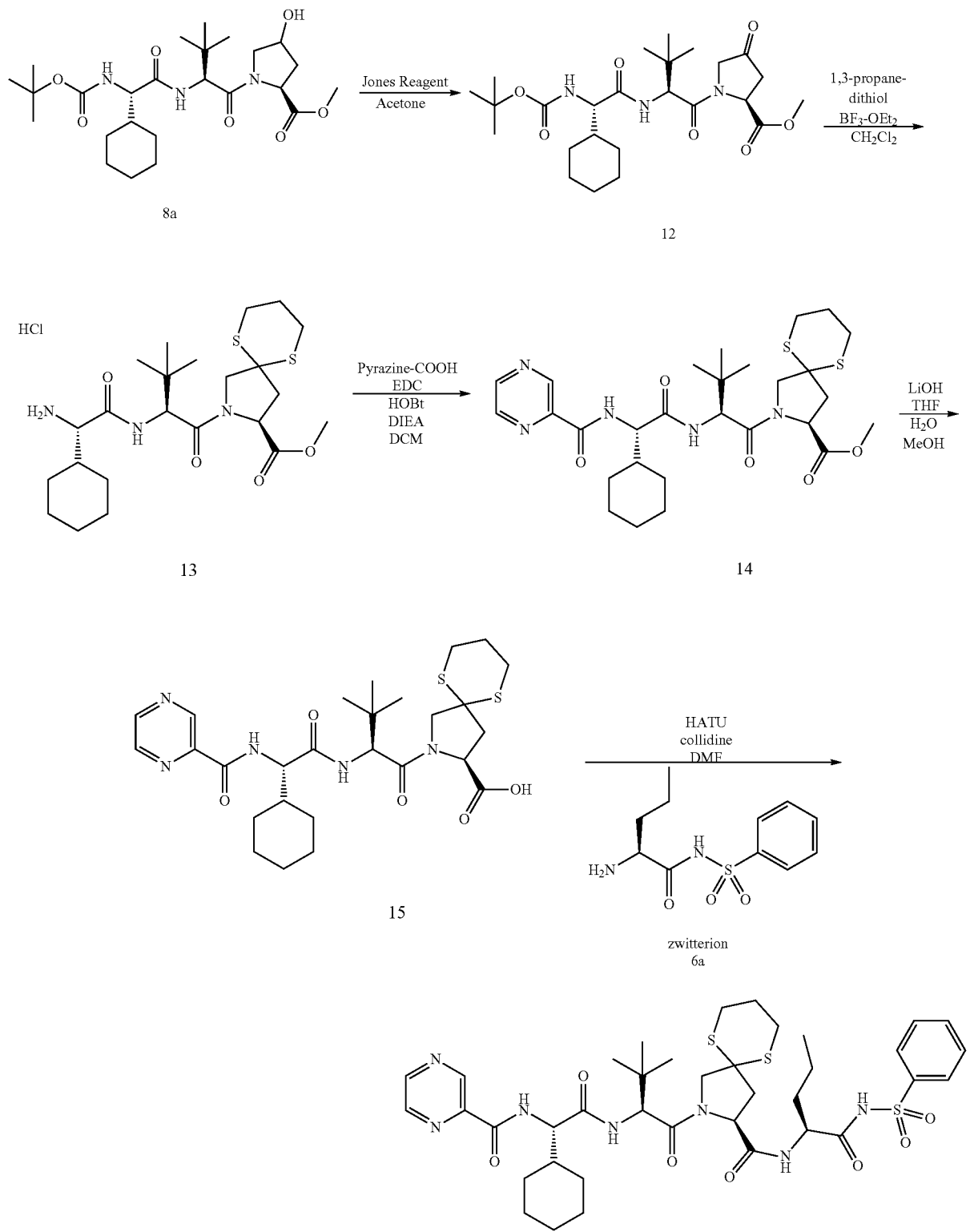

Scheme 18 above provides a route for the preparation of compound 1 from intermediate 8a. Intermediate 8a is prepared according to the procedures listed in scheme 17 using the appropriate Boc protected amino acids instead of the Cbz protected amino acids.

Scheme 19:

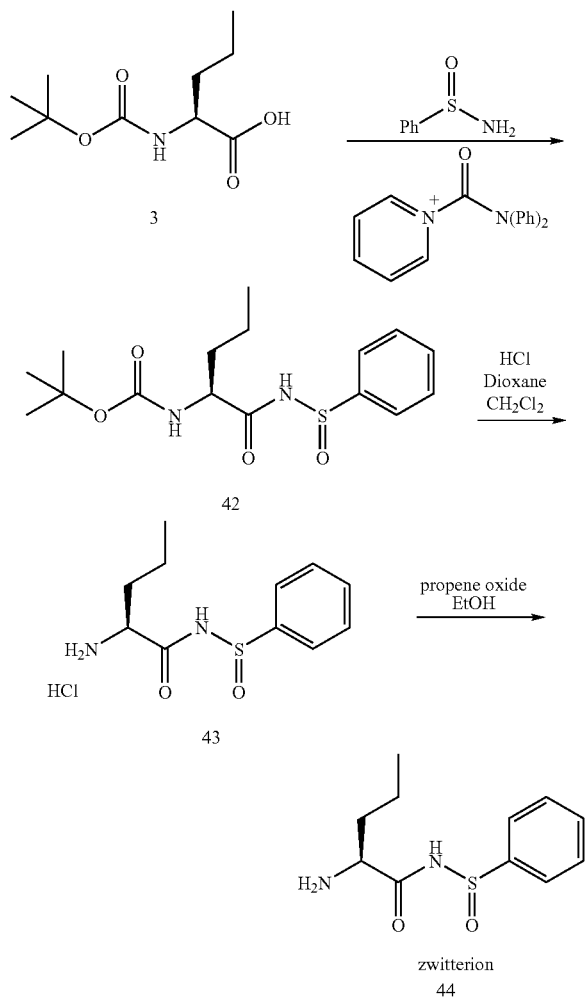

Scheme 19 above provides a synthetic scheme for the preparation of amino sulfinamide intermediate 44 using the procedures described in *J. Med. Chem.*, 33(9), pp. 2437-2451 (1990). Intermediate 44 may be further converted to compounds of formula I, formula II, or formula IV using the methods outlined in scheme 1 or 2.

The preparation of various other optionally substituted multicyclic azaheterocyclyl intermediates to prepare compounds of formula I, formula II or formula IV via schemes 1 and 2 above, may be accomplished by the methods described in PCT publication No. WO 02/18369 and references cited therein.

Various 3, 4, and 5-substituted proline analogues may either be purchased commercially or prepared according to known literature procedures. For instance, certain 3-substituted proline analogues of interest may be prepared according to the method of Holladay, M. W. et al., *J. Med. Chem.*, 34, pp. 457-461 (1991). Additionally various 3,4-disubstituted proline analogues may be prepared according to the method of Kanamasa, S. et al., *J. Org. Chem,* 56, pp. 2875-2883 (1991). In each of the syntheses involving 3, 4, or 5-substituted prolines or 3,4-disubstituted prolines, the intermediates may be further elaborated by the routes defined above in schemes 1 or 2 to prepare compounds of formula I, formula II, or formula IV.

Although certain embodiments are depicted and described below, it will be appreciated that compounds of this invention can be prepared according to the methods described generally above using appropriate starting materials generally available to one of ordinary skill in the art.

Another embodiment of this invention provides a pharmaceutical composition comprising a compound of formula I, formula II or formula IV or pharmaceutically acceptable salts or mixtures of salts thereof. According to another embodiment, the compound of formula I, of formula II or of formula IV is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to another embodiment, the compositions of this invention are formulated for pharmaceutical administration to a mammal. In one embodiment said mammal is a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In one embodiment, dosage levels of between about 0.01 and about 100 mg/kg body weight per day of the protease inhibitor compounds described herein are useful in a monotherapy for the prevention and treatment of antiviral, particularly anti-HCV mediated disease. In another embodiment, dosage levels of between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention. will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). In one embodiment, such preparations contain from about 20% to about 80% active compound.

When the compositions of this invention comprise a combination of a compound of either formula I, formula II, or formula IV and one or more additional therapeutic or prophylactic agents, both the compound and the additional agent should be present at dosage levels of between about 10 to 100% of the dosage normally administered in a monotherapy regimen. In another embodiment, the additional agent should be present at dosage levels of between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the pharmaceutical compositions are formulated for oral administration.

In another embodiment, the compositions of this invention additionally comprise another anti-viral agent, preferably an anti-HCV agent. Such anti-viral agents include, but are not limited to, immunomodulatory agents, such as α-, β-, and γ-interferons, pegylated derivatized interferon-αcompounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above. See also W. Markland et al., *Antimicrobial & Antiviral Chemotherapy,* 44, p. 859 (2000) and U.S. Pat. No. 6,541,496.

VX-497

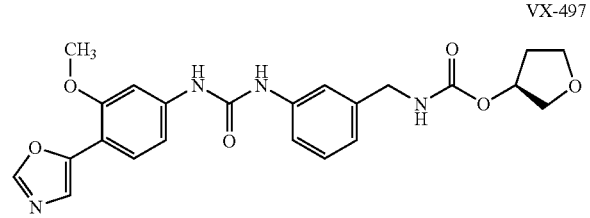

The following definitions are used herein (with trademarks referring to products available as of this application's filing date).

"Peg-Intron" means PEG-INTRON®, peginteferon alfa-2b, available from Schering Corporation, Kenilworth, N.J.;

"Intron" means INTRON-A®, interferon alfa-2b available from Schering Corporation, Kenilworth, N.J.;

"ribavirin" means ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition; also available as REBETROL® from Schering Corporation, Kenilworth, N.J., or as COPEGASUS® from Hoffmann-La Roche, Nutley, N.J.;

"Pagasys" means PEGASYS®, peginterferon alfa-2a available Hoffmann-La Roche, Nutley, N.J.;

"Roferon" mean ROFERON®, recombinant interferon alfa-2a available from Hoffmann-La Roche, Nutley, N.J.;

"Berefor" means BEREFOR®, interferon alfa 2 available from Boehringer Ingelheim Pharmaceutical, Inc., Ridgefield, Conn.;

SUMIFERON®, a purified blend of natural alpha interferons such as Sumiferon available from Sumitomo, Japan;

WELLFERON®, interferon alpha nl available from Glaxo_Wellcome LTd., Great Britain;

ALFERON®, a mixture of natural alpha interferons made by Interferon Sciences, and available from Purdue Frederick Co., Conn.;

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

According to one embodiment of the present invention, the interferon is α-interferon. According to another embodiment, a therapeutic combination of the present invention utilizes natural alpha interferon 2a. Or, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include:

(a) INTRON-A® (interferon-alpha 2B, Schering Plough),
(b) PEG-INTRON®,
(c) PEGASYS®,
(d) ROFERON®,
(e) BEREFOR®,
(f) SUMIFERON®,
(g) WELLFERON®,
(h) consensus alpha interferon available from Amgen, Inc., Newbury Park, Calif.,
(i) ALFERON®;
(j) VIRAFERON®;
(k) INFERGEN®.

As is recognized by skilled practitioners, a protease inhibitor would be preferably administered orally. Interferon is not typically administered orally. Nevertheless, nothing herein limits the methods or combinations of this invention to any specific dosage forms or regime. Thus, each component of a combination according to this invention may be administered separately, together, or in any combination thereof.

In one embodiment, the protease inhibitor and interferon are administered in separate dosage forms. In one embodiment, any additional agent is administered as part of a single dosage form with the protease inhibitor or as a separate dosage form. As this invention involves a combination of compounds, the specific amounts of each compound may be dependent on the specific amounts of each other compound in the combination. As recognized by skilled practitioners, dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, interferon-alph 2B (INTRON-A®, Schering Plough); REBETRON® (Schering Plough, Inteferon-alpha 2B+Ribavirin); pegylated interferon alpha (Reddy, K. R. et al. "Efficacy and Safety of Pegylated (40-kd) interferon alpha-2a compared with interferon alpha-2a in noncirrhotic patients with chronic hepatitis C (*Hepatology,* 33, pp. 433-438 (2001); consensus interferon (Kao, J. H., et al., "Efficacy of Consensus Interferon in the Treatement of Chronic Hepatitis" *J. Gastroenterol. Hepatol.* 15, pp. 1418-1423 (2000), interferon-alpha 2A (Roferon A; Roche), lymphoblastoid or "natural" interferon; interferon tau (Clayette, P. et al., "IFN-tau, A New Interferon Type I with Antiretroviral activity" *Pathol. Biol.* (Paris) 47, pp. 553-559 (1999); interleukin 2 (Davis, G. L. et al., "Future Options for the Management of Hepatitis C." *Seminars in Liver Disease,* 19, pp. 103-112 (1999); Interleukin 6 (Davis et al. "Future Options for the Management of Hepatitis C." *Seminars in Liver Disease* 19, pp. 103-112 (1999); interleukin 12 (Davis, G. L. et al., "Future Options for the Management of Hepatitis C." *Seminars in Liver Disease,* 19, pp. 103-112 (1999); Ribavirin; and compounds that enhance the development of type 1 helper T cell response (Davis et al., "Future Options for the Management of Hepatitis C." *Seminars in Liver Disease,* 19, pp. 103-112 (1999). Interferons may ameliorate viral infections by exerting direct antiviral effects and/or by modifying the immune response to infection. The antiviral effects of interferons are often mediated through inhibition of viral penetration or uncoating, synthesis of viral RNA, translation of viral proteins, and/or viral assembly and release.

Compounds that stimulate the synthesis of interferon in cells (Tazulakhova, E. B. et al., "Russian Experience in Screening, analysis, and Clinical Application of Novel Interferon Inducers" *J. Interferon Cytokine Res.*, 21 pp. 65-73) include, but are not limited to, double stranded RNA, alone or in combination with tobramycin, and Imiquimod (3M Pharmaceuticals; Sauder, D. N. "Immunomodulatory and Pharmacologic Properties of Imiquimod" *J. Am. Acad. Dermatol.*, 43 pp. S6-11 (2000).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11).

This invention may also involve administering a cytochrome P450 monooxygenase inhibitor. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole. For preferred dosage forms of ritonavir, see U.S. Pat. No. 6,037,157, and the documents cited therein: U.S. Pat. No. 5,484,801, U.S. application Ser. No. 08/402,690, and International Applications WO 95/07696 and WO 95/09614).

Methods for measuring the ability of a compound to inhibit cytochrome P450 monooxygenase activity are known (see U.S. Pat. No. 6,037,157 and Yun, et al. *Drug Metabolism & Disposition*, vol. 21, pp. 403-407 (1993).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. In one embodiment, the methods of this invention are used to treat a patient suffering from a HCV infection. Such treatment may completely eradicate the viral infection or reduce the severity thereof. In another embodiment, the patient is a human being.

In an alternate embodiment, the methods of this invention additionally comprise the step of administering to said patient an anti-viral agent preferably an anti-HCV agent. Such antiviral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including but not limited to helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. In one embodiment, the viral serine protease isolated by this method is HCV NS3-NS4A protease.

In order that this invention be more fully understood, the following preparative and testing examples are set forth. These examples are for the purpose of illustration only and are not to be construed as limiting the scope of the invention in any way.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_f$(min)" refers to the HPLC retention time, in minutes, associated with the compound. The HPLC retention times listed were either obtained from the mass spec. data or using the following method:
Instrument: Hewlett Packard HP-1050;
Column: YMC $C_{18}$ (Cat. No. 326289C46);
Gradient/Gradient Time: 10-90% $CH_3CN/H2O$ over 9 minutes, then 100% $CH_3CN$ for 2 minutes;
Flow Rate: 0.8 ml/min;
Detector Wavelength: 215 nM and 245 nM.

Chemical naming for selected compounds herein was accomplished using the naming program provided by Cambridge Soft Corporations ChemDraw Ultra®, version 7.0.1.

Example 1

Preparation of compounds 4b and 5b:

Aluminum chloride (7.75 g, 0.058 mol) was suspended in 200 ml of anhydrous dichloroethane at room temp. followed by a slow addition of acetic anhydride (2.74 mL, 0.03 mol). The mixture was stirred at room temp for 10 minutes after which, 1H-indole-2-carboxylic acid ethyl ester (1b, 5.0 g, 0.0264 mol) was added as a solution in 15 mL of dichloroethane. The reaction mixture was stirred under nitrogen at 40° C. for 10 h. The reaction was quenched with an ice-water mixture and the organic layer was washed with water (3×). The organic phase was dried over anh. $Na_2SO_4$, filtered and concentrated in vacuo. Chromatography on $SiO_2$ (4% Ethyl acetate/96% $CH_2Cl_2$) provided 3.2 g of 3-acetyl-1H-indole-2-carboxylic acid ethyl ester 2b (52%) and 770 mg of 5-acetyl-1H-indole-2-carboxylic acid ethyl ester 3b (13%).

2b: $^1$H NMR (CDCl$_3$) δ 9.1 (bs, 1H), 8.1 (d, 1H), 7.5 (m, 2H), 7.3 (s, 1H), 4.4 (q, 2H), 2.7 (s, 3H), 1.5 (t, 3H) ppm.

3b: $^1$H NMR (CDCl$_3$) δ 9.3 (bs, 1H), 8.25 (s, 1H), 8.1 (d, 1H), 7.6 (d, 1H), 7.2 (s, 1H), 4.3 (q, 2H), 2.7 (s, 3H), 1.7 (t, 3H) ppm.

Saponification of 2b and 3b with 10% KOH in ethanol at 60° C. for 1 h followed by acidification with 1M HCl provided 3-acetyl-1H-indole-2-carboxylic acid 4b and 5-acetyl-1H-indole-2-carboxylic acid 5b in 95% and 93% yield respectively. The crude acids were used directly without further purification.

Example 2

Preparation of compound 6a:

Commercially available compound 3 (1.0 g, 1.0 eq) stirred in 20 mL of $CH_2Cl_2$ was treated with EDC (2.21 g, 2.5 eq), and HOBt (1.76 g, 2.5 eq). After activation, benzene sulfonamide (1.45 g, 2.0 eq) and DBU (1.38 mL, 2.0 eq) were added and the mixture was stirred for 5 hours. Ethyl acetate was added and the organics were washed with 1.0N HCl, followed by brine, dried over sodium sulfated, filtered, and concentrated. Silica gel purification eluting with 5% MeOH/$CH_2Cl_2$ yielded 1.2 g (73%) of sulfonamide 4 as a white solid with consistent analytical data. FIA M+H=357.2 M−H=355.2

$^1$H NMR (d$_6$ DMSO) δ 7.60 (m, 5H), 4.80 (m, 1H), 1.70 (m, 2H), 1.40 (s, 9H), 1.20 (m, 2H), 0.90 (t, 3H) ppm.

Boc-protected sulfonamide 4 (500 mg, 1.0 eq) in 10 mL $CH_2Cl_2$ was treated with 3.5 mL of 4N HCl/Dioxane (10 eq) and stirred for 3 hours. The reaction mixture was then concentrated in vacuo to give crude amine 5 which was used without further purification.

Crude amine 5 in 15 mL of EtOH was treated with propylene oxide (1.45 mL, 11.0 eq) and heated to 50 degrees. After 3 hours, desired zwitterionic amine 6a 300 mg (83%, 2 steps) was obtained as a white solid.

$^1$H NMR (d$_6$ DMSO) δ 7.80 (d, 2H), 7.40 (m, 3H), 3.30 (m, 1H), 1.65 (m, 1H), 1.55 (m, 1H), 1.30 (m, 2H), 0.80 (s, 3H) ppm.

Example 3

Preparation of compound 2:

Commercially available (Bachem) Z-Hydroxy-proline (10 g, 42.51 mmols) was dissolved 90 mls of THF (tetrahydrofuran) and was cooled to 0° C. with an ice water bath. To this was added previously prepared tert-butyl N,N'-diisopropyl-imidocarbamate (27 ml, 135 mmol) via a dropping funnel over 30 minutes. After addition the cooling bath was removed and the reaction stirred at ambient temperature for 24 hours. The volume of the reaction was reduced and then diethyl ether was added prior to washing with saturated sodium bicarbonate, then 0.5M hydrochloric acid, then water, and finally with brine. The organic layer was dried with sodium sulfate and concentrated in vacuo to give 15 g of crude material. Material was run through a plug of SiO2 and eluted with 45% EtOAc-Hexanes to give tert-butyl ester 6b as a colorless oil 11.0 g (81%)

$^1$H NMR (CDCl3, ppm) δ 7.35 (m, 5H), 5.2 (m, 2H), 4.3 (m, 2H), 4.65 (m, 3H), 2.35 (m, 1H), 2.1 (t, 1H), 1.35, 1.55 (rotomers, 1.45, 9H) ppm.

Mixed 6b in EtOH, and added catalytic amount of 10% Pd on carbon, then stirred under 1 atmosphere of hydrogen using a balloon. After 12 hours the reaction was shown to be complete by tlc, and the catalyst was filtered and washed with EtOH. The filtrate was concentrated and dried under high vacuum to give the amine as a yellow solid, which was carried on into the next step. Z-Tbg-OH (8.3 g, 31.1 mmols) was dissolved in NMP and to it was added EDC (6.0 g, 31.1 mmols), HOBT (4.2 g, 31.1 mmols), DMAP (340 mgs, 2.8 mmols), and cooled to 0° C. using and ice-water bath. To this mixture was added the amine as a solution in NMP, and the reaction was stirred for 2 days. The reaction was poured over ice and acidified with 0.5N hydrochloric acid to pH 5, and then extracted with EtOAc. The organic extracts were washed with saturated sodium bicarbonate, then water, and finally with brine. The organic layer was dried with sodium sulfate and concentrated in vacuo to give 14.8 g of crude material. Purification was carried out using chromatography on $SiO_2$, eluting with 50% EtOAc—Hexanes. Concentration of the homogeneous fractions yielded 10.5 grams of 7 as a colorless foam (85%) which was used as is in the next step.

To a mixture of 7 (10.5 g, 24.16 mmol) in EtOH, was added a catalytic amount of 10% Pd on carbon, then stirred under 1 atmosphere of hydrogen using a balloon. After 12 hours the reaction was shown to be complete by tlc, and the catalyst was filtered and washed with EtOH. The filtrate was concentrated and dried under high vacuum to give the amine as a yellow solid, which was carried on into the next step. Z-Chg-OH (7.7 g, 26.6 mmols) was dissolved in NMP and to it was added EDC (5.1 g, 26.7 mmols), HOBT (3.6 g, 26.6 mmols), and cooled to 0° C. using and ice-water bath. To this mixture was added the previously prepared amine as a solution in NMP, and the reaction was stirred for 2 days. The reaction was poured over ice and brine, and then extracted with EtOAc. The organic extracts were washed with 0.5N hydrochloric acid, saturated sodium bicarbonate, water, and finally with brine. The organic extract was dried with sodium sulfate and concentrated in vacuo to give 15.31 g of 8 as crude material, which was used as is in the next step.

To a solution of 8 (5.6 g, 9.76 mmol) in EtOH, was added a catalytic amount of 10% Pd on carbon, then stirred under 1 atmosphere of hydrogen using a balloon. After 12 hours the reaction was shown to be complete by tlc, and the catalyst was filtered and washed with EtOH. The filtrate was concentrated and dried under high vacuum to give the amine as an amorphous solid, which was carried on into the next step. Pyrazine-2-carboxylic acid (1.45 g, 11.7 mmols) was dissolved in NMP and to it was added EDC (2.24 g, 11.7 mmols), HOBT (1.34 g, 11.7 mmols), and cooled to 0° C. using and ice bath. To this mixture was added the previously prepared amine as a solution in NMP, and the reaction was stirred for 2 days. The reaction was poured over ice and brine, and then extracted with EtOAc. The organic extracts were washed with 0.5N hydrochloric acid, saturated sodium bicarbonate, water, and finally with brine. The organic extract was dried with sodium sulfate and concentrated in vacuo to give 5.3 g (99%) of 9 as a colorless foam, which was used as is in the next step.

To a solution of 9 (0.15 g, 0.28 mmols) in anhydrous THF was added triphenylphosphine (0.131 g, 0.5 mmols), 2-hydroxy-4-chloro-pyridine (65 mgs, 0.5 mmols), and last was added the diethyl azodicarboxylate (0.100 mL, 1.85 mmols). The reaction was stirred at room temperature for 18 hours or until the reaction showed no 8 remaining by HPLC. THF was removed from the reaction and then the material was taken up in EtOAc, and washed with 0.1N NaOH, 0.5N hydrochloric acid, water, and finally with brine. The organic extract was dried with sodium sulfate and concentrated in vacuo to give the crude tert-butyl ester 10, which was used as is in the next step.

The tert-butyl ester 10 was hydrolyzed to the carboxylic acid by treatment with 50% trifluoroacetic acid in dichloromethane for 3 hours. The solvent was removed under vacuum, and then the residue was taken up with 0.1N NaOH, and washed with EtOAc. The aqueous phase was acidified with 5% citric acid, and then extracted with EtOAc. The resultant organic phase was washed with water and then brine, and then the organic extract was dried with sodium sulfate and concentrated in vacuo to give acid 11 as a colorless foam, which was used as is in the next step.

Acid 11 (25 mg, 1.0 eq) was stirred in 0.5 mL DMF and treated with sulfonamide amine 6a (13 mg, 1.2 eq), then HATU (32 mg, 2.0 eq) followed by collidine (6.6 uL, 1.2 eq). Ethyl acetate was added upon completion of the reaction and the organics were washed with 1.0N HCl and brine, dried over magnesium sulfate, filtered and concentrated. Prep HPLC yielded 25 mg (71%) of 2 as a white solid with consistent spectral data. FIA M+H=839.5, M−H=837.9.

$^1$H NMR (CDCl3) δ 9.40 (s, 1H), 8.80 (s, 1H), 8.60 (s, 1H), 8.25 (d, 1H), 8.10 (s, 1H), 8.0 (d. 2H), 7.60 (m, 1H), 7.50 (m, 3H), 7.15 (m, 1H), 6.90 (m, 1H), 6.60 (m, 1H), 5.60 (s, 1H), 4.60 (m, 2H), 4.50 (m, 1H), 4.40 (m, 1H), 4.20 (m, 1H), 4.00 (m, 1H), 1.50-1.90 (m, 9H), 1.20-1.40 (m, 5H), 1.10 (m, 3H), 1.00 (s, 9H), 0.90 (m, 1H), 0.80 (t, 3H) ppm.

Example 4

Preparation of compound 1:

Jones Reagent was prepared by mixing 94 mg sodium dichromate dihydrate with 94 uL concentrated sulfuric acid in 276 uL water. This was added to a suspension of intermediate 8a (0.5 g, 1.0 eq) in 4.5 mL acetone resulting in he orange solution turning green. Added water and extracted with ethyl acetate 3 times. The organics were washed with water and brine then dried over sodium sulfate, filtered and concentrated. Silica gel purification.(eluting with 30% ethyl acetate/ hexanes) yielded 350 mg (70%) of ketone 12 as a white solid with consistent analytical data. FIA M+H=496.2, M−H=494.3.

$^1$H NMR (CDCl3) δ 6.60 (d, 1H), 5.10 (d, 1H), 4.95 (bs, 1H), 4.40 (m, 2H), 4.10 (m, 1H), 3.90 (m, 1H), 3.80 (s, 3H), 2.95 (m, 1H), 2.65 (dd, 1H), 1.60-1.80 (m, 5H), 1.45 (s, 9H), 1.10-1.30 (m, 5H), 1.10 (S, 9H) ppm.

Ketone 12 (3.64 g, 1.0 eq) in 175 mL of $CH_2Cl_2$ was cooled in an ice bath then treated with 1,3-propanedithiol (0.798 mL, 1.1 eq) followed by slow addition of $BF_3$-$OEt_2$ (1.07 mL, 1.15 eq). The ice bath was removed and the mixture stirred while monitoring via HPLC to observe removal of the Boc group followed by formation of the dithiane. Upon completion, added 0.54 g potassium carbonate (in 8 mL water) followed by sodium bicarbonate to bring the solution to pH 8-9. Ethyl acetate waas added, the mixture washed with sodium bicarbonate solution, then water and brine. Dried over sodium sulfate, filtered and concentrated to yield 3.47 g (97%) of dithiane 13 as a white solid with consistent analytical data. FIA M+H=486.2, M−H=483.9

$^1$H NMR (CDCl3) δ 4.70 (m, 1H), 4.60 (d, 1H), 3.70 (s, 3H), 3.05 (m, 1H), 2.80 (m, 2H), 2.65 (m, 2H), 1.00-2.00 (m, 17H), 1.05 (s, 9H) ppm.

A mixture of pyrazine acid (537 mg, 1.2 eq), EDC (828 mg, 1.2 eq), and HOBt (661 mg, 1.2 eq) in 15 mL $CH_2Cl_2$ was treated 13 (free base) (1.75 g, 1.0 eq) in $CH_2Cl_2$ (3 mL) and stirred at RT for 20 minutes. Added EtOAc, washed with 1.0 N HCl, and brine, dried over sodium sulfate, filtered, and concentrated. Silica gel purification eluting with 40% ethyl acetate/hexanes yielded 1.38 g (65%) of ester 14 as a white solid. FIA M+H=592.1, M−H=590.2.

Ester 14 (40 mg, 1.0 eq)) in THF:$H_2O$:MeOH (1.0 mL:0.5 mL:0.5 mL) was treated with LiOH (5.5 mg, 2.0 eq) and stirred for 3 hours. Concentrated, added EtOAc and washed with 1.0N HCl, then brine. Dried over magnesium sulfate, filtered, and concentrated to yield 37 mg (95%) or free acid 15 as a white solid with consistent analytical data. FIA M+H=578.0, M−H=576.2.

$^1$H NMR (CDCl3) δ 9.40 (s, 1H), 8.80 (s, 1H), 8.60 (s, 1H), 8.3 (d, 1H), 6.75 (d, 1H), 4.80 (m, 2H), 4.70 (d, 1H), 4.50 (t, 1H), 3.75 (d, 1H), 3.05 (m, 1H), 2.85 (m, 1H), 2.75 (m, 1H), 2.60 (m, 1H), 2.50 (m, 1H), 1.60-2.20 (m, 9H), 1.00-1.30 (m, 5H), 1.05 (s, 9H) ppm.

Zwitterionic amine 6a (50 mg, 1.0 eq) in 0.5 mL DMF was treated with acid 15 (27 mg, 1.2 eq), then HATU (66 mg, 2.0 eq) and collidine (14 uL, 1.2 eq). Ethyl acetate was added upon reaction completion and the organics were washed with 1.0N HCl and brine, dried over magnesium sulfate, filtered and concentrated. Prep HPLC yielded 27 mg (38%) of 1 as a white solid with consistent analytical data. FIA M+H=816.5, M−H=814.7

$^1$H NMR (CDCl3) δ 8.80 (s, 1H), 8.60 (s, 1H), 8.30 (d, 1H), 8.00 (d, 2H), 7.65 (m, 1H), 7.55 (m, 3H), 7.20 (m, 1H), 6.85 (m, 1H), 4.75 (d, 1H), 4.65 (t, 1H), 4.60 (m, 1H), 4.50 (m, 1H), 3.80 (d, 1H), 3.00 (m, 2H), 2.80 (m, 1H), 2.70 (m, 1H), 2.60 (m, 1H), 2.40 (m, 1H), 2.10 (m, 1H), 1.50-2.00 (m, 8H), 1.00-1.35 (m, 6H), 1.00 (s, 9H), 0.85 (t, 3H) ppm.

Example 5

HCV Enzyme Assay Protocol

HPLC Microbore method for separation of 5AB substrate and products

Substrate:
$NH_2$-Glu-Asp-Val-Val-(alpha)Abu-Cys-Ser-Met-Ser-Tyr-COOH

A stock solution of 20 mM 5AB (or concentration of your choice) was made in DMSO w/0.2M DTT. This was stored in aliquots at −20° C.

Buffer: 50 mM HEPES, pH 7.8; 20% glycerol; 100 mM NaCl

Total assay volume was 100 μL

| Reagent | X1 (μL) | conc. in assay |
|---|---|---|
| Buffer | 86.5 | see above |
| 5 mM KK4A | 0.5 | 25 μM |
| 1 M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30° C. for ~5-10 min.

2.5 μL of appropriate concentration of test compound was dissolved in DMSO (DMSO only for control) and added to each well. This was incubated at room temperature for 15 min.

Initiated reaction by addition of 20 μL of 250 μM 5 AB substrate (25 μM concentration is equivalent or slightly lower than the Km for 5 AB).

Incubated for 20 min at 30° C.

Terminated reaction by addition of 25 μL of 10% TFA

Transferred 120 μL aliquots to HPLC vials

Separated SMSY product from substrate and KK4A by the following method:

Microbore Separation Method:
Instrumentation: Agilent 1100
Degasser G1322A
Binary pump G1312A
Autosampler G1313A
Column thermostated chamber G1316A
Diode array detector G1315A
Column
Phenonex Jupiter; 5 micron C18; 300 angstroms; 150×2 mm; P/O
00F-4053-B0
Column thermostat: 40 C
Injection volume: 100 μL
Solvent A=HPLC grade water+0.1% TFA
Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

Compounds with Ki's ranging from below 1 μM to 1 μM are designated A. Compounds with Ki's ranging from 1 μM to 5 μM are designated B. Compounds with Ki's above 5 μM are designated C. Table 1 below depicts Mass Spec., HPLC, $^1$H-NMR, and $K_i$ data for certain compounds of the invention. "ND" means no data. $^1$H-NMR spectra were recorded at 500 MHz using a Bruker AMX 500 instrument.

TABLE 1

| Compound | LC/MS (M + H) | LC/MS $R_t$(min) | FIA/MS | $^1$H-NMR: solvent | Ki range |
|---|---|---|---|---|---|
| 1 | 816.5 | 4.26 | 816.50 | CDCl$_3$ | C |
| 2 | 839.2 | 4.30 | ND | CDCl$_3$ | C |
| 3 | ND | ND | 873.60 | CDCl$_3$ | B |

We claim:
1. A compound of formula I:

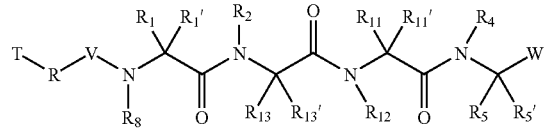

or a pharmaceutically acceptable salt or mixtures thereof, wherein:
V is —C(O)—;
R is a bond;
T is:

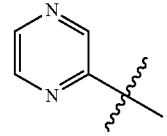

J is halogen, —OR', —OC(O)N(R')$_2$, —NO$_2$, —CN, —CF$_3$, —OCF$_3$, —R', oxo, thioxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R)C(O)OR', —N(R')C(O)R', —N(R)C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'), wherein;
two R' groups together with the atoms to which they are bound form a 3- to 10- membered aromatic or non-aromatic ring system having up to 3 heteroatoms independently selected from N, NH, O, S, SO, or SO$_2$, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from J$_2$;
each R' is independently selected from:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, or
(C5-C10)-heteroaryl-(C1-C12)-aliphatic-, wherein R' has up to 3 substituents selected independently from $J_2$;

$J_2$ is halogen, —OR', —OC(O)N(R')$_2$, —NO$_2$, —CN, —CF$_3$, —OCF$_3$, —R', oxo, thioxo, 1,2-methylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'); or

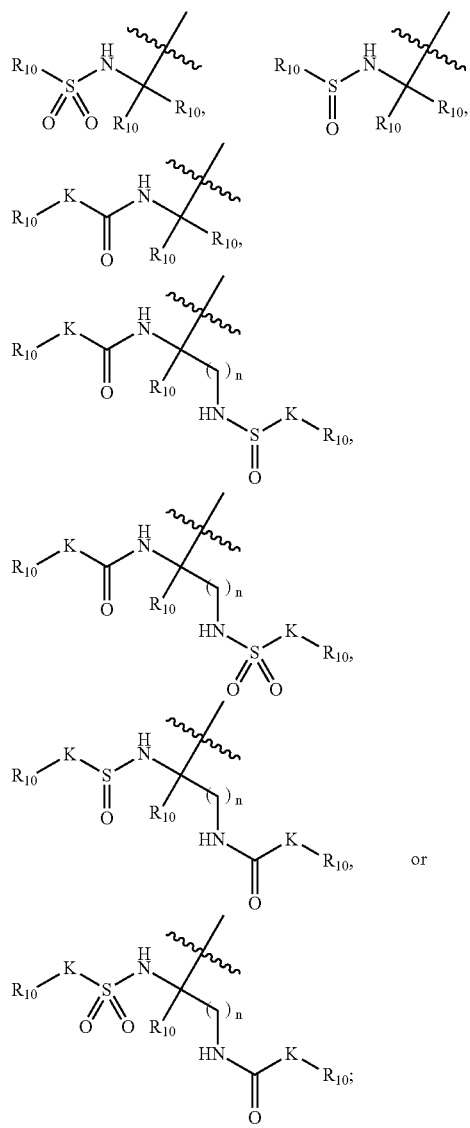

W is:

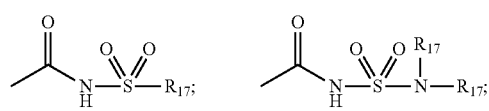

wherein each $R_{17}$ is independently:
(C6-C10)-aryl-, $R_5$ and $R_{5'}$ are independently hydrogen or (C1-C12)-aliphatic, wherein any hydrogen is optionally replaced with halogen, and wherein any terminal carbon atom is optionally substituted with sulfhydryl or hydroxy, and wherein up to two aliphatic carbon atoms may be replaced by a heteroatom selected from N, NH, O, S, SO, or SO$_2$; or $R_1$, $R_{1'}$, $R_{11'}$, $R_{13}$, and $R_{13'}$ are independently:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-, $R_{11}$ and $R_{12}$ together with the atoms to which they are bound form a 3- to a 20-membered mono-, cyclic heterocyclic ring system;
wherein each ring is either aromatic or nonaromatic;
wherein each heteroatom in the heterocyclic ring system is selected from the group consisting of N, NH, O, S, SO, and SO$_2$; and
wherein said ring has up to 3 substituents selected independently from J.

2. The compound according to claim 1 wherein W is:

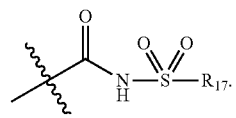

3. The compound according to claims 1, wherein the

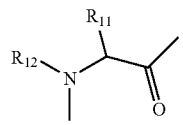

radical is:

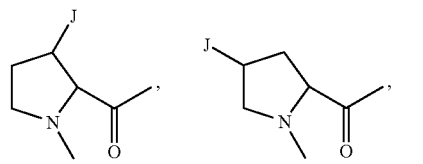

4. The compound according to claim 1, wherein $R_{11}$ and $R_{12}$ together with the atoms to which they are bound form a 6- to 10-membered mono-cyclic carbocyclic or heterocyclic ring system;

wherein each heteroatom in the heterocyclic ring system is selected from the group consisting of N, NH, O, S, SO, and SO$_2$; and wherein said ring has up to 3 substituents selected independently from J.

5. The compound according to claim 1 wherein R$_5$ and R$_5$,is:

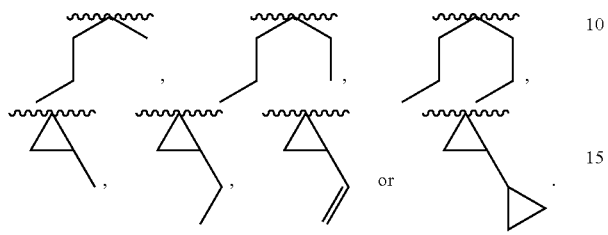

6. The compound according to claim 1 wherein R$_5$,is H and R$_5$ is (C1-C6)-alkyl, wherein the alkyl is optionally substituted with fluoro or —SH.

7. The compound according to claim 1 wherein R$_5$ and R$_5$,are independently:

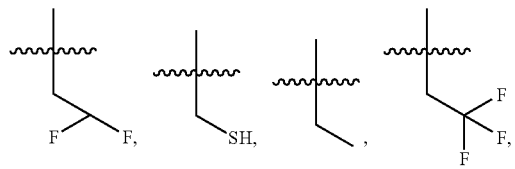

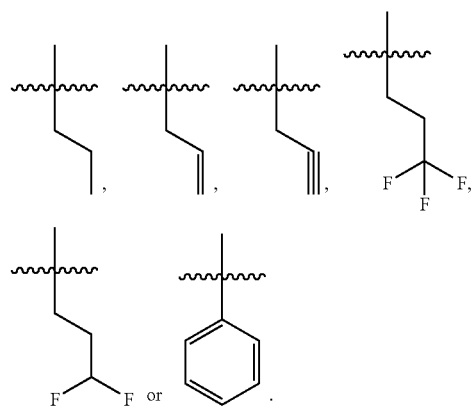

8. The compound according to claim 1 wherein R$_{13}$ is:

(C1-C6)-alkyl, (C3-C10)-cycloalkyl,

[(C3-C10)-cycloalkyl]-(C1-C12)-alkyl.

9. The compound according to claim 1 wherein R$_1$ if present is (C1-C6)-alkyl, (C3-C10)-cycloalkyl,

[(C3-C10)-cycloalkyl]-(C1-C12)-alkyl.

* * * * *